US008586320B2

(12) United States Patent
Frackelton, Jr. et al.

(10) Patent No.: US 8,586,320 B2
(45) Date of Patent: Nov. 19, 2013

(54) METHODS FOR PROGNOSING THE RECURRENCE OF GASTROINTESTINAL AND OTHER CANCERS USING THE SHC PROTEINS

(75) Inventors: A. Raymond Frackelton, Jr., Rumford, RI (US); Laurie Jean Hafer, East Fallowfield, PA (US)

(73) Assignee: Catalyst Oncology, LP, Worcester, MA (US)

(*) Notice: Subject to any disclaimer, the term of this patent is extended or adjusted under 35 U.S.C. 154(b) by 410 days.

(21) Appl. No.: 12/161,548

(22) PCT Filed: Mar. 21, 2006

(86) PCT No.: PCT/US2006/010728

§ 371 (c)(1),
(2), (4) Date: Sep. 19, 2008

(87) PCT Pub. No.: WO2007/084156

PCT Pub. Date: Jul. 26, 2007

(65) Prior Publication Data

US 2009/0220965 A1 Sep. 3, 2009

Related U.S. Application Data

(60) Provisional application No. 60/760,900, filed on Jan. 20, 2006.

(51) Int. Cl.
*G01N 33/53* (2006.01)

(52) U.S. Cl.
USPC .............................. 435/7.23; 436/64; 435/7.1

(58) Field of Classification Search
None
See application file for complete search history.

(56) References Cited

U.S. PATENT DOCUMENTS

2004/0033542 A1* 2/2004 Frackelton et al. .......... 435/7.23

FOREIGN PATENT DOCUMENTS

WO 03/073821 A2 9/2003
WO 2005038005 4/2005

OTHER PUBLICATIONS

Davol et al Cancer Res. vol. 63, p. 6772-6783, 2003.*
Devol et al Cancer Res vol. 63, p. 6772-6783, 2003, IDS filed on Oct. 24, 2008, item: 1.*
Mesh word search result , 2010.*
"Catalyst Oncology, Inc. Announces the Introduction of the Shc Test for the Assessment of Risk in Gastric Cancer Patients," Profile Products People Publication News Publications Patients Professions, http://web.archive.org/web/20070718009366/www.catalystoncology.com/news/12.html, Jun. 10, 2008.
Trinei, et al., "A p53-p66Shc Signalling Pathway Controls Intracellular Redox Status, Levels of Oxidation-Damaged DNA and oxidative Stress-Induced Apoptosis," Nature Publishing Group, Oncogene 2002, 21: 3872-3878.
Davol P. A. et al., 2003, "Shc Proteins Are Strong, Independent Prognostic markers for both Node-Negative and Node-Positive Primary Breast Cancer", Cancer Research, vol. 63, pp. 6772-6783.
Gotoh N. et al., 1995, "The SH2 domain of Shc suppresses EGF-induced mitogenesis in a dominant negative manner", Oncogene, vol. 11, pp. 2525-2533.
Jackson J. G. et al., 2000, "Elevated Levels of p66 Shc Are Found in Breast Cancer Cell Lines and Primary Tumors with High Metastatic Potential", Clinical Cancer Research, vol. 6, pp. 1135-1139.
Nolan M. K. et al., 1997, "Differential Roles of IRS-1 and Shc Signaling Pathways in Breast Cancer Cells", Int. J. Cancer, vol. 72, pp. 828-834.
Pelicci G. et al., 1995, "The Motogenic and Mitogenic Responses to HGF Are Amplified by the Shc Adaptor Protein", Oncogene, vol. 10, pp. 1631-1638.
Pellici G. et al.,1992, "A Novel Transforming Protein (Shc) with an SH2 Domain is Implicated in Mitogenic Signal Transduction", Cell, vol. 70, pp. 93-104.
Sasaoka T. et al., 1994, "Evidence for a Functional Role of Shc Proteins in Mitogenic Signaling Induced by Insulin, Insulin-like Growth Factor-1, and Epidermal Growth Factor", J. Biol. Chem., vol. 269, No. 18, pp. 13689-13694.
Song R. X. et al., 2004, "The Role of Shc and Insulin-like Growth factor 1 receptor in mediating the translocation of Estrogen Receptor and to the Plasma Membrane", Proc. Natl. Acad. Sci. USA, vol. 101, pp. 2076-2081.
Songyang Z. et al., 1993, "SH2 Domains Recognize Specific Phosphopeptide Sequences", Cell, vol. 72, pp. 767-778.
Stevenson L. E. et al., 1999, "Shc Dominant Negative Disrupts Cell Cycle Progression in Both G0-G1 and G2-M of ErbB2-positive Breast Cancer Cells", 1999, vol. 10, pp. 61-71.
Xie Y. et al., 1995, "Tyrosine phosphorylation of Shc Proteins and Formation of Shc/Grb2 complex correlate to the Transformation of NIH3T3 cells mediated by the point-mutation Activated neu", Oncogene, vol. 10, pp. 2409-2413.
Yukimasa S. et al., 2005, "Enhanced expression of p46 Shc in the nucleus and p52 Shc in the cytoplasm of human gastric cancer", Int. J. Onc., vol. 26, pp. 905-911.

* cited by examiner

*Primary Examiner* — Lei Yao
(74) *Attorney, Agent, or Firm* — Sutherland Asbill & Brennan LLP

(57) ABSTRACT

The invention relates to methods for prognosing the recurrence of gastrointestinal and other cancers using tyrosine phosphorylated Shc (PY-Shc) and/or p66-Shc.

11 Claims, 20 Drawing Sheets

SEQUENCE LISTING

```
<160> NUMBER OF SEQ ID NOS: 4

<210> SEQ ID NO 1
<211> LENGTH: 3076
<212> TYPE: DNA
<213> ORGANISM: Homo sapiens

<400> SEQUENCE: 1

gtttctccag ggaggcaggg cccggggaga aagttggagc ggtaacctaa gctggcagtg      60

gcgtgatccg gcaccaaatc ggcccgcggt gcggtgcgga gactccatga ggccctggac     120

atgaacaagc tgagtggagg cggcgggcgc aggactcggg tggaaggggg ccagcttggg     180
```

-continued

```
ggcgaggagt ggacccgcca cgggagcttt gtcaataagc ccacgcgggg ctggctgcat    240
cccaacgaca aagtcatggg acccggggtt tcctacttgg ttcggtacat gggttgtgtg    300
gaggtcctcc agtcaatgcg tgccctggac ttcaacaccc ggactcaggt caccagggag    360
gccatcagtc tggtgtgtga ggctgtgccg ggtgctaagg gggcgacaag gaggagaaag    420
ccctgtagcc gcccgctcag ctctatcctg ggaggagta acctgaaatt tgctggaatg    480
ccaatcactc tcaccgtctc caccagcagc ctcaacctca tggccgcaga ctgcaaacag    540
atcatcgcca accaccacat gcaatctatc tcatttgcat ccggcgggga tccggacaca    600
gccgagtatg tcgcctatgt tgccaaagac cctgtgaatc agagagcctg ccacattctg    660
gagtgtcccg aagggcttgc ccaggatgtc atcagcacca ttggccaggc cttcgagttg    720
cgcttcaaac aatacctcag gaacccaccc aaactggtca cccctcatga caggatggct    780
ggctttgatg gctcagcatg ggatgaggag gaggaagagc cacctgacca tcagtactat    840
aatgacttcc cggggaagga accccccttg gggggggtgg tagacatgag gcttcgggaa    900
ggagccgctc caggggctgc tcgacccact gcacccaatg cccagacccc cagccacttg    960
ggagctacat tgcctgtagg acagcctgtt gggggagatc cagaagtccg caaacagatg   1020
ccacctccac caccctgtcc agcaggcaga gagcttttg atgatccctc ctatgtcaac   1080
gtccagaacc tagacaaggc ccggcaagca gtgggtggtg ctgggccccc caatcctgct   1140
atcaatggca gtgcaccccg ggacctgttt gacatgaagc ccttcgaaga tgctcttcgc   1200
gtgcctccac ctccccagtc ggtgtccatg gctgagcagc tccgagggga gccctggttc   1260
catgggaagc tgagccggcg ggaggctgag gcactgctgc agctcaatgg ggacttcctg   1320
gtacgggaga gcacgaccac acctggccag tatgtgctca ctggcttgca gagtgggcag   1380
cctaagcatt tgctactggt ggaccctgag ggtgtggttc ggactaagga tcaccgcttt   1440
gaaagtgtca gtcaccttat cagctaccac atggacaatc acttgcccat catctctgcg   1500
ggcagcgaac tgtgtctaca gcaacctgtg gagcggaaac tgtgatctgc cctagcgctc   1560
tcttccagaa gatgccctcc aatcctttcc accctattcc ctaactctcg ggacctcgtt   1620
tgggagtgtt ctgtgggctt ggccttgtgt cagagctggg agtagcatgg actctgggtt   1680
tcatatccag ctgagtgaga gggtttgagt caaaagcctg ggtgagaatc ctgcctctcc   1740
ccaaacatta atcaccaaag tattaatgta cagagtggcc cctcacctgg gcctttcctg   1800
tgccaacctg atgccccttc cccaagaagg tgagtgcttg tcatggaaaa tgtcctgtgg   1860
tgacaggccc agtggaacag tcacccttct gggcaagggg gaacaaatca cacctctggg   1920
cttcagggta tcccagaccc ctctcaacac ccgccccccc catgtttaaa ctttgtgcct   1980
ttgaccatct cttaggtcta atgatatttt atgcaaacag ttcttggacc cctgaattca   2040
atgacaggga tgccaacacc ttcttggctt ctgggacctg tgttcttgct gagcaccctc   2100
tccggtttgg gttgggataa cagaggcagg agtggcagct gtcccctctc cctggggata   2160
tgcaaccctt agagattgcc ccagagcccc actcccggcc aggcgggaga tggacccctc   2220
ccttgctcag tgcctcctgg ccggggcccc tcaccccaag ggtctgtat atacatttca    2280
taaggcctgc cctcccatgt tgcatgccta tgtactctac gccaaagtgc agcccttcct   2340
cctgaagcct ctgccctgcc tccctttctg ggagggcggg gtgggggtga ctgaatttgg   2400
gcctcttgta cagttaactc tcccaggtgg attttgtgga ggtgagaaaa ggggcattga   2460
gactataaag cagtagacaa tccccacata ccatctgtag agttggaact gcattctttt   2520
aaagttttat atgcatatat tttagggctg tagacttact ttcctatttt cttttccatt   2580
```

-continued

```
gcttattctt gagcacaaaa tgataatcaa ttattacatt tatacatcac ctttttgact   2640

tttccaagcc cttttacagc tcttggcatt ttcctcgcct aggcctgtga ggtaactggg   2700

atcgcacctt ttataccaga gacctgaggc agatgaaatt tatttccatc taggactaga   2760

aaaacttggg tctcttaccg cgagactgag aggcagaagt cagcccgaat gcctgtcagt   2820

ttcatggagg ggaaacgcaa aacctgcagt tcctgagtac cttctacagg cccggcccag   2880

cctaggcccg gggtggccac accacagcaa gccggccccc cctcttttgg ccttgtggat   2940

aagggagagt tgaccgtttt catcctggcc tccttttgct gtttggatgt ttccacgggt   3000

ctcacttata ccaaagggaa aactcttcat taaagtccgt atttcttcta aaaaaaaaaa   3060

aaaaaaaaaa aaaaaa                                                   3076
```

<210> SEQ ID NO 2
<211> LENGTH: 474
<212> TYPE: PRT
<213> ORGANISM: Homo sapiens

<400> SEQUENCE: 2

```
Met Asn Lys Leu Ser Gly Gly Gly Gly Arg Arg Thr Arg Val Glu Gly
1               5                   10                  15

Gly Gln Leu Gly Gly Glu Glu Trp Thr Arg His Gly Ser Phe Val Asn
            20                  25                  30

Lys Pro Thr Arg Gly Trp Leu His Pro Asn Asp Lys Val Met Gly Pro
        35                  40                  45

Gly Val Ser Tyr Leu Val Arg Tyr Met Gly Cys Val Glu Val Leu Gln
    50                  55                  60

Ser Met Arg Ala Leu Asp Phe Asn Thr Arg Thr Gln Val Thr Arg Glu
65                  70                  75                  80

Ala Ile Ser Leu Val Cys Glu Ala Val Pro Gly Ala Lys Gly Ala Thr
                85                  90                  95

Arg Arg Arg Lys Pro Cys Ser Arg Pro Leu Ser Ser Ile Leu Gly Arg
            100                 105                 110

Ser Asn Leu Lys Phe Ala Gly Met Pro Ile Thr Leu Thr Val Ser Thr
        115                 120                 125

Ser Ser Leu Asn Leu Met Ala Ala Asp Cys Lys Gln Ile Ile Ala Asn
    130                 135                 140

His His Met Gln Ser Ile Ser Phe Ala Ser Gly Gly Asp Pro Asp Thr
145                 150                 155                 160

Ala Glu Tyr Val Ala Tyr Val Ala Lys Asp Pro Val Asn Gln Arg Ala
                165                 170                 175

Cys His Ile Leu Glu Cys Pro Glu Gly Leu Ala Gln Asp Val Ile Ser
            180                 185                 190

Thr Ile Gly Gln Ala Phe Glu Leu Arg Phe Lys Gln Tyr Leu Arg Asn
        195                 200                 205

Pro Pro Lys Leu Val Thr Pro His Asp Arg Met Ala Gly Phe Asp Gly
    210                 215                 220

Ser Ala Trp Asp Glu Glu Glu Glu Glu Pro Pro Asp His Gln Tyr Tyr
225                 230                 235                 240

Asn Asp Phe Pro Gly Lys Glu Pro Pro Leu Gly Gly Val Val Asp Met
                245                 250                 255

Arg Leu Arg Glu Gly Ala Ala Pro Gly Ala Ala Arg Pro Thr Ala Pro
            260                 265                 270

Asn Ala Gln Thr Pro Ser His Leu Gly Ala Thr Leu Pro Val Gly Gln
        275                 280                 285
```

-continued

```
Pro Val Gly Gly Asp Pro Glu Val Arg Lys Gln Met Pro Pro Pro Pro
    290                 295                 300

Pro Cys Pro Ala Gly Arg Glu Leu Phe Asp Asp Pro Ser Tyr Val Asn
305                 310                 315                 320

Val Gln Asn Leu Asp Lys Ala Arg Gln Ala Val Gly Gly Ala Gly Pro
                325                 330                 335

Pro Asn Pro Ala Ile Asn Gly Ser Ala Pro Arg Asp Leu Phe Asp Met
            340                 345                 350

Lys Pro Phe Glu Asp Ala Leu Arg Val Pro Pro Pro Pro Gln Ser Val
        355                 360                 365

Ser Met Ala Glu Gln Leu Arg Gly Glu Pro Trp Phe His Gly Lys Leu
    370                 375                 380

Ser Arg Arg Glu Ala Glu Ala Leu Leu Gln Leu Asn Gly Asp Phe Leu
385                 390                 395                 400

Val Arg Glu Ser Thr Thr Thr Pro Gly Gln Tyr Val Leu Thr Gly Leu
                405                 410                 415

Gln Ser Gly Gln Pro Lys His Leu Leu Leu Val Asp Pro Glu Gly Val
            420                 425                 430

Val Arg Thr Lys Asp His Arg Phe Glu Ser Val Ser His Leu Ile Ser
        435                 440                 445

Tyr His Met Asp Asn His Leu Pro Ile Ile Ser Ala Gly Ser Glu Leu
    450                 455                 460

Cys Leu Gln Gln Pro Val Glu Arg Lys Leu
465                 470


<210> SEQ ID NO 3
<211> LENGTH: 1752
<212> TYPE: DNA
<213> ORGANISM: Homo sapiens

<400> SEQUENCE: 3

atgaatctcc tgccccccaa gcccaagtac aatccactcc ggaatgagtc tctgtcatcg      60

atggaggaag gggcttctgg gtccaccccc ccggaggagc tgccttcccc accagcttca     120

tccctggggc ccatcctgcc tcctctgcct ggggacgata gtcccactac cctgtgctcc     180

ttcttccccc ggatgagcaa cctgaggctg gccaacccgg ctgggggggcg cccagggtct     240

aagggggagc caggaagggc agctgatgat ggggagggga tcgtaggggc agccatgcca     300

gactcaggcc ccctacccct cctccaggac atgaacaagc tgagtggagg cggcgggcgc     360

aggactcggg tggaaggggg ccagcttggg ggcgaggagt ggacccgcca cgggagcttt     420

gtcaataagc ccacgcgggg ctggctgcat cccaacgaca aagtcatggg acccggggtt     480

tcctacttgg ttcggtacat gggttgtgtg gaggtcctcc agtcaatgcg tgccctggac     540

ttcaacaccc ggactcaggt caccagggag gccatcagtc tggtgtgtga ggctgtgccg     600

ggtgctaagg gggcgacaag gaggagaaag ccctgtagcc gcccgctcag ctctatcctg     660

gggaggagta acctgaaatt tgctggaatg ccaatcactc tcaccgtctc caccagcagc     720

ctcaacctca tggccgcaga ctgcaaacag atcatcgcca accaccacat gcaatctatc     780

tcatttgcat ccggcgggga tccggacaca gccgagtatg tcgcctatgt tgccaaagac     840

cctgtgaatc agagagcctg ccacattctg gagtgtcccg aagggcttgc ccaggatgtc     900

atcagcacca ttggccaggc cttcgagttg cgcttcaaac aatacctcag gaacccaccc     960

aaactggtca cccctcatga caggatggct ggctttgatg gctcagcatg ggatgaggag    1020

gaggaagagc cacctgacca tcagtactat aatgacttcc cggggaagga accccccttg    1080
```

-continued gggggggtgg tagacatgag gcttcgggaa ggagccgctc caggggctgc tcgacccact 1140
gcacccaatg cccagacccc cagccacttg ggagctacat tgcctgtagg acagcctgtt 1200
gggggagatc cagaagtccg caaacagatg ccacctccac caccctgtcc aggcagagag 1260
ctttttgatg atccctccta tgtcaacgtc cagaacctag acaaggcccg gcaagcagtg 1320
ggtggtgctg ggcccccaa tcctgctatc aatggcagtg caccccggga cctgtttgac 1380
atgaagccct tcgaagatgc tcttcgggtg cctccacctc cccagtcggt gtccatggct 1440
gagcagctcc gaggggagcc ctggttccat gggaagctga gccggcggga ggctgaggca 1500
ctgctgcagc tcaatgggga cttcttggta cgggagagca cgaccacacc tggccagtat 1560
gtgctcactg gcttgcagag tgggcagcct aagcatttgc tactggtgga ccctgagggt 1620
gtggttcgga ctaaggatca ccgctttgaa agtgtcagtc accttatcag ctaccacatg 1680
gacaatcact tgcccatcat ctctgcgggc agcgaactgt gtctacagca acctgtggag 1740
cggaaactgt ga 1752

<210> SEQ ID NO 4
<211> LENGTH: 583
<212> TYPE: PRT
<213> ORGANISM: Homo sapiens

<400> SEQUENCE: 4

Met Asn Leu Leu Pro Pro Lys Pro Lys Tyr Asn Pro Leu Arg Asn Glu
1 5 10 15

Ser Leu Ser Ser Met Glu Glu Gly Ala Ser Gly Ser Thr Pro Pro Glu
20 25 30

Glu Leu Pro Ser Pro Pro Ala Ser Ser Leu Gly Pro Ile Leu Pro Pro
35 40 45

Leu Pro Gly Asp Asp Ser Pro Thr Thr Leu Cys Ser Phe Phe Pro Arg
50 55 60

Met Ser Asn Leu Arg Leu Ala Asn Pro Ala Gly Gly Arg Pro Gly Ser
65 70 75 80

Lys Gly Glu Pro Gly Arg Ala Ala Asp Asp Gly Glu Gly Ile Val Gly
85 90 95

Ala Ala Met Pro Asp Ser Gly Pro Leu Pro Leu Leu Gln Asp Met Asn
100 105 110

Lys Leu Ser Gly Gly Gly Gly Arg Arg Thr Arg Val Glu Gly Gly Gln
115 120 125

Leu Gly Gly Glu Glu Trp Thr Arg His Gly Ser Phe Val Asn Lys Pro
130 135 140

Thr Arg Gly Trp Leu His Pro Asn Asp Lys Val Met Gly Pro Gly Val
145 150 155 160

Ser Tyr Leu Val Arg Tyr Met Gly Cys Val Glu Val Leu Gln Ser Met
165 170 175

Arg Ala Leu Asp Phe Asn Thr Arg Thr Gln Val Thr Arg Glu Ala Ile
180 185 190

Ser Leu Val Cys Glu Ala Val Pro Gly Ala Lys Gly Ala Thr Arg Arg
195 200 205

Arg Lys Pro Cys Ser Arg Pro Leu Ser Ser Ile Leu Gly Arg Ser Asn
210 215 220

Leu Lys Phe Ala Gly Met Pro Ile Thr Leu Thr Val Ser Thr Ser Ser
225 230 235 240

Leu Asn Leu Met Ala Ala Asp Cys Lys Gln Ile Ile Ala Asn His His
245 250 255

-continued

```
Met Gln Ser Ile Ser Phe Ala Ser Gly Gly Asp Pro Asp Thr Ala Glu
            260                 265                 270

Tyr Val Ala Tyr Val Ala Lys Asp Pro Val Asn Gln Arg Ala Cys His
        275                 280                 285

Ile Leu Glu Cys Pro Glu Gly Leu Ala Gln Asp Val Ile Ser Thr Ile
    290                 295                 300

Gly Gln Ala Phe Glu Leu Arg Phe Lys Gln Tyr Leu Arg Asn Pro Pro
305                 310                 315                 320

Lys Leu Val Thr Pro His Asp Arg Met Ala Gly Phe Asp Gly Ser Ala
                325                 330                 335

Trp Asp Glu Glu Glu Glu Glu Pro Pro Asp His Gln Tyr Tyr Asn Asp
            340                 345                 350

Phe Pro Gly Lys Glu Pro Pro Leu Gly Gly Val Val Asp Met Arg Leu
        355                 360                 365

Arg Glu Gly Ala Ala Pro Gly Ala Ala Arg Pro Thr Ala Pro Asn Ala
    370                 375                 380

Gln Thr Pro Ser His Leu Gly Ala Thr Leu Pro Val Gly Gln Pro Val
385                 390                 395                 400

Gly Gly Asp Pro Glu Val Arg Lys Gln Met Pro Pro Pro Pro Pro Cys
                405                 410                 415

Pro Gly Arg Glu Leu Phe Asp Asp Pro Ser Tyr Val Asn Val Gln Asn
            420                 425                 430

Leu Asp Lys Ala Arg Gln Ala Val Gly Gly Ala Gly Pro Pro Asn Pro
        435                 440                 445

Ala Ile Asn Gly Ser Ala Pro Arg Asp Leu Phe Asp Met Lys Pro Phe
    450                 455                 460

Glu Asp Ala Leu Arg Val Pro Pro Pro Pro Gln Ser Val Ser Met Ala
465                 470                 475                 480

Glu Gln Leu Arg Gly Glu Pro Trp Phe His Gly Lys Leu Ser Arg Arg
                485                 490                 495

Glu Ala Glu Ala Leu Leu Gln Leu Asn Gly Asp Phe Leu Val Arg Glu
            500                 505                 510

Ser Thr Thr Thr Pro Gly Gln Tyr Val Leu Thr Gly Leu Gln Ser Gly
        515                 520                 525

Gln Pro Lys His Leu Leu Leu Val Asp Pro Glu Gly Val Val Arg Thr
    530                 535                 540

Lys Asp His Arg Phe Glu Ser Val Ser His Leu Ile Ser Tyr His Met
545                 550                 555                 560

Asp Asn His Leu Pro Ile Ile Ser Ala Gly Ser Glu Leu Cys Leu Gln
                565                 570                 575

Gln Pro Val Glu Arg Lys Leu
            580
```

METHODS FOR PROGNOSING THE RECURRENCE OF GASTROINTESTINAL AND OTHER CANCERS USING THE SHC PROTEINS

RELATED APPLICATIONS

This application claims priority to U.S. Provisional Application No. 60/760,900, filed on Jan. 20, 2006, the entire contents of which are incorporated herein by this reference.

BACKGROUND OF THE INVENTION

Extensive molecular-biochemical studies of normal and cancerous cells have revealed that abnormality in the signal transmission involved in the growth and division of cells causes cancer, and also that proteins produced by the expression of oncogenic genes regulate the growth and division of cells. Namely, it has been reported that growth factors, growth factor receptors, cellular tyrosine and serine/threonine kinases and phosphatases, Ras proteins, adaptor proteins, transcription factors, and the like take part in the intracellular signal transmission and play crucial roles in cell proliferation (see, for example, Alexander, L. (1994) *Eur. J. Biochem.* 226, 1-13; Hahn W. C. and Weinberg R. A. (2002) *Nat Rev Cancer* 2(5):331-41; Blume-Jensen P. and Hunter T. (2001) *Nature* 411(6835):355-65).

For example, intracellular signal transmission through Ras occurs when a signal transmitting substance binds to a growth factor receptor, such as, for example, ErbB2, which causes phosphorylation of tyrosine on the receptors. The receptors phosphorylate tyrosine 317 in Shc (Src homology and collagen protein), which in turn is recognized by Grb2-(Growth factor receptor-binding protein-2) SOS complexes. As a result, SOS is translocated to the cellular membrane which appears to facilitate its ability to activate Ras (see, for example, Batzer, A. G., et al. (1994) Mol Cell Biol 14(8): 5192-201; Buday, L. and J. Downward (1993) *Cell* 73: 611-620; Feig, L. A. (1994) *Curr Opin Cell Biol* 6(2): 204-11; Karin, M. and T. Hunter (1995) *Curr Biol* 5(7): 747-57; Meyer, S., et al. (1994) *Mol Cell Biol* 14(5): 3253-62; Seger, R. and E. G. Krebs (1995) *Faseb J*9(9): 726-35; Segatto, O., et al. (1993) *Oncogene* 8(8): 2105-12; Sutherland, R. L., C. K. Watts, and E. A. Musgrove (1993) *J Steroid Biochem Mol Biol* 47(1-6): 99-106) leading to stimulation of DNA synthesis, cell proliferation and differentiation.

Furthermore, several studies using microinjected antibodies to Shc, Shc antisense, and various Shc dominant-negative constructs have shown the dependence on a functional Shc for signaling through the EGF receptor, Her2/Neu, IGF-1 and HGF (see, for example, Nolan, M. K., et al. (1997) *Int J Cancer* 72(5): 828-3; Xie, Y., K et al. (1995) *Oncogene* 1995. 10(12): 2409-2413; Gotoh, N., et al. (1995) *Oncogene* 11(12): 2525-2533; Pelicci, G., et al. (1995) *Oncogene* 10(8): 1631-8; Sasaoka, T., et al. (1994) *J Biol Chem* 269(18): 13689-94; Stevenson, L. A., et al. (1999) *Cell Growth & Differentiation* 10(1): 61-71); and Song, R. X., et al. (2006) *Proc Natl Acad Sci USA* 101(7):2076-4081). There are three isoforms of Shc: p66, p52 and p46 of 66, 52, and 46 kDa, respectively (see, for example, Songyang, Z., et al. (1993) *Cell* 72(5): 767-78; Pelicci, G., et al. (1992) *Cell* 70(1): 93-104; Rozalis-Adcock, M., et al. (1992) *Nature* 360(6405): 689-92). The p66 Shc isoform contains a unique N-terminal domain ($CH_2$) not found in the p52 or p46 Shc isoforms (Pelicci, G., et al. (1992) *Cell* 70(1):93-104). In contrast to p52 and p46 Shc, p66 Shc typically does not activate the MAP kinase signaling cascade but rather actually inhibits the ability of growth factors to activate both MAP kinase and c-fos (Migliaccio, E., et al. (1997) *Embo J* 16(4): 706-16; Pacini, S., et al. (2004) *Mol Cell Biol* 24:1747-57; Trinei, M., et al. (2002) *Oncogene* 21:3872-8). Additionally, p66 Shc is an apoptotic sensitizer to oxidative stress (Migliaccio, E. et al. (1999) *Nature* 402(6759):309-313; Nemoto, S. et al. (2002) *Science* 295(5564):2450-2452; Orsini, F. et al., (2004) *J Biol Chem* 279(24):25689-25695; Pacini, S. et al. (2004) *Mol Cell Biol* 24(4):1747-1757; Purdom, S. et al. (2003) *Trends Mol Med* 9(5):206-210; and Trinei, M. et al. (2002) *Oncogene* 21(24):3872-3878). Such stress may be generated by chronic activation of growth-factor pathways, by infiltrating neutrophils and macrophages, and/or by neo-vascularization of hypoxic tumors (Brown, N. S. et al. (2001) *Breast Cancer Res* 3(5):323-327; Irani, K. et al. (1997) *Science* 275(5306):1649-1652).

For patients diagnosed with cancer, e.g., gastrointestinal cancer, surgical and medical oncologists currently must balance the minimal likely benefit that might be derived from the aggressive level D2 surgery and toxic chemo-radiation regimen adopted by some as the current standard of care (MacDonald, J. (2001) *N. Engl J Med* 345:725-730) against the modest risk (approximately 20%) that patients with early stage cancer treated only by level D1 surgical resection will have recurrent disease. Prognostic markers that will identify patients who are likely (and those unlikely) to experience recurrent disease will aid and improve this clinical treatment decision.

Thus, there is an urgent need in the field for better prognostic indicators to guide the vigor and extent of surgical and adjuvant therapies of patients, especially those with early stage cancer.

SUMMARY OF THE INVENTION

The present invention is based, at least in part, on the discovery that the amount of tyrosine phosphorylated Shc (PY-Shc) and/or p66-Shc, and/or a Shc mathematical relationship, e.g., the Shc ratio and/or the PYp66-Shc product, in a sample can prognose the recurrence of cancer in a subject being treated for cancer, e.g., gastrointestinal cancer, as well as the survival of a subject being treated for cancer, e.g., gastrointestinal cancer. Specifically, Applicants have demonstrated for the first time that a decreased amount of tyrosine phosphorylated Shc (PY-Shc) and/or an increased amount of p66-Shc in a sample from a subject being treated for gastric cancer correlates with cancer recurrence in the subject, and that an increased amount of tyrosine phosphorylated Shc (PY-Shc) and/or a decreased amount of p66-Shc in a sample from a subject being treated for gastric cancer correlates with the absence of cancer recurrence in the subject. Similarly, it has been demonstrated for the first time that a decreased amount of tyrosine phosphorylated Shc (PY-Shc) and/or an increased amount of p66-Shc in a sample from a subject being treated for gastric cancer correlates with subject death, and that an increased amount of tyrosine phosphorylated Shc (PY-Shc) and/or a decreased amount of p66-Shc in a sample from a subject being treated for gastric cancer correlates with subject survival.

Applicants have also demonstrated for the first time that an increased amount of p66-Shc in a sample from a subject being treated for colon cancer correlates with cancer recurrence in the subject, and that a decreased amount of p66-Shc in a sample from a subject being treated for colon cancer correlates with the absence of cancer recurrence in the subject. Similarly, it has been demonstrated for the first time that an increased amount of p66-Shc in a sample from a subject being treated for colon cancer correlates with subject death, and that a decreased amount of p66-Shc in a sample from a subject being treated for colon cancer correlates with subject survival. In addition, Applicants have demonstrated for the first time that a low Shc mathematical relationship, i.e., a low Shc ratio, in a sample from a subject being treated for colon cancer correlates with cancer recurrence in the subject, and that a high Shc ratio in a sample from a subject being treated for colon cancer correlates with the absence of cancer recurrence in the subject. Similarly, it has been demonstrated for the first time that a low Shc mathematical relationship, i.e., a low Shc ratio, in a sample from a subject being treated for colon cancer correlates with subject death, and that that a high Shc ratio in a sample from a subject being treated for colon cancer correlates with subject survival. Furthermore, it has also been demonstrated by Applicants for the first time that a high Shc mathematical relationship, i.e., a high PYp66-Shc product, in a sample from a subject being treated for colon cancer correlates with subject death, and that a low PYp66-Shc product in a sample from a subject being treated for colon cancer correlates with subject survival.

It has also been demonstrated for the first time, that high levels of p66-Shc in combination with the presence of mutated or accumulated TP53 in a sample derived from a subject correlates with cancer recurrence in a subject. Similarly, it has been shown for the first time that high levels of p66-Shc and the absence of mutated or accumulated TP53 in a sample derived from a subject correlates with lack of cancer recurrence.

Accordingly, the present invention provides methods for prognosing cancer recurrence in a subject, e.g., a human, being treated for cancer. The methods include determining the amount of tyrosine phosphorylated Shc (PY-Shc) and/or p66-Shc present in a sample derived from the subject; and comparing the foregoing amount of tyrosine phosphorylated Shc (PY-Shc) and/or p66-Shc to a control amount of tyrosine phosphorylated Shc (PY-Shc) and/or p66-Shc present in a control sample, thereby prognosing cancer recurrence in the subject being treated for cancer.

In another aspect, the invention provides a method for prognosing survival of a subject, e.g., a human, being treated for cancer. The method includes determining the amount of tyrosine phosphorylated Shc (PY-Shc) and/or p66-Shc present in a sample obtained from the subject, and comparing the foregoing amount of tyrosine phosphorylated Shc (PY-Shc) and/or p66-Shc to a control amount of tyrosine phosphorylated Shc (PY-Shc) and/or p66-Shc present in a control sample, thereby prognosing survival of the subject being treated for cancer.

In yet another aspect, the invention provides a method for prognosing cancer recurrence in a subject, e.g., a human, being treated for gastrointestinal cancer by obtaining a gastrointestinal tissue sample from the subject; contacting the gastrointestinal tissue sample with an antibody that specifically binds to tyrosine phosphorylated Shc (PY-Shc) and/or p66-Shc in the sample; determining the amount of tyrosine phosphorylated Shc (PY-Shc) and/or p66-Shc in the sample by detecting tyrosine phosphorylated Shc (PY-Shc) and/or p66-Shc using the antibody and an immunohistochemical assay; comparing the amount of tyrosine phosphorylated Shc (PY-Shc) and/or p66-Shc in the sample to a control amount of tyrosine phosphorylated Shc (PY-Shc) and/or p66-Shc present in a control sample, wherein a decreased amount of tyrosine phosphorylated Shc (PY-Shc) and/or an increased amount of p66-Shc in the sample relative to the amount in the control sample indicates that the gastrointestinal cancer will recur in the subject, and an increased amount of tyrosine phosphorylated Shc (PY-Shc) and/or a decreased amount of p66-Shc in the sample relative to the amount in the control sample indicates that the gastrointestinal cancer will not recur in the subject, thereby prognosing cancer recurrence in a subject being treated for gastrointestinal cancer.

In another aspect, the invention provides a method for prognosing cancer recurrence in a subject, e.g., a human, being treated for gastric cancer. The method includes determining the amount of tyrosine phosphorylated Shc (PY-Shc) and/or p66-Shc present in a sample derived from the subject, and comparing the foregoing amount of tyrosine phosphorylated Shc (PY-Shc) and/or p66-Shc to a control amount of tyrosine phosphorylated Shc (PY-Shc) and/or p66-Shc present in a control sample, wherein a decreased amount of tyrosine phosphorylated Shc (PY-Shc) and/or an increased amount of p66-Shc in the sample indicates that the gastric cancer will recur in the subject, and an increased amount of tyrosine phosphorylated Shc (PY-Shc) and/or a decreased amount of p66-Shc in the sample indicates that the gastric cancer will not recur in said subject, thereby prognosing cancer recurrence in the subject being treated for gastric cancer.

In another aspect, the invention provides a method for prognosing cancer recurrence in a subject, e.g., a human, being treated for colon cancer. The method includes determining the amount of p66-Shc present in a sample derived from the subject, and comparing the foregoing amount to a control amount of p66-Shc present in a control sample, wherein an increased amount of p66-Shc in the sample indicates that the colon cancer will recur in the subject, thereby prognosing cancer recurrence in the subject being treated for colon cancer.

In yet another aspect, the invention provides a method for prognosing cancer recurrence in a subject, e.g., a human, being treated for colon cancer. The method includes determining the Shc ratio in a sample derived from the subject, and comparing the foregoing Shc ratio to a control Shc ratio present in a control sample, wherein a lower Shc ratio in the sample indicates that the colon cancer will recur in the subject, and a higher Shc ratio in the sample indicates that the colon cancer will not recur in the subject, thereby prognosing cancer recurrence in said subject being treated for colon cancer.

In another aspect, the invention provides a method for prognosing cancer recurrence in a subject e.g., a human, being treated for colon cancer. The method includes determining the PYp66-Shc product in a sample derived from the subject, and comparing the foregoing PYp66-Shc product to a control PYp66-Shc product in a control sample, wherein a higher PYp66-Shc product in the sample indicates that the colon cancer will recur in the subject, and a lower PYp66-Shc product in the sample indicates that the colon cancer will not recur in the subject, thereby prognosing cancer recurrence in the subject being treated for colon cancer.

In one embodiment of the invention, the method is performed in conjunction with a morphological analysis of the sample obtained from the subject.

In one embodiment, the sample is selected from the group consisting of tissue, e.g., gastric tissue, small intestine tissue, or large intestine tissue, or cells.

In one embodiment, the cancer is gastric cancer, e.g., stage I gastric cancer or stage II gastric cancer.

In one embodiment, the cancer is colon cancer, e.g., stage II colon cancer or stage III colon cancer.

In one embodiment, only the amount of p66-Shc is determined. In another embodiment, only the amount of tyrosine phosphorylated Shc (PY-Shc) is determined.

In yet another embodiment, the amounts of both p66-Shc and tyrosine phosphorylated Shc (PY-Shc) are determined. In one embodiment, a Shc mathematical relationship is determined. In one embodiment, the Shc mathematical relationship that is determined is the Shc ratio. In another embodiment, the Shc mathematical relationship that is determined is the PYp66-Shc product.

In one embodiment, determining the amount of tyrosine phosphorylated Shc (PY-Shc) and p66-Shc comprises the use of a detectable antibody that specifically binds to p66-Shc or tyrosine phosphorylated Shc (PY-Shc). In such embodiments, the determination step may comprise the use of a technique selected from the group consisting of immunohistochemistry, immunocytochemistry, flow cytometry, ELISA, and mass spectrometry. In another embodiment, the amount of p66-Shc is determined at the nucleic acid level. In such embodiments, the amount of the nucleic acid is determined using a technique selected from the group consisting of quantitative PCR and expression array analysis.

In another aspect, the invention provides a method for determining whether a cancer cell is aggressive. The method involves determining the amount of tyrosine phosphorylated Shc (PY-Shc) and/or p66-Shc present in the cell, and comparing the foregoing amount of tyrosine phosphorylated Shc (PY-Shc) and/or p66-Shc to a control amount of tyrosine phosphorylated Shc (PY-Shc) and/or p66-Shc present in a control sample, thereby determining whether the cancer cell is aggressive.

In one embodiment, the cancer cell is a gastrointestinal cancer cell.

In one embodiment, the cancer cell is present within a tissue sample, e.g., a gastric tissue sample, a small intestine tissue sample, or a large intestine tissue sample.

In yet another aspect, the invention provides a method of assessing the efficacy of a treatment regimen for treating gastrointestinal cancer, e.g., colon or gastric cancer, in a subject. The method involves comparing the amount of tyrosine phosphorylated Shc (PY-Shc) and/or p66-Shc present in a first sample obtained from the subject prior to administering at least a portion of the treatment regimen to the subject; and the amount of tyrosine phosphorylated Shc (PY-Shc) and/or p66-Shc present in a second sample obtained from the subject following administration of at least a portion of the treatment regimen, wherein a lower amount of tyrosine phosphorylated Shc (PY-Shc) present in the first sample, relative to the second sample, is an indication that the treatment regimen is efficacious for treating gastrointestinal cancer, and wherein a significantly higher amount of p66-Shc present in the first sample, relative to the second sample, is an indication that the treatment regimen is efficacious for treating gastrointestinal cancer in the subject.

In another aspect, the invention provides a method of assessing the efficacy of a treatment regimen for treating gastrointestinal cancer, e.g., colon cancer, in a subject. The method involves comparing the Shc ratio present in a first sample obtained from the subject prior to administering at least a portion of the treatment regimen to the subject, and the Shc ratio present in a second sample obtained from the subject following administration of at least a portion of the treatment regimen, wherein a higher Shc ratio present in the second sample, relative to the first sample, is an indication that the treatment regimen is efficacious for treating colon cancer, and wherein a lower Shc ratio in the second sample, relative to the first sample, is an indication that the treatment regimen is not efficacious for treating colon cancer in the subject.

In another aspect, the invention provides a method of assessing the efficacy of a treatment regimen for treating gastrointestinal cancer, e.g., colon cancer, in a subject. The method involves comparing the PYp66-Shc product present in a first sample obtained from the subject prior to administering at least a portion of the treatment regimen to the subject, and the PYp66-Shc product present in a second sample obtained from the subject following administration of at least a portion of the treatment regimen, wherein a lower PYp66-Shc product present in the second sample, relative to the first sample, is an indication that the treatment regimen is efficacious for treating colon cancer, and wherein a higher PYp66-Shc product in the second sample, relative to the first sample, is an indication that the treatment regimen is not efficacious for treating colon cancer in the subject.

In one embodiment, the treatment regimen comprises a treatment regimen selected from the group consisting of surgery, radiation, hormone therapy, antibody therapy, therapy with protein tyrosine kinase inhibitors, serine/threonine kinase inhibitors, growth factors, cytokines, and chemotherapy. In another embodiment, the method is performed in conjunction with a morphological analysis of the sample obtained from the subject.

In another aspect, the invention provides a method of selecting a compound capable of modulating the aggressiveness of a gastrointestinal cancer cell. The method involves contacting a gastrointestinal cancer cell with a test compound, and determining the ability of the test compound to modulate the expression and/or activity of tyrosine phosphorylated Shc (PY-Shc) and/or p66-Shc in the gastrointestinal cancer cell, thereby identifying a compound capable of modulating the aggressiveness of a gastrointestinal cancer cell.

In one embodiment, the ability of the test compound to increase the expression and/or activity of tyrosine phosphorylated Shc (PY-Shc) and/or to decrease the expression and/or activity of p66-Shc in the cell would indicate that the compound is capable of decreasing the aggressiveness of a gastrointestinal cancer cell.

The invention further provides kits for use with the methods of the invention. The kits may comprise one or more of the following: a detectable antibody that specifically binds to p66-Shc, a detectable antibody that specifically binds to tyrosine phosphorylated Shc (PY-Shc), reagents for isolating gastrointestinal tissue or gastrointestinal cells, and instructions for use.

In another aspect, the invention provides a method for prognosing cancer recurrence in a subject being treated for cancer. The method involves determining the presence or absence of mutated TP53 in the sample derived from a subject, determining the amount of tyrosine phosphorylated Shc (PY-Shc) and/or p66-Shc present in the sample derived from the subject; comparing the presence or absence of the mutated TP53 to the presence or absence of mutated TP53 present in a control sample; and comparing the amount of tyrosine phosphorylated Shc (PY-Shc) and/or p66-Shc to a control amount of tyrosine phosphorylated Shc (PY-Shc) and/or p66-Shc present in a control sample, thereby prognosing cancer recurrence in the subject being treated for cancer.

In one embodiment, an increased amount of p66-Shc and the presence of mutated TP53 in the sample indicates that the cancer will recur in the subject. In another embodiment, an increased amount of p66-Shc and the absence of mutated TP53 in the sample indicates that the cancer will not recur in the subject

DETAILED DESCRIPTION OF THE INVENTION

Figure 1:
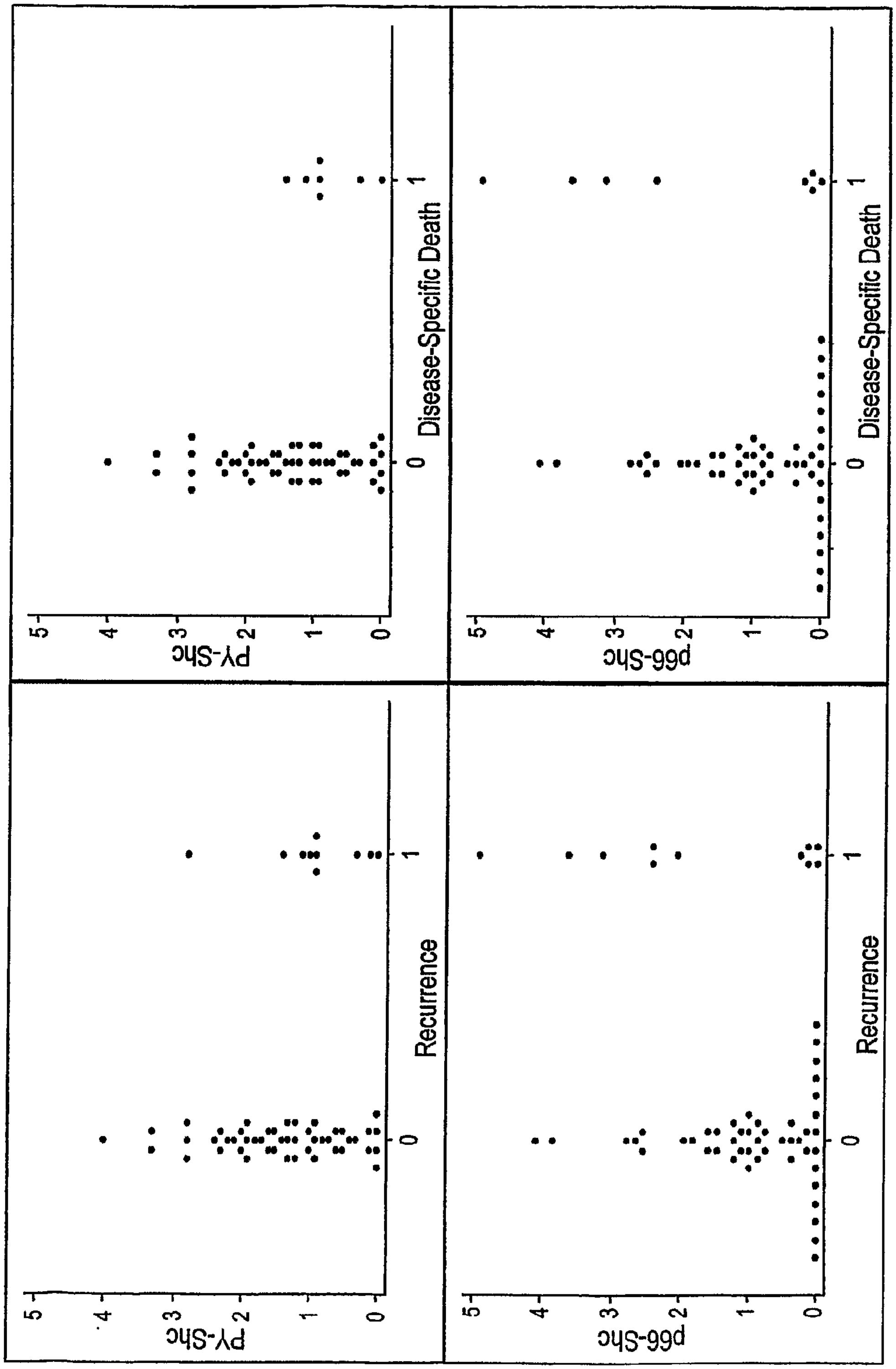
FIG. 1 depicts a dot plot of PY-Shc versus RFS % (the percentage of patients surviving without recurrence) and DFS % (the percentage of patients not dying of disease) in patients with Stage I and Stage II gastric cancer using Shc Markers.

The present invention is based, at least in part, on the discovery that the amount of tyrosine phosphorylated Shc (PY-Shc) and/or p66-Shc, and/or a Shc mathematical relationship in a sample can prognose the recurrence of cancer in a subject being treated for cancer, e.g., gastrointestinal cancer as well as the survival of a subject being treated for cancer, e.g., gastrointestinal cancer. Specifically, Applicants have demonstrated for the first time that a decreased amount of tyrosine phosphorylated Shc (PY-Shc) and/or an increased amount of p66-Shc in a sample from a subject being treated for gastric cancer correlates with cancer recurrence in the subject, and that an increased amount of tyrosine phosphorylated Shc (PY-Shc) and/or a decreased amount of p66-Shc in a sample from a subject being treated for gastric cancer correlates with the absence of cancer recurrence in the subject. Similarly, it has been demonstrated for the first time that a decreased amount of tyrosine phosphorylated Shc (PY-Shc) and/or an increased amount of p66-Shc in a sample from a subject being treated for cancer correlates with subject death, and that an increased amount of tyrosine phosphorylated Shc (PY-Shc) and/or a decreased amount of p66-Shc in a sample from a subject being treated for cancer correlates with subject survival.

Applicants have also demonstrated for the first time that an increased amount of p66-Shc in a sample from a subject being treated for colon cancer correlates with cancer recurrence in the subject, and that a decreased amount of p66-Shc in a sample from a subject being treated for colon cancer correlates with the absence of cancer recurrence in the subject. Similarly, it has been demonstrated for the first time that an increased amount of p66-Shc in a sample from a subject being treated for colon cancer correlates with subject death, and that a decreased amount of p66-Shc in a sample from a subject being treated for colon cancer correlates with subject survival. In addition, Applicants have demonstrated for the first time that a low Shc mathematical relationship, i.e., a low Shc ratio, in a sample from a subject being treated for colon cancer correlates with cancer recurrence in the subject, and that a high Shc mathematical relationship, i.e., a high Shc ratio, in a sample from a subject being treated for colon cancer correlates with the absence of cancer recurrence in the subject. Similarly, it has been demonstrated for the first time that a low Shc mathematical relationship, i.e., a low Shc ratio, in a sample from a subject being treated for colon cancer correlates with subject death, and that that a high Shc mathematical relationship, i.e., a high Shc ratio, in a sample from a subject being treated for colon cancer correlates with subject survival. Furthermore, it has also been demonstrated by Applicants for the first time that a high Shc mathematical relationship, i.e., a high PYp66-Shc product, in a sample from a subject being treated for colon cancer correlates with subject death, and that a low Shc mathematical relationship, i.e., a low PYp66-Shc product, in a sample from a subject being treated for colon cancer correlates with subject survival.

It has also been demonstrated for the first time, that high levels of p66-Shc in combination with the presence of mutated or accumulated TP53 in a sample derived from a subject correlates with cancer recurrence and subject death. Similarly, it has been shown for the first time that high levels of p66-Shc and the absence of mutated or accumulated TP53 in a sample derived from a subject correlates with subject survival or lack of cancer recurrence.

Accordingly, methods, reagents, and kits are provided herein for prognosing cancer recurrence and/or survival in a subject, as well as methods for determining whether a gastrointestinal cancer cell is aggressive, methods of assessing the efficacy of a treatment regimen for treating gastrointestinal cancer in a subject, methods for treating a subject afflicted with gastrointestinal cancer, and methods of selecting a compound capable of modulating the aggressiveness of a gastrointestinal cancer cell.

Although the alteration of the amount of tyrosine phosphorylated Shc (PY-Shc) and/or p66-Shc, and/or the alteration of a Shc mathematical relationship described herein was identified in gastric and/or colon cancer samples, the methods of the invention are in no way limited to use for the prognosis, diagnosis, characterization, therapy and prevention of gastric and/or colon cancer, e.g., the methods of the invention may be applied to any cancer as described herein.

Various aspects of the invention are described in further detail in the following subsections:

I. Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The terms "tumor" or "cancer" are well known in the art and refer to the presence, e.g., in a subject, of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within a subject, or may be non-tumorigenic cancer cells, such as leukemia cells. As used herein, the term "cancer" includes pre-malignant as well as malignant cancers. Cancers include, but are not limited to, gastric cancer, colorectal cancer, skin cancer, e.g. melanomas or basal cell carcinomas, lung cancer, cancers of the head and neck, bronchus cancer, pancreatic cancer, urinary bladder cancer, brain or central nervous system cancer, peripheral nervous system cancer, esophageal cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. In one embodiment, the cancer is gastrointestinal cancer. In another embodiment, the cancer is a sex-hormone independent cancer, e.g., the cancer is not breast cancer, prostate cancer, and/or ovarian cancer.

As used herein, a "tumor cell" or a "cancer cell" is a cancerous cell within, or originating from, a tumor. Tumor or cancer cells are distinct from other, non-cancerous cells present in a tumor, such as vascular cells.

As used herein "gastrointestinal cancer" or "GI cancer" is a cancer of any of the gastrointestinal tract organs or organs of the alimentary canal, i.e., mouth, esophagus, stomach, duodenum, small intestine, large intestine or colon, rectum, and anus. As used herein, the term gastrointestinal cancer also includes cancer of the pancreas, liver, and gallbladder.

The term "gastric cancer" or "gastric neoplasia", also referred to as "stomach cancer", as used herein, includes adenocarcinomas, lymphomas, stromal tumors, squamous cell tumors, adenosquamous carcinomas, carcinoids, and leiomyosarcomas of the stomach. Gastric cancer, as used herein, also refers to tumors that occur in the lining of the stomach (mucosa), tumors that develop in the lower part of the stomach (pylorus), the middle part (body) of the stomach, those that develop in the upper part (cardia) of the stomach, as well as those tumors that develop in more than one part of the stomach. Gastric cancer may be "metastatic" from another source (e.g., colon) or may be "primary" (a tumor of stomach cell origin). For example, gastric cancer can metastasize to the esophagus or the small intestine, and can extend through the stomach wall to nearby lymph nodes and organs (e.g., liver, pancreas, and colon). Gastric cancer can also metastasize to other parts of the body (e.g., lungs, ovaries, bones).

Gastric cancer can be Stage 0-IV. "Stage 0" gastric cancer, also referred to as "carcinoma in situ", is a tumor found only in the inside lining of the mucosal layer of the stomach wall. "Stage I gastric cancer" is divided into "Stage IA" and "Stage IB", depending on where the cancer has spread. In Stage IA, the cancer has spread completely through the mucosal layer of the stomach wall. In Stage IB, the cancer has spread completely through the mucosal layer of the stomach wall and is found in up to 6 lymph nodes near the tumor; or to the muscularis layer of the stomach wall. In "Stage II gastric cancer", cancer has spread completely through the mucosal layer of the stomach wall and is found in 7 to 15 lymph nodes near the tumor; or to the muscularis layer of the stomach wall and is found in up to 6 lymph nodes near the tumor; or to the serosal layer of the stomach wall but not to lymph nodes or other organs. "Stage III gastric cancer" is divided into "Stage IIIA" and "Stage IIIB" depending on where the cancer has spread. Stage IIIA refers to cancer that has spread to the muscularis layer of the stomach wall and is found in 7 to 15 lymph nodes near the tumor; or the serosal layer of the stomach wall and is found in 1 to 6 lymph nodes near the tumor; or organs next to the stomach but not to lymph nodes or other parts of the body. Stage IIIB refers to cancer that has spread to the serosal layer of the stomach wall and is found in 7 to 15 lymph nodes near the tumor. In "Stage IV gastric cancer", cancer has spread to organs next to the stomach and to at least one lymph node; or more than 15 lymph nodes; or other parts of the body.

As used herein, "colon cancer" or "colorectal cancer" refers to a tumor that arises from the inner lining of the large intestine, or colon. Most, if not all, of these cancers develop from colonic polyps. The term "colon cancer" also refers to carcinomas, lymphomas, carcinoid tumors, melanomas, and sarcomas of the colon.

Colorectal cancer can be divided into Stages 0-IV. "Stage 0" colorectal cancer is found only in the innermost lining of the colon or rectum. Carcinoma in situ is another name for Stage 0 colorectal cancer. "Stage I" colorectal cancer refers to a tumor that has grown into the inner wall of the colon or rectum. The tumor has not reached the outer wall of the colon or extended outside the colon. "Dukes' A" is another name for Stage I colorectal cancer. In "Stage II" colorectal cancer, the tumor extends more deeply into or through the wall of the colon or rectum. It may have invaded nearby tissue, but cancer cells have not spread to the lymph nodes. "Dukes' B" is another name for Stage II colorectal cancer. "Stage III" colorectal cancer refers to a tumor that has spread to nearby lymph nodes, but not to other parts of the body. "Dukes' C" is another name for Stage III colorectal cancer. In "Stage IV" colorectal cancer, the tumor has spread to other parts of the body, such as the liver or lungs. "Dukes' D" is another name for Stage IV colorectal cancer.

As used herein, "survival" refers to the continuation of life of a subject which has been treated for cancer. In one embodiment, survival refers to the failure of a tumor to recur. As used herein, the terms "recur" or "recurrence" refer to the regrowth of a tumor or cancerous cells in a subject in whom primary treatment for the tumor has been administered. The tumor may recur in the original site or in another part of the body. In one embodiment a tumor that recurs is of the same type as the original tumor for which the subject was treated. For example, if a subject had a gastric tumor, was treated and subsequently developed another gastric tumor, the tumor has recurred. In addition, a cancer can recur in a different organ or tissue than the one where it originally occurred. For example, if a subject had a gastric tumor, was treated and subsequently developed a colon tumor, the tumor has also recurred.

As used herein, the term "aggressive", with respect to a tumor or a cancer cell, refers to a tumor having a predisposition to recur in a subject, or a cell derived from such an aggressive tumor.

As used herein, the term "amount", with respect to either p66-Shc or phosphorylated-Shc (PY-Shc) present in a cell or sample refers to either (a) an absolute amount as measured in molecules, moles or weight per unit volume or cell or (b) a relative amount as designated, for example, by a numerical rating from 0 to 5.

As used herein, the term "Shc mathematical relationship" includes any mathematical transformation and/or any mathematical interaction of the amounts of tyrosine phosphorylated Shc (PY-Shc) and/or p66-Shc, e.g., the amounts of PY-Shc and/or p66-Shc, present in a cell or sample. A mathematical transformation of the amounts of tyrosine phosphorylated Shc (PY-Shc) and/or p66-Shc refers to any transformation of the numerical amounts of tyrosine phosphorylated Shc (PY-Shc) and/or p66-Shc such that the methods of the invention are facilitated and includes, but is not limited to, the square root of the amount, the $\log_n$ of the amount, wherein n is any appropriate base, the natural log (ln) of the amount, the amount raised to a power n, wherein n is any integer or a fraction, multiplication of the amount by any number (integer or fraction), and/or the addition or subtraction of any number (integer or fraction) to the amount. A mathematical interaction of the amounts of tyrosine phosphorylated Shc (PY-Shc) and/or p66-Shc refers to any interaction of the numerical amounts of tyrosine phosphorylated Shc (PY-Shc) and p66-Shc such that the methods of the invention are facilitated and includes, but is not limited to, the product of the amount of tyrosine phosphorylated Shc (PY-Shc) and the amount of p66-Shc (referred to herein as the "PYp66-Shc product"), the direct ratio of the amount of tyrosine phosphorylated Shc (PY-Shc) and the amount of p66-Shc (referred to herein as the "Shc ratio"), a weighted average of the amount of tyrosine phosphorylated Shc (PY-Shc) and the amount of p66-Shc, and/or the ratios of polynomial expressions involving the amount of tyrosine phosphorylated Shc (PY-Shc) and the amount of p66-Shc.

The amount of tyrosine phosphorylated Shc (PY-Shc) and/or p66-Shc, and/or a Shc mathematical relationship, in a cell or a sample derived from a subject is "altered" ("increased or decreased" or "higher or lower" than the normal amount of tyrosine phosphorylated Shc (PY-Shc) and/or p66-Shc), and/or a normal Shc mathematical relationship, if the amount of tyrosine phosphorylated Shc (PY-Shc) and/or p66-Shc, and/or the Shc mathematical relationship, is greater or less, respectively, than the control amount, and/or the control Shc mathematical relationship by an amount that is greater than the standard error of the assay employed to assess the amount. The amount of tyrosine phosphorylated Shc (PY-Shc) and/or p66-Shc, and/or the Shc mathematical relationship, in a cell or a sample derived from a subject can be considered "higher" or "lower" than the control amount, and/or the control Shc mathematical relationship if the difference in the control amount, and/or the control Shc mathematical relationship and the sample amount, and/or the Shc mathematical relationship is at least about two, and preferably at least about three, four, or five times, higher or lower, respectively, than the standard error of control and sample measurements of the tyrosine phosphorylated Shc (PY-Shc) and/or p66-Shc, and/or the Shc mathematical relationship.

The term "control amount" of tyrosine phosphorylated Shc (PY-Shc) and/or p66-Shc, as used herein, refers to the amount of tyrosine phosphorylated Shc (PY-Shc) and/or p66-Shc in a cell or a sample derived from a subject not afflicted with cancer, a cell or a sample derived from an aggressive tumor, or a cell or sample derived from a non-aggressive tumor. The "control amount" may, for example, be determined by calculating the average amount of tyrosine phosphorylated Shc (PY-Shc) and/or p66-Shc present in cells or tissues that are known to express tyrosine phosphorylated Shc (PY-Shc) and/or p66-Shc, e.g., express these proteins at high levels, intermediate levels and low levels.

Similarly, the term "control Shc mathematical relationship", as used herein, refers to a mathematical relationship of the amounts of PY-Shc and/or p66 Shc in a cell or a sample derived from a subject not afflicted with cancer, a cell or a sample derived from an aggressive tumor, or a cell or a sample derived from a non-aggressive tumor. The "control Shc mathematical relationship" may, for example, be determined by calculating the average mathematical relationship of the amounts of PY-Shc and/or p66 Shc present in cells or tissues that are known to express tyrosine phosphorylated Shc (PY-Shc) and/or p66-Shc, e.g., express these proteins at high levels, intermediate levels and low levels.

A "higher level of expression and/or activity" of a tyrosine phosphorylated Shc (PY-Shc) and/or p66-Shc refers to an expression level and/or activity in a test sample that is greater than the standard error of the assay employed to assess expression and/or activity, and is preferably at least twice, and more preferably three, four, five or ten or more times the expression level and/or activity of tyrosine phosphorylated Shc (PY-Shc) and/or p66-Shc in a control sample (e.g., a sample from a healthy subject not afflicted with cancer) and preferably, the average expression level and/or activity of tyrosine phosphorylated Shc (PY-Shc) and/or p66-Shc in several control samples.

A "lower level of expression and/or activity" of tyrosine phosphorylated Shc (PY-Shc) and/or p66-Shc refers to an expression level and/or activity in a test sample that is greater than the standard error of the assay employed to assess expression and/or activity, but is preferably at least twice, and more preferably three, four, five or ten or more times less than the expression level of tyrosine phosphorylated Shc (PY-Shc) and/or p66-Shc in a control sample (e.g., a sample that has been calibrated directly or indirectly against a panel of gastrointestinal or breast cancers with follow-up information which serve as a validation standard for prognostic ability of the Shc proteins) and preferably, the average expression level and/or activity of tyrosine phosphorylated Shc (PY-Shc) and/or p66-Shc in several control samples.

As used herein, "antibody" includes, by way of example, naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

As used herein, "known standard" or "control" refers to one or more of an amount and/or mathematical relationship, as applicable, with regard to p66-Shc phosphorylated Shc, and the presence or absence of mutated TP53. A known standard preferably reflects such amount and/or mathematical relationship characteristic of a recurrent tumor and a non-recurrent tumor and/or an aggressive or a non-aggressive tumor. Reagents for generating a known standard include, without limitation, tumor cells from a tumor known to be aggressive, tumor cells from a tumor known to be non-aggressive, and optionally labeled antibodies. Known standards may also include tissue culture cell lines (including, but not limited to, cell lines that have been manipulated to express specific Shc proteins, to not express specific Shc proteins, to express tyrosine kinases, or to express growth factors; or tumor xenografts that either constitutively contain constant amounts of PY-Shc or p66 Shc, or can be manipulated (e.g., by exposure to a changed environment, where such changed environment may include but not limited to growth factors, hormones, steroids, cytokines, antibodies, various drugs and anti-metabolites, and extracellular matrices) to express PY-Shc and/or p66-Shc. Cell lines may be mounted directly on glass slides for analysis, fixed, embedded in paraffin directly as a pellet, or suspended in a matrix such as agarose, then fixed, embedded in paraffin, sectioned and processed as tissue samples. The standards must be calibrated directly or indirectly against a panel of gastrointestinal or breast cancers with follow-up information which serve as a validation standard for prognostic ability of the Shc proteins.

"P66-Shc" refers to the 66 kD isoform of the adaptor protein designated "Shc".

"Phosphorylated Shc" refers to the adaptor protein designated "ShcA" having at least one of its amino acid residue side chains phosphorylated. In one embodiment, a tyrosine residue of Shc is phosphorylated ("tyrosine phosphorylated Shc"). Such residues include, for example, tyrosine residue 317. In another embodiment, a tyrosine residue of Shc is phosphorylated ("tyrosine phosphorylated Shc") where such residues include, for example, tyrosine residue 239, 240. Note that the residue numbers cited above refer to the position of these amino acids in the human Shc 52-kDa isoform of the protein. Tyrosine amino acids 349, 350 and 427 of the human Shc 66-kDa isoform (p66-Shc), correspond to 239, 240, and 317, respectively of the 52-kDa isoform (p52-Shc).

The ShcA gene gives rise to the three isoforms of human Shc designated P46-Shc, p52-Shc and p66-Shc which differ in their N-termini. The nucleotide and amino acid sequence of human Shc are known and can be found in, for example, GenBank accession gi:34147725 (NM_003029.3) SEQ ID NO:1 for p52-Shc nucleotides; or gi:32261324 (NP 003020.2) SEQ ID NO:2 for p52-Shc protein and gi:52693920 (NM_183001.3) SEQ ID NO:3 for p66-Shc nucleotides; and gi:52693921 (NP_892113.3) SEQ ID NO:4 for the p66-Shc protein), the contents of each of which are incorporated in their entirety by this reference.

As used herein, "TP53" refers to the tumor suppressor protein p53 involved in the regulation of cell proliferation, which is well known in the art. The nucleotide and amino acid sequence of human TP53 are known and can be found in, for example, GenBank accession gi:8400737 and gi:8400738.

As used herein, the term "mutated TP53" refers to a TP53 protein that has a genetic mutation or deletion that alters the biological activity of the protein, e.g., a mutation which may, for example, block TP53 expression or produce a functionally inactive TP53. The term "mutated TP53" also encompasses a dysregulated TP53 protein, e.g., a TP53 protein whose biological activity or expression has been down-regulated by mutations or deletions in other proteins or genes, for example, mutations in PI3'Kinase or PTEN. In all of the foregoing embodiments, the resulting protein is a TP53 protein that is not antigenically recognizable as TP53.

"Primary treatment" as used herein, refers to the initial treatment of a subject afflicted with a tumor. Primary treatments include, without limitation, surgery, radiation, hormone therapy, chemotherapy, immunotherapy, angiogenic therapy, and therapy via biomodulators.

As used herein, a "subject" is any animal, such as a mammal, and includes, without limitation, humans, mice, monkeys, dogs, cats, mice, rats cows, horses, goats, sheep as well as other farm and pet animals Cancer is "treated" if at least one symptom of the cancer is expected to be or is alleviated, terminated, slowed, or prevented. As used herein, cancer is also "treated" if recurrence or metastasis of the cancer is reduced, slowed, delayed, or prevented.

A kit is any manufacture (e.g. a package or container) comprising at least one reagent, e.g. a probe, for specifically detecting tyrosine phosphorylated Shc (PY-Shc) and/or p66-Shc, the manufacture being promoted, distributed, or sold as a unit for performing the methods of the present invention.

II. Uses of the Invention

The invention provides methods for prognosing cancer recurrence in a subject being treated for cancer, e.g., gastrointestinal cancer, e.g., gastric cancer or colon cancer. These methods comprise determining the amount of tyrosine phosphorylated Shc (PY-Shc) and/or p66-Shc present in a sample derived from a subject and comparing that amount to a control amount of tyrosine phosphorylated Shc (PY-Shc) and/or p66-Shc. The invention also provides a method for prognosing survival of a subject being treated for cancer, e.g., gastrointestinal cancer, by determining the amount of tyrosine phosphorylated Shc (PY-Shc) and/or p66-Shc present in a sample obtained from the subject; and comparing that amount to a control amount of tyrosine phosphorylated Shc (PY-Shc) and/or p66-Shc.

The present invention also provides methods for prognosing cancer recurrence in a subject being treated for cancer, e.g., gastrointestinal cancer, such as gastric cancer or colon cancer by obtaining a gastrointestinal tissue sample from a subject; contacting the gastrointestinal tissue sample with an antibody that specifically binds to tyrosine phosphorylated Shc (PY-Shc) and/or p66-Shc in the sample; determining the amount of tyrosine phosphorylated Shc (PY-Shc) and/or p66-Shc in the sample using the foregoing antibodies and an immunohistochemical assay; comparing the amount of tyrosine phosphorylated Shc (PY-Shc) and/or p66-Shc in a sample to a control amount of tyrosine phosphorylated Shc (PY-Shc) and/or p66-Shc present in a control sample, wherein a decreased amount of tyrosine phosphorylated Shc (PY-Shc) and/or an increased amount of p66-Shc in the sample relative to the amount in the control sample indicates that the cancer will recur in the subject, and an increased amount of tyrosine phosphorylated Shc (PY-Shc) and/or a decreased amount of p66-Shc in the sample relative to the amount in the control sample indicates that the cancer will not recur in the subject.

The methods of the present invention can be practiced in conjunction with any other method used by the skilled practitioner to prognose the recurrence of cancer and/or the survival of a subject being treated for cancer. For example, the methods of the invention may be performed in conjunction with a morphological or cytological analysis of the sample obtained from the subject. Cytological methods would include immunohistochemical or immunofluorescence detection (and quantitation if appropriate) of any other molecular marker either by itself, in conjunction with other markers, and/or in conjunction with the Shc markers. Other methods would include detection of other markers by in situ PCR, or by extracting tissue and quantitating other markers by real time PCR. PCR is defined as polymerase chain reaction.

In one embodiment of the invention, only the amount of p66-Shc is determined. In another embodiment, only the amount of tyrosine phosphorylated Shc (PY-Shc) is determined. In yet another embodiment, the amounts of both p66-Shc and tyrosine phosphorylated Shc (PY-Shc) are determined. In another embodiment, a Shc mathematical relationship is determined. In one embodiment, the Shc mathematical relationship that is determined is the Shc ratio. In another embodiment, the Shc mathematical relationship that is determined is the PYp66-Shc product. When both the amounts of p66-Shc and tyrosine phosphorylated Shc (PY-Shc) are determined, and/or a Shc mathematical relationship is determined, in the kits and methods of the invention, the amount can be compared with the normal amount in control samples of the same type either in a single reaction mixture (i.e., using reagents, such as different fluorescent probes) or in separate reaction mixtures.

In general, it is preferable that the difference between the amount of tyrosine phosphorylated Shc (PY-Shc) and/or p66-Shc, and/or the Shc mathematical relationship in a sample from a subject being treated for cancer and the amount of tyrosine phosphorylated Shc (PY-Shc) and/or p66-Shc, and/or the Shc mathematical relationship in control sample, is as great as possible. Although this difference can be as small as the limit of detection of the method for determining the amount and/or mathematical relationship it is preferred that the difference be at least greater than the standard error of the assessment method, and preferably a difference of at least 2-, 3-, 4-, 5-, 6-, 7-, 8-, 9-, 10-, 15-, 20-, 25-, 100-, 500-, 1000-fold or greater than the standard error of the assessment method.

An alteration in the amount of tyrosine phosphorylated Shc (PY-Shc) and/or p66-Shc, and/or the Shc mathematical relationship in control (e.g., non-cancerous) tissue can be assessed in a variety of ways. In one embodiment, the amount is assessed by assessing the amount of tyrosine phosphorylated Shc (PY-Shc) and/or p66-Shc, and/or the Shc mathematical relationship in cells which appear to be non-cancerous and by comparing the foregoing normal amount of tyrosine phosphorylated Shc (PY-Shc) and/or p66-Shc and/or the normal Shc mathematical relationship with the amount and/or the Shc mathematical relationship in the cells which are suspected of being cancerous. For example, when laparoscopy or other medical procedure, reveals the presence of a tumor on one portion of an organ, the normal amount of tyrosine phosphorylated Shc (PY-Shc) and/or p66-Shc may be assessed using the non-affected portion of the organ, and this normal amount may be compared with the amount of tyrosine phosphorylated Shc (PY-Shc) and/or p66-Shc in an affected portion (i.e., the tumor) of the organ. Alternatively, and particularly as further information becomes available as a result of routine performance of the methods described herein, population-average values for "normal" amount of tyrosine phosphorylated Shc (PY-Shc) and/or p66-Shc, and/or the normal and/or the Shc mathematical relationship may be used. In other embodiments, the "normal" amount of tyrosine phosphorylated Shc (PY-Shc) and/or p66-Shc, and/or the "normal" Shc mathematical relationship may be determined by assessing amount of tyrosine phosphorylated Shc (PY-Shc) and/or p66-Shc in a subject sample obtained from a non-cancer-afflicted subject, from a subject sample obtained from a subject before the suspected onset of cancer in the subject, from archived subject samples, and the like. In the preferred embodiment, the amount of tyrosine phosphorylated Shc (PY-Shc) and/or p66-Shc, and/or the Shc mathematical relationship is determined as described above.

Methods for assessing the efficacy of a treatment regimen, e.g., chemotherapy, radiation therapy, surgery, hormone therapy, or any other therapeutic approach useful for treating cancer in a subject are also provided. In these methods the amount of tyrosine phosphorylated Shc (PY-Shc) and/or p66-Shc in a pair of samples (a first sample not subjected to the treatment regimen and a second sample subjected to at least a portion of the treatment regimen) is assessed. A lower amount of tyrosine phosphorylated Shc (PY-Shc) in the first sample, relative to the second sample, is an indication that the treatment regimen is efficacious for treating cancer. A higher amount of p66-Shc present in the first sample, relative to the second sample would also be an indication that the treatment regimen is efficacious for treating gastrointestinal cancer in the subject. Similarly, a Shc mathematical relationship, e.g., the Shc ratio, in a pair of samples (a first sample not subjected to the treatment regimen and a second sample subjected to at least a portion of the treatment regimen) is assessed. A higher Shc ratio in the second sample, relative to the first sample, is an indication that the treatment regimen is efficacious for treating cancer, e.g., colon cancer, in the subject. A lower Shc ratio present in the second sample, relative to the first sample would be an indication that the treatment regimen is not efficacious for treating cancer, e.g., colon cancer, in the subject. The Shc mathematical relationship, e.g., the PYp66-Shc product, in a pair of samples (a first sample not subjected to the treatment regimen and a second sample subjected to at least a portion of the treatment regimen) may also be assessed. A lower PYp66-Shc product in the second sample, relative to the first sample, is an indication that the treatment regimen is efficacious for treating cancer, e.g., colon cancer, in the subject. A higher PYp66-Shc product present in the second sample, relative to the first sample would be an indication that the treatment regimen is not efficacious for treating cancer, e.g., colon cancer, in the subject.

The invention also provides a method for determining whether a gastrointestinal cancer cell is aggressive. The method comprises determining the amount of phosphorylated Shc (PY-Shc) and/or p66-Shc present in a cell and comparing the amount to a control amount of phosphorylated Shc (PY-Shc) and/or p66-Shc present in a control sample, defined in Definitions, thereby determining whether a gastrointestinal cancer cell is aggressive.

The methods of the invention may also be used to select a compound that is capable of modulating, i.e., decreasing, the aggressiveness of a gastrointestinal cancer cell. In this method, a gastrointestinal cancer cell is contacted with a test compound, and the ability of the test compound to modulate the expression and/or activity of phosphorylated Shc (PY-Shc) and/or p66-Shc in the gastrointestinal cancer cell is determined, thereby selecting a compound that is capable of modulating aggressiveness of a gastrointestinal cancer cell.

Using the methods described herein, a variety of molecules, particularly including molecules sufficiently small to be able to cross the cell membrane, may be screened in order to identify molecules which modulate, e.g., increase the expression and/or activity of tyrosine phosphorylated Shc (PY-Shc). Compounds so identified can be provided to a subject in order to inhibit the aggressiveness of cancer cells in the subject, to prevent the recurrence of cancer in the subject, or to treat cancer in the subject.

Accordingly, the invention also includes methods for treating a subject afflicted with cancer, e.g., gastrointestinal cancer, as described in Section V below.

Agents or modulators which have a stimulatory or inhibitory effect on the amount and/or activity of tyrosine phosphorylated Shc (PY-Shc) and/or p66-Shc can be administered to a subject (prophylactically or therapeutically) to treat cancer, e.g., gastrointestinal cancer, in the subject. In conjunction with such treatment, the pharmacoproteomics and pharmacophosphoproteomics (i.e., the study of the relationship between a tumor's proteome/phosphoproteome and that tumor's response to a foreign compound or drug) of the tumor may be considered. Differences in tumor milieu (including growth factors, extracellular contacts, activation of tumor oncogenes or inactivation of tumor suppressor genes, etc.) can lead to therapeutic failure if the molecular mechanisms (proteome and phosphoproteome) are not suitable for the action of the pharmacologically active drug. Thus, the pharmacoproteome and pharmacophosphoproteome of the tumor permits the selection of effective agents (e.g., drugs) for prophylactic or therapeutic treatments based on a consideration of the individual tumor's proteome and phosphoproteome. Such pharmacoproteomics and pharmacophosphoproteomics can further be used to determine appropriate dosages and therapeutic regimens. Accordingly, the amount and/or activity of tyrosine phosphorylated Shc (PY-Shc) and/or p66-Shc in a subject can be determined to thereby select appropriate agent(s) for therapeutic or prophylactic treatment of the subject. Examples include, but are not limited to, agents directed at growth-factor receptors (monoclonal antibodies and their recombinant derivatives such as Herceptin, Erbitux; tyrosine kinase inhibitors such as Gefitinib), hormone receptors (tamoxifen and other SERMS; aromatase inhibitors), intracellular tyrosine kinases such as SRC-family members, serine/threonine kinases, protein tyrosine phosphatases and protein serine/threonine phosphatases.

The present invention also provides a method for prognosing cancer recurrence in a subject being treated for cancer. The method involves determining the presence or absence of mutated TP53 in the sample derived from said subject, determining the amount of tyrosine phosphorylated Shc (PY-Shc) and/or p66-Shc present in the sample derived from the subject; comparing the presence or absence of the mutated TP53 to the presence or absence of mutated TP53 present in a control sample, and comparing the amount of tyrosine phosphorylated Shc (PY-Shc) and/or p66-Shc to a control amount of tyrosine phosphorylated Shc (PY-Shc) and/or p66-Shc present in a control sample, thereby prognosing cancer recurrence in the subject being treated for cancer.

In one embodiment, an increased amount of p66-Shc and the presence of mutated TP53 in the sample indicates that the cancer will recur in the subject. In another embodiment, an increased amount of p66-Shc and the absence of mutated TP53 in the sample indicates that the cancer will not recur in the subject III. Methods for Obtaining Samples and Detecting/Quantitating Tyrosine Phosphorylated Shc (PY-Shc) and/or p66-Shc Levels, and/or a Shc Mathematical Relationship Samples useful in the methods of the invention include any tissue, cell, biopsy, or bodily fluid sample that expresses tyrosine phosphorylated Shc (PY-Shc) and/or p66-Shc. In one embodiment, a sample may be a tissue, a cell, whole blood, serum, plasma, buccal scrape, saliva, cerebrospinal fluid, urine, stool, or bronchoalveolar lavage. In preferred embodiments, the tissue sample is a gastric tissue sample, a small intestine tissue sample, a large intestine tissue sample.

Body samples may be obtained from a subject by a variety of techniques known in the art including, for example, by the use of a biopsy or by scraping or swabbing an area or by using a needle to aspirate bodily fluids. Methods for collecting various body samples are well known in the art. In particular embodiments, the body sample comprises gastrointestinal tissue samples.

Tissue samples suitable for detecting and quantitating the PY-Shc and/or p66-Shc proteins may be fresh, frozen, or fixed according to methods known to one of skill in the art. Suitable tissue samples are preferably sectioned and placed on a microscope slide for further analyses. Alternatively, solid samples, i.e., tissue samples, may be solubilized and/or homogenized and subsequently analyzed as soluble extracts.

In one embodiment, a freshly obtained biopsy sample is frozen using, for example, liquid nitrogen or difluorodichloromethane. The frozen sample is mounted for sectioning using, for example, OCT, and serially sectioned in a cryostat. The serial sections are collected on a glass microscope slide. For immunohistochemical staining the slides may be coated with, for example, chrome-alum, gelatine or poly-L-lysine to ensure that the sections stick to the slides. In another embodiment, samples are fixed and embedded prior to sectioning. For example, a tissue sample may be fixed in, for example, formalin, serially dehydrated and embedded in, for example, paraffin.

Once the sample is obtained any method known in the art to be suitable for detecting and quantitating the PY-Shc and/or p66-Shc and/or TP53 proteins may be used (either at the nucleic acid or, preferably, at the protein level). Such methods are well known in the art and include but are not limited to western blots, northern blots, southern blots, immunohistochemistry, ELISA, e.g., amplified ELISA, immunoprecipitation, immunofluorescence, flow cytometry, immunocytochemistry, mass spectrometrometric analyses, e.g., MALDI-TOF and SELDI-TOF, nucleic acid hybridization techniques, nucleic acid reverse transcription methods, and nucleic acid amplification methods. In particular embodiments, the expression of the PY-Shc and/or p66-Shc proteins is detected on a protein level using, for example, antibodies that specifically bind these proteins, such as the ones described in, for example, U.S. Publication No. 2004/0033542 and 2005/0004008, the entire contents of each of which are incorporated herein by reference. In other embodiments, the presence or absence of TP53 is determined using, for example an antibody that binds to this protein, such as, for example, the DO-7 antibody which recognizes an epitope between amino acids 21-25 or TP53 (Vojtesek, et al. (1992) *J Immunol Meth* 151:237) or Pab240 which recognizes a conformation dependent epitope of TP53 (Legros, et al. (1994) *Oncogene* 9:3689; Vojtesek, et al. (1995) *Oncogene* 10:389).

Samples may need to be modified in order to make the PY-Shc and/or p66-Shc and/or TP53 proteins accessible to antibody binding. In a particular aspect of the immunocytochemistry or immunohistochemistry methods, slides may be transferred to a pretreatment buffer and optionally heated to increase antigen accessibility. Heating of the sample in the pretreatment buffer rapidly disrupts the lipid bi-layer of the cells and makes the antigens (may be the case in fresh specimens, but not typically what occurs in fixed specimens) (i.e., the PY-Shc and/or p66-Shc proteins and/or TP53) more accessible for antibody binding. The terms "pretreatment buffer" and "preparation buffer" are used interchangeably herein to refer to a buffer that is used to prepare cytology or histology samples for immunostaining, particularly by increasing PY-Shc and/or p66-Shc, and/or TP53 protein accessibility for antibody binding. The pretreatment buffer may comprise a pH-specific salt solution, a polymer, a detergent, or a nonionic or anionic surfactant such as, for example, an ethyloxylated anionic or nonionic surfactant, an alkanoate or an alkoxylate or even blends of these surfactants or even the use of a bile salt. The pretreatment buffer may, for example, be a solution of 0.1% to 1% of deoxycholic acid, sodium salt, or a solution of sodium laureth-13-carboxylate (e.g., Sandopan LS) or and ethoxylated anionic complex. In some embodiments, the pretreatment buffer may also be used as a slide storage buffer.

Any method for making PY-Shc and/or p66-Shc, and/or TP53 proteins more accessible for antibody binding may be used in the practice of the invention, including the antigen retrieval methods known in the art. See, for example, Bibbo, et al. (2002) *Acta. Cytol.* 46:25-29; Saqi, et al. (2003) *Diagn. Cytopathol.* 27:365-370; Bibbo, et al. (2003) *Anal. Quant. Cytol. Histol.* 25:8-11, the entire contents of each of which are incorporated herein by reference.

Following pretreatment to increase PY-Shc, p66-Shc, and/or TP53 protein accessibility, samples may be blocked using an appropriate blocking agent, e.g., a peroxidase blocking reagent such as hydrogen peroxide. In some embodiments, the samples may be blocked using a protein blocking reagent to prevent non-specific binding of the antibody. The protein blocking reagent may comprise, for example, purified casein. An antibody, particularly a monoclonal or polyclonal antibody that specifically binds to PY-Shc and/or p66-Shc or a monoclonal or polyclonal antibody that specifically binds to TP53 is then incubated with the sample. One of skill in the art will appreciate that a more accurate prognosis or diagnosis may be obtained in some cases by detecting both PY-Shc and p66-Shc in a patient sample. Therefore, in particular embodiments, at least two antibodies directed to each of PY-Shc and p66-Shc are used. Where more than one antibody is used, these antibodies may be added to a single sample sequentially as individual antibody reagents or simultaneously as an antibody cocktail. Alternatively, each individual antibody may be added to a separate sample from the same patient, and the resulting data pooled.

Techniques for detecting antibody binding are well known in the art. Antibody binding to PY-Shc, p66-Shc, and/or TP53 maybe detected through the use of chemical reagents that generate a detectable signal that corresponds to the level of antibody binding and, accordingly, to the level of PY-Shc, p66-Shc, and/or TP53 protein expression. In one of the immunohistochemistry or immunocytochemistry methods of the invention, antibody binding is detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell staining that corresponds to expression level of the biomarker of interest. Enzymes of particular interest include, but are not limited to, horseradish peroxidase (HRP) and alkaline phosphatase (AP).

In one particular immunohistochemistry or immunocytochemistry method of the invention, antibody binding to the PY-Shc and/or p66-Shc proteins is detected through the use of an HRP-labeled polymer that is conjugated to a secondary antibody. Antibody binding can also be detected through the use of a species-specific probe reagent, which binds to monoclonal or polyclonal antibodies, and a polymer conjugated to HRP, which binds to the species specific probe reagent. Slides are stained for antibody binding using any chromagen, e.g., the chromagen 3,3-diaminobenzidine (DAB), and then counterstained with hematoxylin and, optionally, a bluing agent such as ammonium hydroxide or TBS/Tween-20. Other suitable chromagens include, for example, 3-amino-9-ethylcarbazole (AEC). In some aspects of the invention, slides are reviewed microscopically by a cytotechnologist and/or a pathologist to assess cell staining, e.g., fluorescent staining (i.e., PY-Shc or p66-Shc expression). Alternatively, samples may be reviewed via automated microscopy or by personnel with the assistance of computer software that facilitates the identification of positive staining cells.

Detection of antibody binding can be facilitated by coupling the anti-PY-Shc, p66-Shc, and/or TP53 antibodies to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, $^{14}C$, or $^{3}H$.

In one embodiment of the invention frozen samples are prepared as described above and subsequently stained with antibodies against PY-Shc and/or p66-Shc diluted to an appropriate concentration using, for example, Tris-buffered saline (TBS). Primary antibodies can be detected by incubating the slides in biotinylated anti-immunoglobulin. This signal can optionally be amplified and visualized using diaminobenzidine precipitation of the antigen. Furthermore, slides can be optionally counterstained with, for example, hematoxylin, to visualize the cells.

In another embodiment, fixed and embedded samples are stained with antibodies against PY-Shc and/or p66-Shc, and/or TP53 and counterstained as described above for frozen sections. In addition, samples may be optionally treated with agents to amplify the signal in order to visualize antibody staining. For example, a peroxidase-catalyzed deposition of biotinyl-tyramide, which in turn is reacted with peroxidase-conjugated streptavidin (Catalyzed Signal Amplification (CSA) System, DAKO, Carpinteria, Calif.) may be used.

Tissue-based assays (i.e., immunohistochemistry) are the preferred methods of detecting and quantitating PY-Shc and/or p66-Shc and/or TP53. In one embodiment, the presence or absence of mutated TP53 may be determined by immunohistochemistry. In one embodiment, the TP53 immunohistochemical analysis uses low concentrations of anti-TP53 antibody (e.g., DO-7) such that cells lacking mutated TP53 do not stain. In another embodiment, the presence or absence of mutated TP53 is determined using an immunohistochemical method that uses high concentrations of an anti-TP53 antibody (e.g., DO-7) such that cells lacking mutated TP53 protein stain heavily. Cells that do not stain contain either mutated TP53 and fail to produce antigenically recognizable TP53 protein, or are cells in which the pathways that regulate TP53 levels are dysregulated (for example, by activating mutations in PI3'Kinase or inactivating mutations in the lipid phosphatase, PTEN), resulting in steady state expression of negligible TP53 protein.

One of skill in the art will recognize that the concentration of a particular antibody used to practice the methods of the invention will vary depending on such factors as time for binding, level of specificity of the antibody for PY-Shc and/or p66-Shc and/or TP53, and method of sample preparation. Moreover, when multiple antibodies are used, the required concentration may be affected by the order in which the antibodies are applied to the sample, e.g., simultaneously as a cocktail or sequentially as individual antibody reagents. Furthermore, the detection chemistry used to visualize antibody binding to PY-Shc and/or p66-Shc and/or TP53 must also be optimized to produce the desired signal to noise ratio.

In one embodiment of the invention, proteomic methods, e.g., mass spectrometry, are used for detecting and quantitating the PY-Shc and/or p66-Shc and/or TP53 proteins. For example, matrix-associated laser desorption/ionization timeof-flight mass spectrometry (MALDI-TOF MS) or surface-enhanced laser desorption/ionization time-of-flight mass spectrometry (SELDI-TOF MS) which involves the application of a biological sample, such as serum, to a protein-binding chip (Wright, G. L., Jr., et al. (2002) *Expert Rev Mol Diagn* 2:549; Li, J., et al. (2002) *Clin Chem* 48:1296; Laronga, C., et al. (2003) *Dis Markers* 19:229; Petricoin, E. F., et al. (2002) 359:572; Adam, B. L., et al. (2002) *Cancer Res* 62:3609; Tolson, J., et al. (2004) *Lab Invest* 84:845; Xiao, Z., et al. (2001) *Cancer Res* 61:6029) can be used to detect and quantitate the PY-Shc and/or p66-Shc proteins. Mass spectrometric methods are described in, for example, U.S. Pat. Nos. 5,622,824, 5,605,798 and 5,547,835, the entire contents of each of which are incorporated herein by reference.

In other embodiments, the expression of p66-Shc is detected at the nucleic acid level. In yet other embodiments, the presence or absence of TP53 is determined at the nucleic acid level. Nucleic acid-based techniques for assessing expression are well known in the art and include, for example, determining the level of p66-Shc mRNA and/or TP53 mRNA in a body sample. Many expression detection methods use isolated RNA. Any RNA isolation technique that does not select against the isolation of mRNA can be utilized for the purification of RNA from cells that express p66-Shc and/or TP53 (see, e.g., Ausubel et al., ed., (1987-1999) Current Protocols in Molecular Biology (John Wiley & Sons, New York). Additionally, large numbers of tissue samples can readily be processed using techniques well known to those of skill in the art, such as, for example, the single-step RNA isolation process of Chomczynski (1989, U.S. Pat. No. 4,843, 155).

The term "probe" refers to any molecule that is capable of selectively binding to PY-Shc and/or p66-Shc and/or TP53, for example, a p66-Shc and/or TP53 nucleotide transcript or PY-Shc and/or p66-Shc and/or TP53 protein. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the p66-Shc mRNA. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to p66-Shc mRNA or p66-Shc genomic DNA.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in detecting the level of PY-Shc and/or p66-Shc and/or TP53 mRNA.

An alternative method for determining the level of p66-Shc and/or TP53 mRNA in a sample involves the process of nucleic acid amplification, e.g., by RT-PCR (the experimental embodiment set forth in Mullis, 1987, U.S. Pat. No. 4,683, 202), ligase chain reaction (Barany (1991) Proc. Natl. Acad. ScL USA 88:189-193), self sustained sequence replication (Guatelli et al. (1990) Proc. Natl. Acad. ScL USA 87: 1874-1878), transcriptional amplification system (Kwoh et al. (1989) Proc. Natl. Acad. ScL USA 86:1173-1177), Q-Beta Replicase (Lizardi et al. (1988) Bio/Technology 6:1197), rolling circle replication (Lizardi et al., U.S. Pat. No. 5,854, 033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, p66-Shc and/or TP53 expression is assessed by quantitative fluorogenic RT-PCR (i.e., the TAQMAN™ System). Such methods typically utilize pairs of oligonucleotide primers that are specific for p66-Shc. Methods for designing oligonucleotide primers specific for a known sequence are well known in the art.

The expression levels of p66-Shc and/or TP53 mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of p66-Shc and/or TP53 expression may also comprise using nucleic acid probes in solution.

In one embodiment of the invention, microarrays are used to detect p66-Shc and/or TP53 expression. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

The amounts of tyrosine phosphorylated Shc (PY-Shc) and/or p66-Shc, and/or a mathematical relationship of the amounts of PY-Shc and/or p66 Shc may be used to calculate the risk of cancer recurrence in a subject being treated for cancer, the survival of a subject being treated for cancer, whether a cancer cell is aggressive, the efficacy of a treatment regimen for treating cancer, and the like, using the methods of the invention, which may include methods of regression analysis known to one of skill in the art. For example, suitable regression models include, but are not limited to CART (e.g., Hill, T, and Lewicki, P. (2006) "STATISTICS Methods and Applications" StatSoft, Tulsa, OK), Cox, exponential, normal and log normal, logistic, parametric, non-parametric, semi-parametric, linear, or additive.

In one embodiment, a regression analysis includes the amounts of tyrosine phosphorylated Shc (PY-Shc) and/or p66-Shc. In another embodiment, a regression analysis includes a Shc mathematical relationship. In yet another embodiment, a regression analysis of the amounts of tyrosine phosphorylated Shc (PY-Shc) and/or p66-Shc, and/or a Shc mathematical relationship may include additional clinical and/or molecular co-variates. Such clinical co-variates include, but are not limited to, nodal status, tumor stage, tumor grade, tumor size, treatment regime, e.g., chemotherapy and/or radiation therapy, clinical outcome (e.g., relapse, disease-specific survival, therapy failure), and/or clinical outcome as a function of time after diagnosis, time after initiation of therapy, and/or time after completion of treatment. Molecular co-variates can include, but are not limited to additional molecular maker values, e.g., TP53, PSA, BRCA1, BRCA2, HER, and the like.

In another embodiment, the amounts of tyrosine phosphorylated Shc (PY-Shc) and/or p66-Shc, and/or a mathematical relationship of the amounts of PY-Shc and/or p66 Shc and the presence or absence or mutated TP53 may be used to calculate the risk of cancer recurrence in a subject being treated for cancer, the survival of a subject being treated for cancer, whether a cancer cell is aggressive, the efficacy of a treatment regimen for treating cancer, and the like, using the methods of the invention, which may include methods of regression analysis known to one of skill in the art. For example, suitable regression models include, but are not limited to CART (e.g., Hill, T, and Lewicki, P. (2006) "STATISTICS Methods and Applications" StatSoft, Tulsa, OK), Cox exponential, normal and log normal, logistic, parametric, non-parametric, semi-parametric, linear or additive.

In one embodiment, a regression analysis includes the amounts of tyrosine phosphorylated Shc (PY-Shc) and/or p66-Shc. In another embodiment, a regression analysis includes a Shc mathematical relationship. In yet another embodiment, a regression analysis of the amounts of tyrosine phosphorylated Shc (PY-Shc) and/or p66-Shc, and/or a Shc mathematical relationship and/or the presence or absence or mutated TP53 may include additional clinical and/or molecular co-variates. Such clinical co-variates include, but are not limited to, nodal status, tumor stage, tumor grade, tumor size, treatment regime, e.g., chemotherapy and/or radiation therapy, clinical outcome (e.g., relapse, disease-specific survival, therapy failure), and/or clinical outcome as a function of time after diagnosis, time after initiation of therapy, and/or time after completion of treatment. Molecular co-variates can include, but are not limited to additional molecular maker values, e.g., Ki67, Bcl-2, Bcl-xL, phospho-AKT, and the mutational status of Ras, PI3'Kinase, PTEN, and ATM, and the like.

IV. Kits

The invention also provides compositions and kits for prognosing cancer recurrence or survival of a subject being treated for cancer, e.g. gastrointestinal cancer. These kits include one or more of the following: a detectable antibody that specifically binds to p66-Shc, a detectable antibody that specifically binds to tyrosine phosphorylated Shc (PY-Shc), reagents for obtaining and/or preparing gastrointestinal tissue samples for staining, and instructions for use.

The kits of the invention may optionally comprise additional components useful for performing the methods of the invention. By way of example, the kits may comprise fluids (e.g., SSC buffer) suitable for annealing complementary nucleic acids or for binding an antibody with a protein with which it specifically binds, one or more sample compartments, an instructional material which describes performance of a method of the invention and gastrointestinal tissue specific controls/standards.

V. Methods of Treatment

The present invention further provides for both prophylactic and therapeutic methods of treating a subject, e.g., a human, who has or is at risk of (or susceptible to) cancer, e.g., gastrointestinal cancer. As used herein, "treatment" of a subject includes the application or administration of a therapeutic agent to a subject, or application or administration of a therapeutic agent to a cell or tissue from a subject, who has cancer, has a symptom of cancer, or is at risk of (or susceptible to) cancer, with the purpose of curing, inhibiting, healing, alleviating, relieving, altering, remedying, ameliorating, improving, or affecting the cancer, a symptom of the cancer, or the risk of (or susceptibility to) the cancer. As used herein, a "therapeutic agent" or "compound" includes any compound or agent capable of modulating the expression and/or activity of tyrosine phosphorylated Shc (PY-Shc) and/or p66-Shc. Such compounds include, but are not limited to, small molecules, peptides, peptidomimetics, hormones, cytokines, polypeptides, RNA interfering agents, e.g., siRNA molecules, antibodies, ribozymes, and antisense oligonucleotides.

As described herein, recurrence of gastric cancer in a subject and/or death of a subject with gastric cancer correlates with a decreased amount of tyrosine phosphorylated Shc (PY-Shc) and/or an increased amount of p66-Shc. While, as discussed above, some of these changes in the amount of tyrosine phosphorylated Shc (PY-Shc) and/or p66-Shc result from the occurrence of the cancer, these changes may also induce, maintain, and promote the cancerous state. Thus, cancer, e.g., gastric cancer, characterized by a decrease in the amount of tyrosine phosphorylated Shc (PY-Shc) may be treated by increasing the expression and/or activity of tyrosine phosphorylated Shc (PY-Shc).

As described herein, recurrence of colon cancer in a subject and/or death of a subject with colon cancer correlates with an increased amount of p66-Shc and/or a decreased Shc ratio and/or an increased PYp66-Shc product. While, as discussed above, some of these changes result from the occurrence of the cancer, these changes may also induce, maintain, and promote the cancerous state. Thus, cancer, e.g., colon cancer, characterized by an increased amount of p66-Shc and/or a decreased Shc ratio and/or an increased PYp66-Shc product may be treated by decreasing the expression and/or activity of p66-Shc and/or increasing the Shc ratio and/or decreasing the PYp66-Shc product.

Accordingly, another aspect of the invention pertains to methods for treating a subject suffering from cancer, e.g., gastrointestinal cancer. These methods involve administering to a subject a compound capable of increasing the expression and/or activity of PY-Shc in an amount effective to increase the expression and/or activity of PY-Shc. Compounds which may be used to increase the expression and/or activity of tyrosine phosphorylated Shc (PY-Shc) to thereby treat or prevent cancer, include antibodies (e.g., conjugated antibodies), small molecules, RNA interfering agents, e.g., siRNA molecules, ribozymes, and antisense oligonucleotides. Such compounds may, for example, be identified using the screening assays described below.

Another aspect of the invention pertains to methods for treating a subject suffering from cancer, e.g., gastrointestinal cancer. These methods involve administering to a subject a compound capable of decreasing the expression and/or activity of p66-Shc in an amount effective to decrease the expression and/or activity of p66-Shc. Compounds which may be used to decrease the expression and/or activity of p66 Shc to thereby treat or prevent cancer, include antibodies (e.g., conjugated antibodies), hormones, cytokines, growth factors, small molecules, RNA interfering agents, e.g., siRNA molecules, ribozymes, and antisense oligonucleotides. Such compounds may, for example, be identified using the screening assays described below.

In addition, TP53 is known to stabilize p66-Shc, thereby increasing the intracellular level of p66-Shc (Trinei, M. et al. (2002) *Oncogene* 21:3872-3878). Accordingly, recurrence of cancer, e.g., gastric or colon cancer, may be prevented and/or survival of subjects with cancer, e.g., gastric or colon cancer may be promoted by administering to a subject an effective amount of a compound capable of decreasing the expression and/or activity of TP53.

VI. Screening Assays

The invention also provides methods (also referred to herein as "screening assays") for identifying modulators, i.e., candidate or test compounds or agents (e.g., proteins, peptides, peptidomimetics, peptoids, small molecules or other drugs), which modulate the aggressiveness of a cancer cell, e.g., gastrointestinal cancer cell, by modulating the expression and/or activity of tyrosine phosphorylated Shc (PY-Shc) and/or p66-Shc. Such assays typically comprise a reaction between tyrosine phosphorylated Shc (PY-Shc) and/or p66-Shc and one or more assay components. The other components may be either the test compound itself, or a combination of test compounds and a natural binding partner of the tyrosine phosphorylated Shc (PY-Shc) and/or p66-Shc. Compounds identified via assays such as those described herein may be useful, for example, for modulating, e.g., inhibiting, ameliorating, treating, or preventing aggressiveness of a cancer cell, e.g., a gastrointestinal cancer cell, such as a gastric cancer cell.

The test compounds used in the screening assays of the present invention may be obtained from any available source, including systematic libraries of natural and/or synthetic compounds. Test compounds may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Hougliten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89:1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

The screening methods of the invention comprise contacting a cancer cell, e.g., a gastrointestinal cancer cell, with a test compound and determining the ability of the test compound to modulate the expression and/or activity of tyrosine phosphorylated Shc (PY-Shc) and/or p66-Shc in the cell. The expression and/or activity of tyrosine phosphorylated Shc (PY-Shc) and/or p66-Shc can be determined as described herein.

In another embodiment, the invention provides assays for screening candidate or test compounds which are substrates of tyrosine phosphorylated Shc (PY-Shc) and/or p66-Shc or biologically active portions thereof. In yet another embodiment, the invention provides assays for screening candidate or test compounds which bind to tyrosine phosphorylated Shc (PY-Shc) and/or p66-Shc or biologically active portions thereof. Determining the ability of the test compound to directly bind to a marker can be accomplished, for example, by coupling the compound with a radioisotope or enzymatic label such that binding of the compound to the marker can be determined by detecting the labeled marker compound in a complex. For example, compounds (e.g., marker substrates) can be labeled with $^{131}I$, $^{125}I$, $^{35}S$, $^{14}C$, or $^{3}H$, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product.

This invention further pertains to novel agents identified by the above-described screening assays. Accordingly, it is within the scope of this invention to further use an agent identified as described herein in an appropriate animal model. For example, an agent capable of modulating the expression and/or activity of tyrosine phosphorylated Shc (PY-Shc) and/or p66-Shc identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatment as described above.

This invention is further illustrated by the following examples which should not be construed as limiting. The contents of all references, figures, patents and published patent applications cited throughout this application are hereby incorporated by reference.

EXAMPLES

Example 1

PY-Shc in Primary Tumors of Patients with Early Stage (Stage I and Stage II) Gastric Cancer has Significant Protective Effects on Both Relapse-Free and Disease-Specific Survival Statistical analyses of PY-Shc in gastric tumor samples from patients with Stage I and Stage II tumors showed a strong trend towards decreased expression (and p66-Shc increased expression) in primary tumors of patients who relapsed or died from their disease after presentation with early stage disease (Stages I & II).

Figure 2:
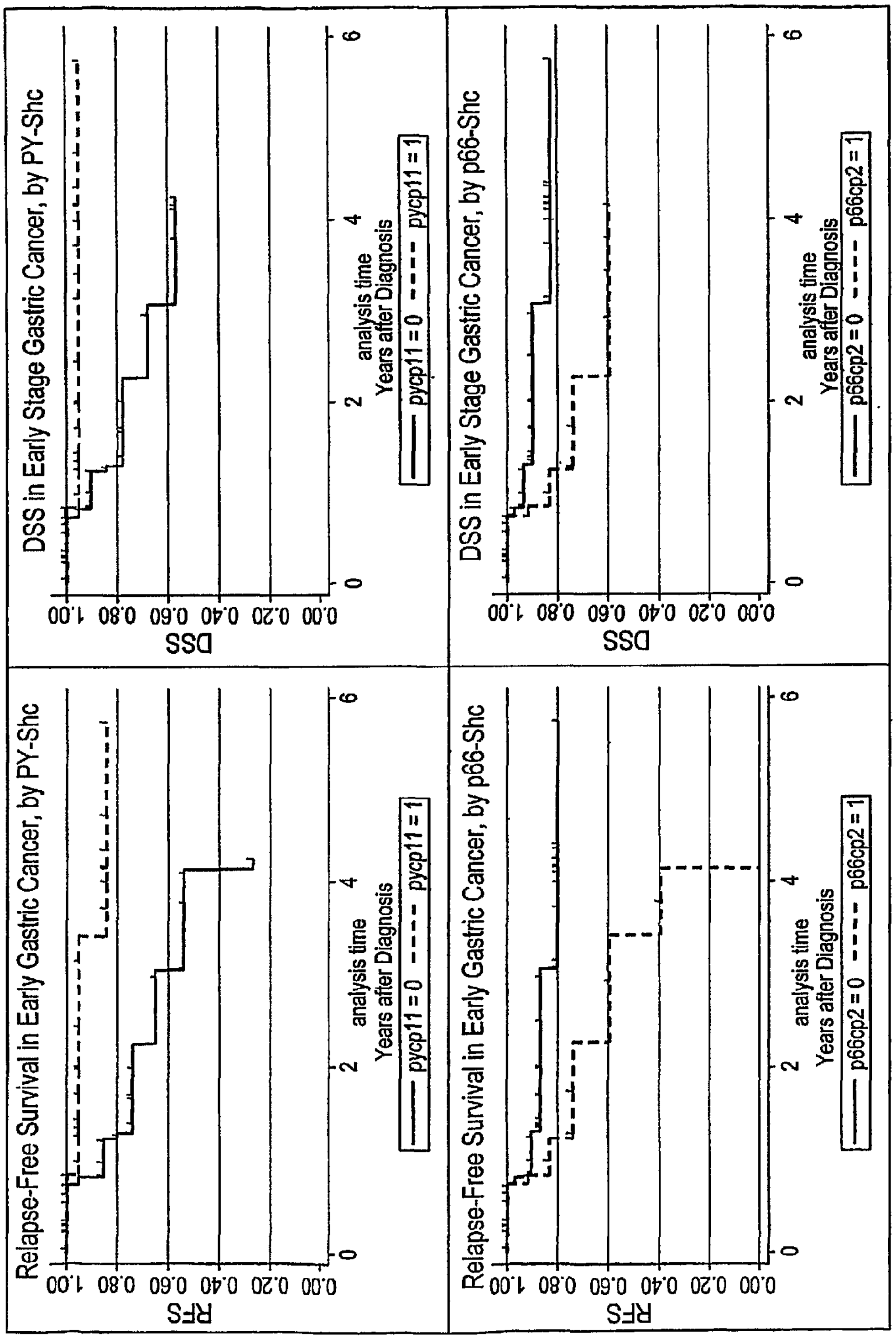
FIG. 2 depicts a Kaplan-Meier survival plot for patients with Stage I and Stage II gastric cancer with low versus high PY-Shc scores.

From a dot plot of PY-Shc versus disease-specific death (FIG. 1), a cutpoint of about 1.1 clearly separated patients into those who had high PY-Shc with good prognosis, and those patients who had low PY-Shc with poor prognosis. By univariate logistic regression analysis, high PY-Shc had a strong protective effect: patients with high PY-Shc scores were 6-fold less likely to die from their disease than patients with low PY-Shc scores (P=0.03). Kaplan-Meier survival plots for patients with low versus high PY-Shc clearly visualize these differences in outcome (FIG. 2). p66-Shc showed similar prognostic abilities (see, Tables 1 and 2).

As a continuous variable, PY-Shc had a strong protective ability for disease-specific survival (DSS) (RR of 0.39 for 1 unit increase in PY-Shc score using a 0-5 scale, or 0.009 full-scale: a 100-fold RR) that trended towards statistical significance (P=0.11). p66-Shc was a strong hazard (RR of 1.6 for 1 unit increase in score, or 10 full scale) (P=0.06). Similar abilities were seen for relapse-free survival (RFS). (See Tables 1 and 2).

TABLE 1

RFS and DSS in Early Stage Gastric Cancer: Relative Risk by the Shc Markers*

| | | RFS | | DSS | |
|---|---|---|---|---|---|
| Marker | Variable | RR (95% CI) | P | RR (95% CI) | P |
| PY-Shc | Continuous | 0.53 (0.22-1.3) | 0.15 | 0.39 (0.13-1.2) | 0.11 |
| | Hi/Lo | 0.16 (0.03-0.86) | 0.03 | 0.12 (0.01-1.0) | 0.02 |
| p66-Shc | Continuous | 1.6 (0.97-2.7) | 0.064 | 1.6 (0.94-2.8) | 0.08 |
| | Hi/Lo | 8.2 (1.9-35) | 0.005 | 5.3 (1.1-25) | 0.04 |

*Stage I and II combined; RR, relative risk calculated from logistic regression; PY-Shc cutpoint for Hi/Lo dichotomy was 1.1.

TABLE 2

RFS and DSS in Stage I & II Gastric Cancer: Life Tables by the Shc Markers*

| | | RFS % | | | | DSS % | | | |
|---|---|---|---|---|---|---|---|---|---|
| Marker | Group | n | 2 yrs | 4 yrs | P | n | 2 yrs | 4 yrs | P |
| None (PY-Shc) | All | 10/58 | 85 | 69 | | 7/58 | 87 | 77 | |
| PY-Shc | | | | | 0.014 | | | | 0.029 |
| | Hi | 2/31 | 95 | 84 | | 1/31 | 95 | 95 | |
| | Lo | 8/27 | 74 | 54 | | 6/27 | 78 | 57 | |
| None (p66 Shc) | All | 11/58 | 83 | 68 | | 8/58 | 85 | 76 | |
| p66-Shc | | | | | 0.018 | | | | 0.10 |
| | Hi | 6/12 | 74 | 40 | | 4/12 | 74 | 59 | |
| | Low | 5/46 | 87 | 80 | | 4/46 | 90 | 83 | |

*n, number of patients, where 7/58 indicates that 7 out of 58 patients recurred; RFS %, DSS % are the percentage of patients surviving without recurrence or not dying of disease, respectively, from Kaplan-Meier analyses. P is given for the log-rank univariate analysis of the Hi/Lo binomial variables. PY-Shc Hi, Lo, are patients whose primary tumors had either high (≥1.1) or low (<1.1) scores, respectively, for PY-Shc. p66 Shc Hi, Lo, are patients whose primary tumors had either high (≥2.2) or low (<2.2) scores, respectively, for p66 Shc.

Example 2

PY-Shc and P66-Shc as Prognostic Indicators of Cancer Recurrence and Disease Survival in Patients With of Stage I Gastric Cancer The greatest clinical need for prognostic markers in gastric cancer concerns patients with Stage I disease. For these patients, surgical and medical oncologists currently must balance the minimal likely benefit that might be derived from the aggressive D2-level dissection and toxic chemo-radiation regimen adopted by some as the current standard of care (MacDonald, J. (2001) *N Engl J Med* 345:725-730) against the modest risk (approximately 20%) that Stage I patients treated only by D1-level dissection and surgical resection will have recurrent disease. Prognostic markers that will identify Stage I patients who are likely (and those unlikely) to experience recurrent disease will aid and improve this clinical treatment decision.

In the previous example, PY-Shc in primary tumors of patients with Stage I gastric cancer had significant protective effects on both relapse-free and disease-specific survival. PY-Shc showed a strong trend towards decreased expression in primary tumors of patients who relapsed or died from their disease after presentation with Stage I disease.

Figure 3:
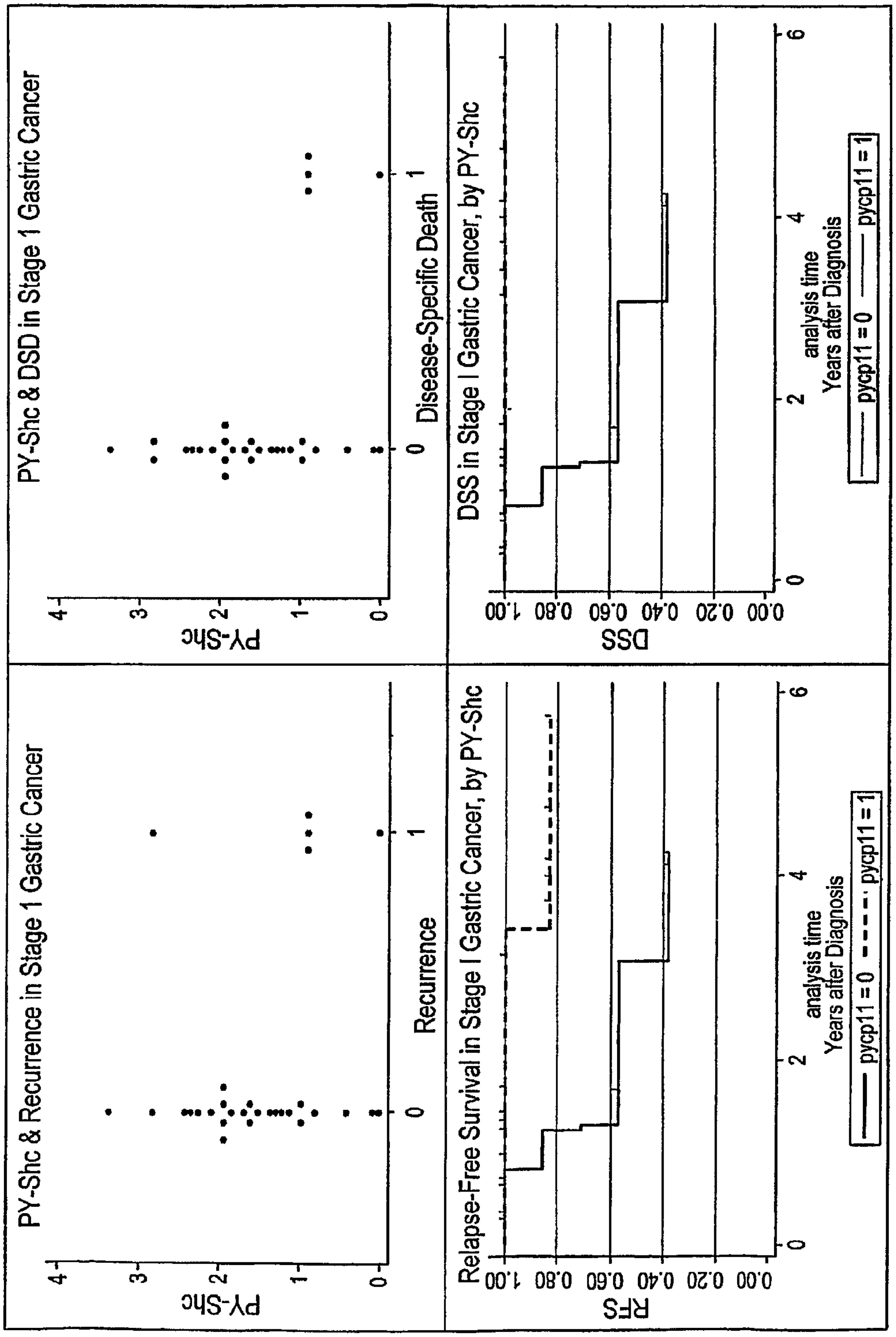
FIG. 3 depicts a Kaplan-Meier survival plot of RFS % and DFS % in patients with Stage I and Stage II gastric cancer using PY-Shc Scores.

From a dot plot of PY-Shc versus disease-specific death (FIG. 3), the previously assigned cutpoint of 1.1 clearly separated patients into those who had high PY-Shc with good prognosis, and those patients who had low PY-Shc with poor prognosis. By univariate logistic regression analysis, high PY-Shc had a strong protective effect; no patients with high PY-Shc scores died from their disease (see Kaplan-Meier plots in FIG. 3). p66 Shc showed similar prognostic abilities.

As a continuous variable, PY-Shc had an extraordinarily strong protective ability for disease-specific survival (RR of 0.15 for 1 unit increase in PY-Shc score on 0-5 scale, or 0.00008 full-scale: a 13,000-fold RR) that was statistically significant (P=0.05). For RFS, the dichotomized PY-Shc had a very strong protective ability (RR of 0.08: a 12-fold RR) that was statistically significant (P=0.04) (see Tables 3 and 4).

TABLE 3

RFS and DSS in Stage I Gastric Cancer: Relative Risk by PY-Shc*

| | | RFS | | DSS | |
|---|---|---|---|---|---|
| Marker | Variable | RR (95% CI) | P | RR (95% CI) | P |
| PY-Shc | Continuous | 0.46 (0.13-1.7) | 0.24 | 0.15 (0.02-0.99) | 0.05 |
| | Hi/Lo | 0.08 (0.007-0.85) | 0.036 | 0** | |

*RR, relative risk calculated from logistic regression; PY-Shc cutpoint for Hi/Lo dichotomy was 1.1.

**Low PY-Shc category predicted DSD perfectly.

TABLE 4

RFS and DSS in Stage I Gastric Cancer: Life Tables by PY-Shc

| Marker | Group | RFS % n | 2 yrs | 4 yrs | P | DSS % n | 2 yrs | 4 yrs | P |
|---|---|---|---|---|---|---|---|---|---|
| None (PY-Shc) | All | 5/30 | 91 | 78 | | 4/30 | 91 | 82 | |
| PY-Shc | | | | | 0.04 | | | | 0.009 |
| | Hi | 1/20 | 100 | 90 | | 0/20 | 100 | 100 | |
| | Lo | 4/10 | 70 | 58 | | 4/10 | 70 | 58 | |

PY-Shc in primary tumors of patients with early stage gastric cancer appears to have significant protective effect on over-all survival. PY-Shc (but not p66 Shc) was significantly decreased in primary tumors of patients who died subsequent to presentation with early stage disease (Stages I & II).

As a continuous variable, PY-Shc had a strong protective ability (HR of 0.62 for 1 unit increase in PY-Shc score on 0-5 scale, or 0.092 full-scale: an 11-fold HR) that closely approached statistical significance (P=0.055).

From a dot plot of PY-Shc versus death, a cutpoint of about 1.5 clearly separated patients into those who had high PY-Shc with good prognosis (85%, 17/20 survived), and those patients who had low PY-Shc with poor prognosis (44%, 14/32 survived)(P=0.003). By univariate Cox proportional hazards analysis, high PY-Shc had a strong protective effect: patients with high PY-Shc scores were 5-fold less likely to die than patients with low PY-Shc scores (P=0.0018). In multivariate Cox analysis after adjusting for tumor grade, stage, chemotherapy and radiation therapy, only PY-Shc (HR=0.22, P=0.015) and the intestinal tumor type (HR=0.38, P=0.046) remained as significant predictors of survival.

The statistical analyses of the data presented above are shown below. Summary Statistics (all output using software package, Stata, version 8):

Dictionary of Variables:

describe pyaverb p66ave ttypen stagen grade cther rther dsd survdays

| variable name | storage type | display format | value label | variable label |
|---|---|---|---|---|
| pyaverb | float | %9.0 g | | RB's ave PY-Shc |
| p66ave | float | %9.0 g | | RB's p66 Shc |
| ttypen | long | %11.0 g | ttypen | 2, diffuse;<br>3, intestinal; . . . |
| stagen | long | %8.0 g | stagen | tumor stage: 1A; 2, 1B;<br>3,<br>2; 4, 3A; 5, 3B; 6, 4 |
| grade | byte | %8.0 g | | tumor grade, 1, 2, 3 |
| cther | byte | %8.0 g | | chemotherapy 0, 1 |
| rther | byte | %8.0 g | | radiation therapy 0, 1 |
| dsd | byte | %8.0 g | | Death from any cause |
| survdays<br>loss to<br>followup | int | %8.0 g | | Days from dx to death or |

Summary of Variables and Clinical Information:

sum pyaverb pyrb pyrl p66ave survdays dsd cther rther grade stagen ttypen

| Variable | Obs | Mean | Std. Dev. | Min | Max |
|---|---|---|---|---|---|
| pyaverb | 132 | 1.362576 | .966224 | 0 | 4.43 |
| pyrb | 132 | 1.4575 | 1.061049 | 0 | 4.7 |
| pyrl | 164 | 2.006402 | 1.134419 | 0 | 4.7 |
| p66ave | 133 | .8978947 | 1.147316 | 0 | 4.96 |
| survdays | 146 | 971.5959 | 994.0464 | 11 | 4551 |
| dsd | 127 | .488189 | .5018401 | 0 | 1 |
| cther | 140 | .3214286 | .4687018 | 0 | 1 |
| rther | 140 | .2071429 | .406714 | 0 | 1 |
| grade | 150 | 2.64 | .7073915 | 0 | 4 |
| stagen | 148 | 3.655405 | 1.606589 | 1 | 6 |
| ttypen | 155 | 2.56129 | .7819711 | 1 | 7 |

Example 3

Correlation of the Shc Markers and Clinicopathological Characteristics

Shown below is a correlation analysis of all the available marker and clinical information. Notice that PY-Shc shows a negative correlation with overall survival(dsd). Other significant correlations are shaded. Note that the significance of the correlations have not been adjusted (reduced) for multiple comparisons. The table shows ± correlation coefficient, with the respective P-value underneath each correlation coefficient.

pwcorr pyaverb p66ave ttypen stagen grade cther rther survdays dsd, sig

| | pyaverb | p66ave | ttypen | stagen | grade | cther | rther | |
|---|---|---|---|---|---|---|---|---|
| pyaverb | 1.0000 | | | | | | | |
| p66ave | 0.0643<br>0.4796 | 1.0000 | | | | | | |
| ttypen | 0.0371<br>0.6903 | 0.1053<br>0.2564 | 1.0000 | | | | | |
| stagen | -0.0084<br>0.9298 | -0.0616<br>0.5208 | -0.2409<br>0.0038 | 1.0000 | | | | |
| grade | -0.0884<br>0.3453 | -0.0813<br>0.3880 | -0.4093<br>0.0000 | - 0.1607<br>0.0543 | 1.0000 | | | |
| cther | 0.1326<br>0.1774 | -0.0818<br>0.4114 | -0.2024<br>0.0190 | 0.3174<br>0.0001 | 0.0685<br>0.4300 | 1.0000 | | |
| rther | -0.0483<br>0.6247 | 0.0104<br>0.9166 | -0.0267<br>0.7597 | 0.0064<br>0.9400 | -0.0057<br>0.9479 | 0.5162<br>0.0000 | 1.0000 | |
| survdays | 0.0069<br>0.9430 | -0.0793<br>0.4126 | 0.0066<br>0.9381 | -0.3143<br>0.0001 | -0.1870<br>0.0264 | -0.0665<br>0.4383 | -0.0535<br>0.5334 | |
| dsd | -0.2071<br>0.0418 | -0.0364<br>0.7244 | 0.0042<br>0.9635 | 0.3327<br>0.0001 | 0.1726<br>0.0562 | -0.0234<br>0.8016 | -0.0180<br>0.8463 | -.5186<br>0.0000 |

Example 4

Analysis of Overall Death as a Function of the Shc Markers

Figure 4:
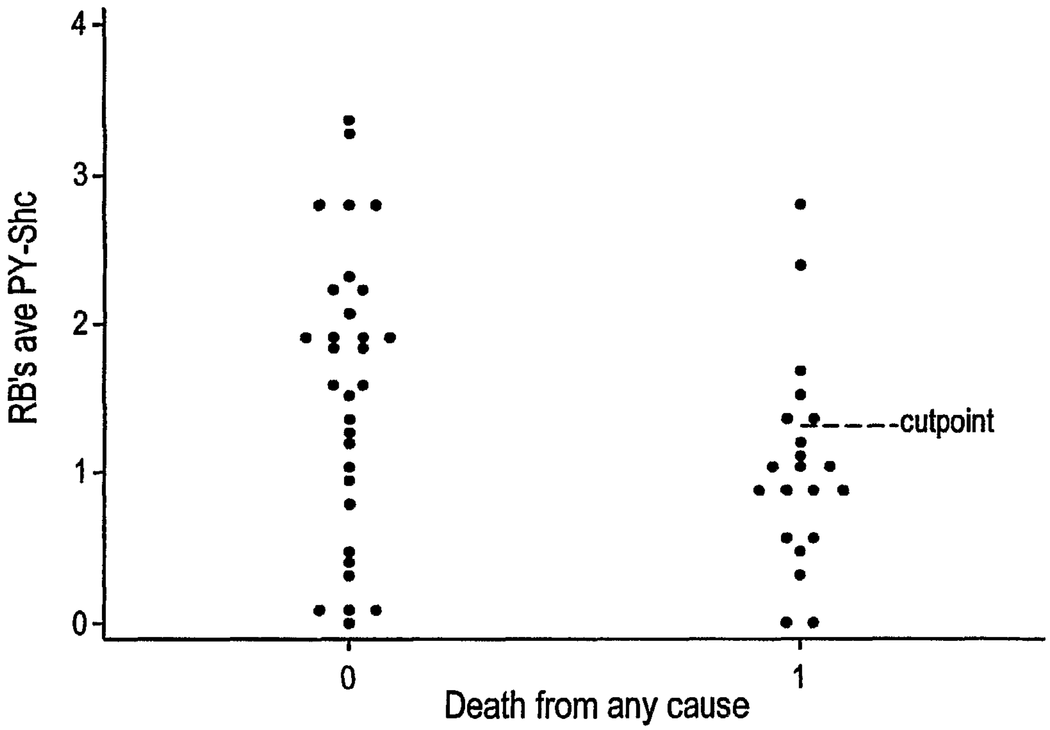
FIG. 4 depicts a dot plot of PY-Shc scores in Stage I and II gastric cancer as a function of death from any cause.
Figure 5:
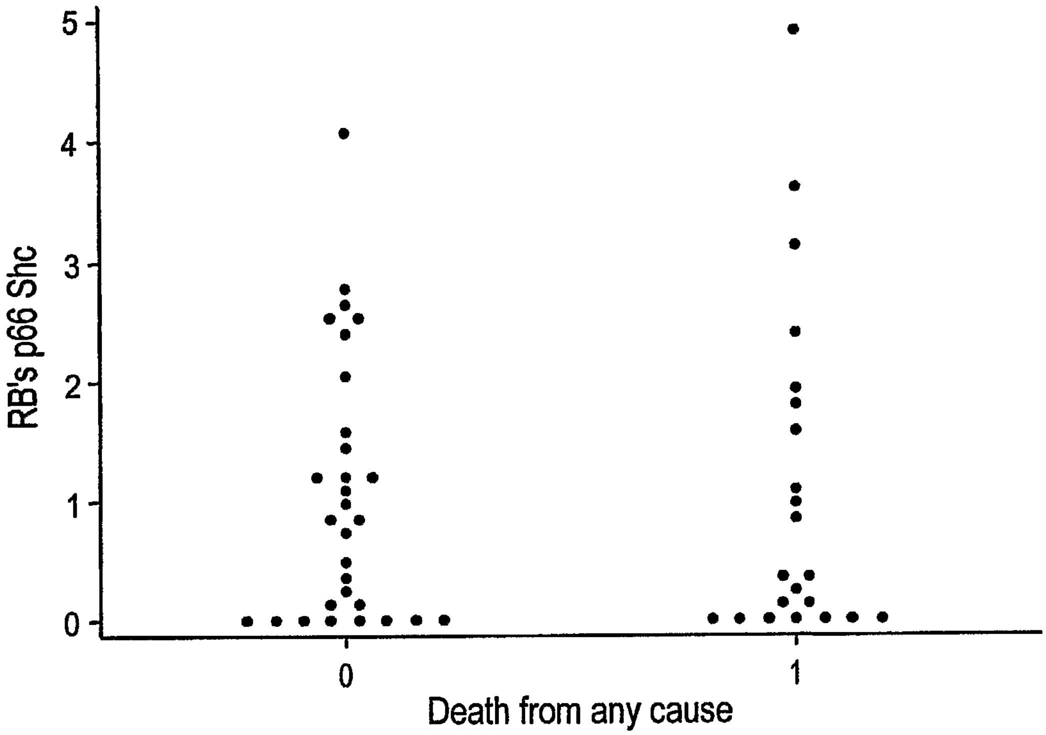
FIG. 5 depicts a dot plot of p66-Shc scores in Stage I & II gastric cancer as a function of death from any cause.

PY-Shc (but not p66 Shc) was significantly decreased in patients who died subsequent to presentation with early stage disease (Stages 1 & II). FIG. 4 shows the distribution of PY-Shc scores in Stage I & II gastric cancer as a function of death from any cause.

ttest pyaverb if stagen<4 & dsd!=. & survdays!=., by(dsd)
Two-sample t test with equal variances

| Group | Obs | Mean | Std. Err. | Std. Dev. | [95% Conf. Interval] | |
|---|---|---|---|---|---|---|
| 0 | 31 | 1.546452 | .1733699 | .9652825 | 1.192383 | 1.90052 |
| 1 | 21 | 1.045238 | .1478426 | .6774999 | .7368438 | 1.353632 |
| combined | 52 | 1.344038 | .1232391 | .8886898 | 1.096626 | 1.591451 |
| diff | | .5012135 | .2435609 | | .0120071 | .99042 |

Degrees of freedom: 50

Ho: mean(0)−mean(1)=diff=0

| Ha: diff < 0 | Ha: diff 1 = 0 | Ha: diff > 0 |
|---|---|---|
| t = 2.0579 | t = 2.0579 | t = 2.0579 |
| P < t = 0.9776 | P < \| t \| = 0.0448 | P > t = 0.0224 |

Dr. Lis: ttest pyrl if stagen<4 & dsd!=. & survdays!=., by(dsd)

Two-sample t test with equal variances

| Group | Obs | Mean | Std. Err. | Std. Dev. | [95% Conf. Interval] | |
|---|---|---|---|---|---|---|
| 0 | 40 | 2.2175 | .1827808 | 1.156007 | 1.847791 | 2.587209 |
| 1 | 25 | 1.926 | .2295851 | 1.147926 | 1.45216 | 2.39984 |
| combined | 65 | 2.105385 | .1429855 | 1.152786 | 1.819738 | 2.391031 |
| diff | | .2915 | .2939419 | | −.2958961 | .8788961 |

Degrees of freedom: 63

Ho: mean(0)−mean(1)=diff=0

| Ha: diff < 0 | Ha: diff 1 = 0 | Ha: diff > 0 |
|---|---|---|
| t = 0.9917 | t = 0.9917 | t = 0.9917 |
| P < t = 0.8374 | P < \|t\| = 0.3251 | P > t = 0.1626 |

Dr. Bagdasaryan: ttest pyrb if stagen<4 & dsd!=. & survdays!=., by(dsd)

Two-sample t test with equal variances

| Group | Obs | Mean | Std. Err. | Std. Dev. | [95% Conf. Interval] | |
|---|---|---|---|---|---|---|
| 0 | 31 | 1.470968 | .1662485 | .9256326 | 1.131443 | 1.810493 |
| 1 | 21 | 1.352857 | .2329185 | 1.067367 | .8669977 | 1.838717 |
| combined | 52 | 1.423269 | .1354618 | .976829 | 1.151318 | 1.69522 |
| diff | | .1181106 | .278323 | | −.4409176 | .6771388 |

Degrees of freedom: 50

Ho: mean(0)−mean(1)=diff 0

| Ha: diff < 0 | Ha: diff 1 = 0 | Ha: diff > 0 |
|---|---|---|
| t = 0.4244 | t = 0.4244 | t = 0.4244 |
| P < t = 0.6634 | P > \|t\| = 0.6731 | P > t = 0.3366 |

Note that there was a marked correlation between Dr. Lis' and Dr. Bagdasaryan's scores:

pwcorr pyave pyrb pyrl dsd survdays, sig

| | pyaverb | pyrb | pyrl |
|---|---|---|---|
| pyaverb | 1.0000 | | |
| pyrb | 0.8966 | 1.0000 | |
| | 0.0000 | | |
| pyrl | 0.7662 | 0.8331 | 1.0000 |
| | 0.0000 | 0.0000 | |

ttest p66ave if stagen<4 & dsd!=. & survdays!=., by(dsd)

Two-sample t test with equal variances

| Group | Obs | Mean | Std. Err. | Std. Dev. | [95% Conf. Interval] | |
|---|---|---|---|---|---|---|
| 0 | 30 | 1.044 | .1995861 | 1.093178 | .6358005 | 1.452199 |
| 1 | 22 | 1.062727 | .295136 | 1.384311 | .4489583 | 1.676496 |
| combined | 52 | 1.051923 | .1680596 | 1.211895 | .7145293 | 1.389317 |
| diff | | −.0187273 | .3435437 | | −.7087551 | .6713006 |

Degrees of freedom: 50

Ho: mean(0)−mean(1)=diff=0

| Ha: diff < 0 | Ha: diff 1 = 0 | Ha: diff > 0 |
|---|---|---|
| t = -0.0545 | t = -0.0545 | t = -0.0545 |
| P < t = 0.4784 | P < \|t\| = 0.9567 | P > t = 0.5216 |

Example 5

PY-Shc has a Strong Protective Ability as a Continuous Variable

PY-Shc as a continuous variable has a strong protective ability (HR of 0.62 for 1 unit increase in PY-Shc score on 0-5 scale, or 0.092 full-scale: an 11-fold HR) that closely approached statistical significance (P=0.055).

stcox pyaverb if stagen<4 & survdays!=. & dsd!=., nolog failure_d: dsd analysis time_t: survdays Cox regression—Breslow method for ties

| | | | | | |
|---|---|---|---|---|---|
| No. of subjects | = | 52 | Number of obs | = | 52 |
| No. of failures | = | 21 | | | |
| Times at risk | = | 56095 | | | |
| | | | LR chi2 (1) | = | 3.67 |
| Log likelihood | = | -72.426032 | Probl > chi2 | = | 0.0554 |

| _t | Haz. Ratio | Std. Err. | z | P > \|z\| | [95% Conf. Interval] | |
|---|---|---|---|---|---|---|
| pyaverb | .6160105 | .1602575 | -1.86 | 0.063 | .3699515 | 1.025726 |

Example 6

PY-Shc as a Cutpoint Variable

From the dot plot of PY-Shc as a function of death, above, it was clear that an appropriate and useful cutpoint could be estimated as a PY-Shc value of about 0.15. With this cutpoint, 85% of patients with high PY-Shc survived while only 15% of patients with low PY-Shc survived (P=0.003):

tab dsd pycp if stagen<4 & pyaverb!=. & survdays!=. & dsd!=., chi2 col

| Key |
|---|
| frequency<br>column percentage |

| Death from | pycp | | |
|---|---|---|---|
| any cause | 0 | 1 | Total |
| 0 | 14<br>43.75 | 17<br>85.00 | 31<br>59.62 |
| 1 | 18<br>56.25 | 3<br>15.00 | 21<br>40.38 |
| Total | 32<br>100.00 | 20<br>100.00 | 52<br>100.00 |

Pearson chi2(1) = 8.6986
Pr = 0.003

Figure 6:
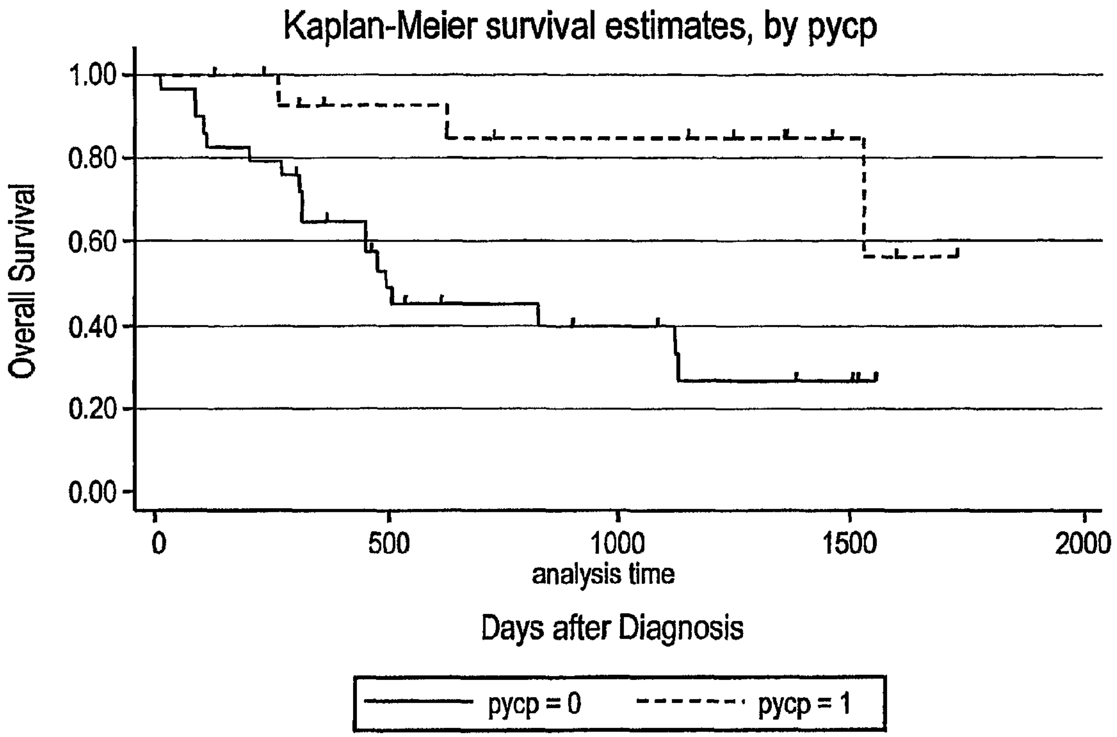
FIG. 6 depicts a Kaplan-Meier survival plot showing the difference between the overall survival of patients with Stage I and Stage II gastric cancer whose tumors have high versus low PY-Shc scores.
Figure 7:
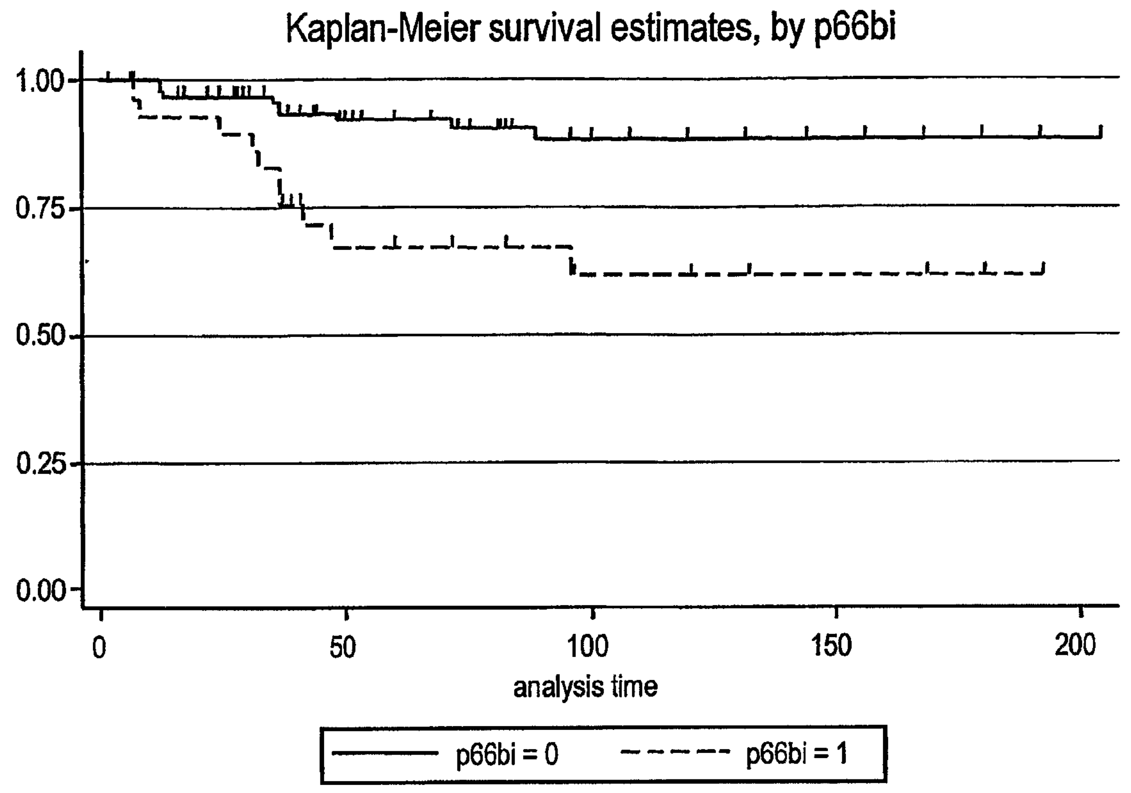
FIG. 7 depicts a Kaplan-Meier survival plot of disease-specific survival of patients with Stage I and Stage II gastric cancer as a function of p66 Shc. The ordinate is disease-specific survival as a fraction of patients surviving. Abscissa is months after diagnosis. p66bi=0 is p66-Shc scores <=2.5; p66bi=1 is p66-Shc scores >2.5-5. Censored data are indicated by vertical hash marks on the curves.
Figure 8:
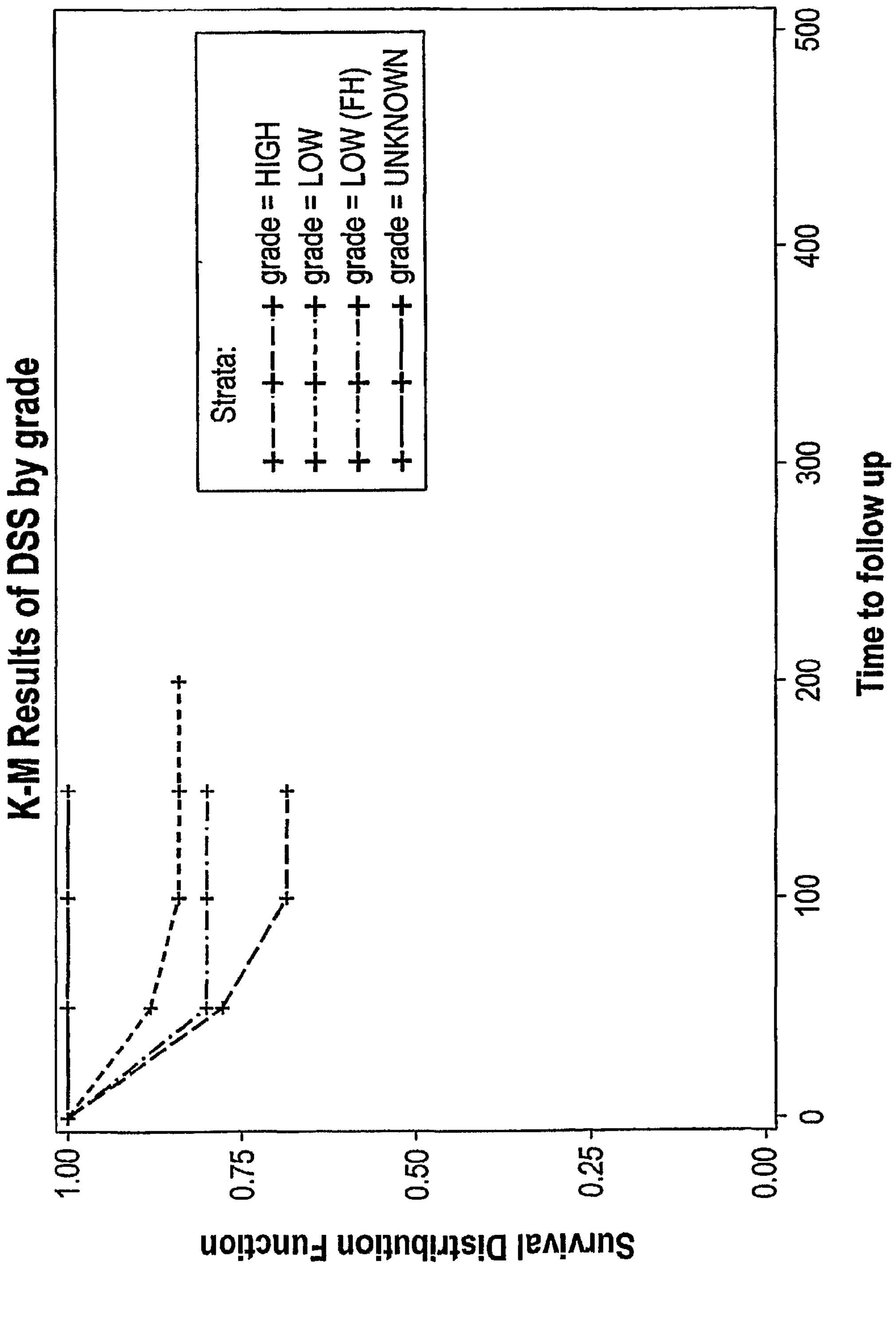
FIG. 8 depicts a Kaplan-Meier survival plot of time to disease-specific death as a function of tumor grade for patients with Stage II and Stage III colon cancer.
Figure 9:
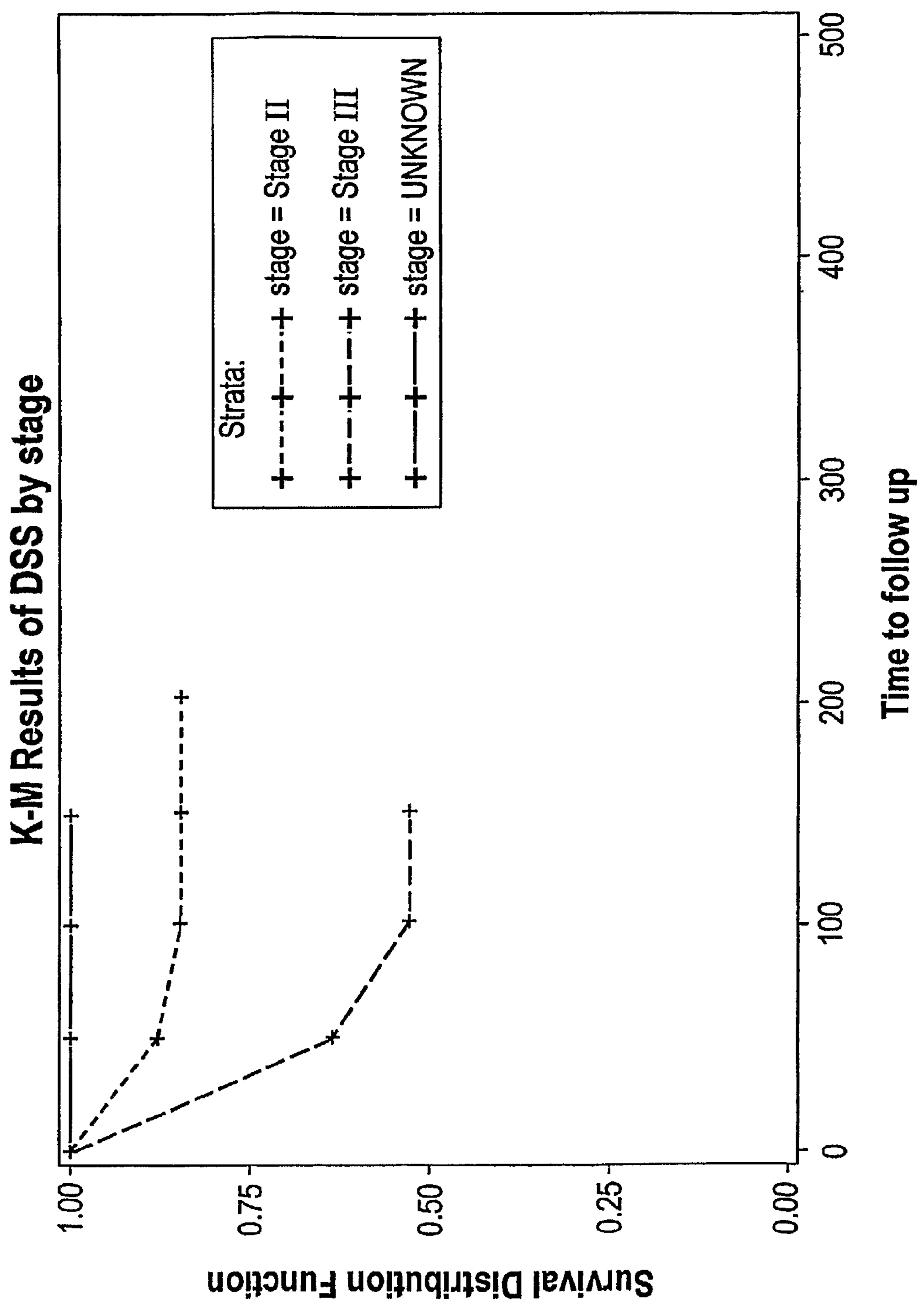
FIG. 9 depicts a Kaplan-Meier survival plot of time to disease-specific death as a function of tumor stage for patients with Stage II and Stage III colon cancer.
Figure 10:
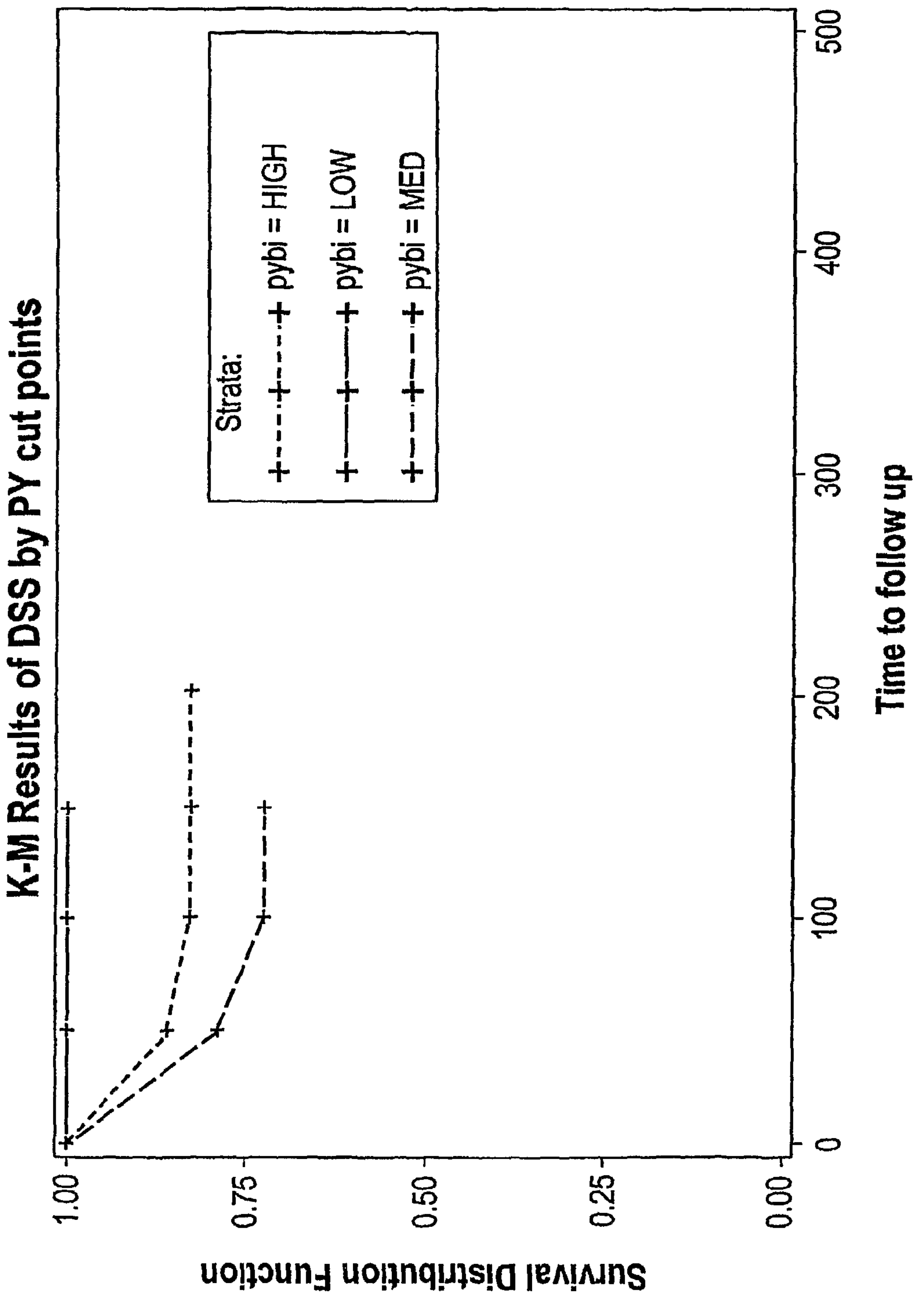
FIG. 10 depicts a Kaplan-Meier survival plot of time to disease-specific death as a function of PY-Shc scores for patients with Stage II and Stage III colon cancer.
Figure 11:
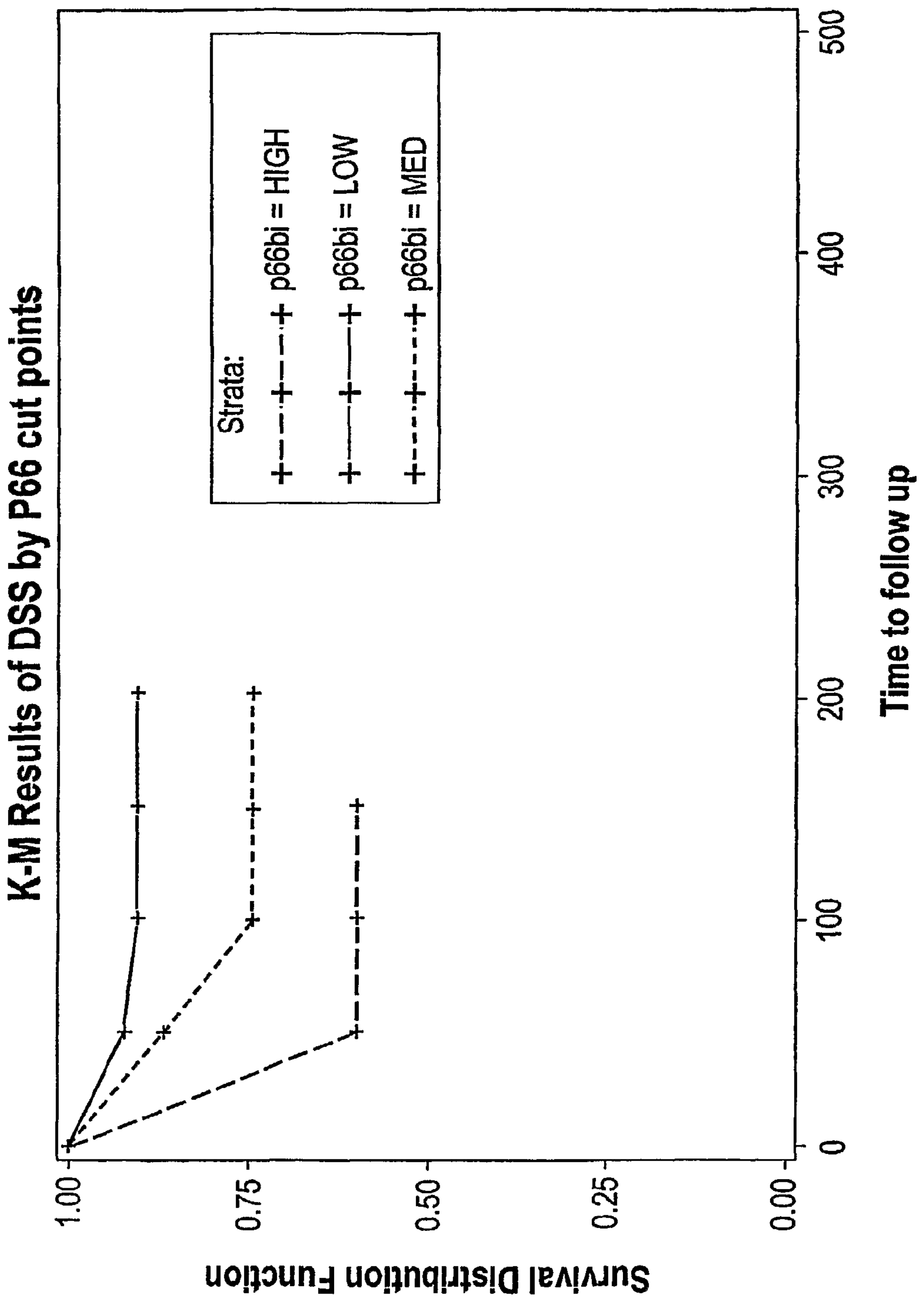
FIG. 11 depicts a Kaplan-Meier survival plot of time to disease-specific death as a function of p66-Shc scores for patients with Stage II and Stage III colon cancer.
Figure 12:
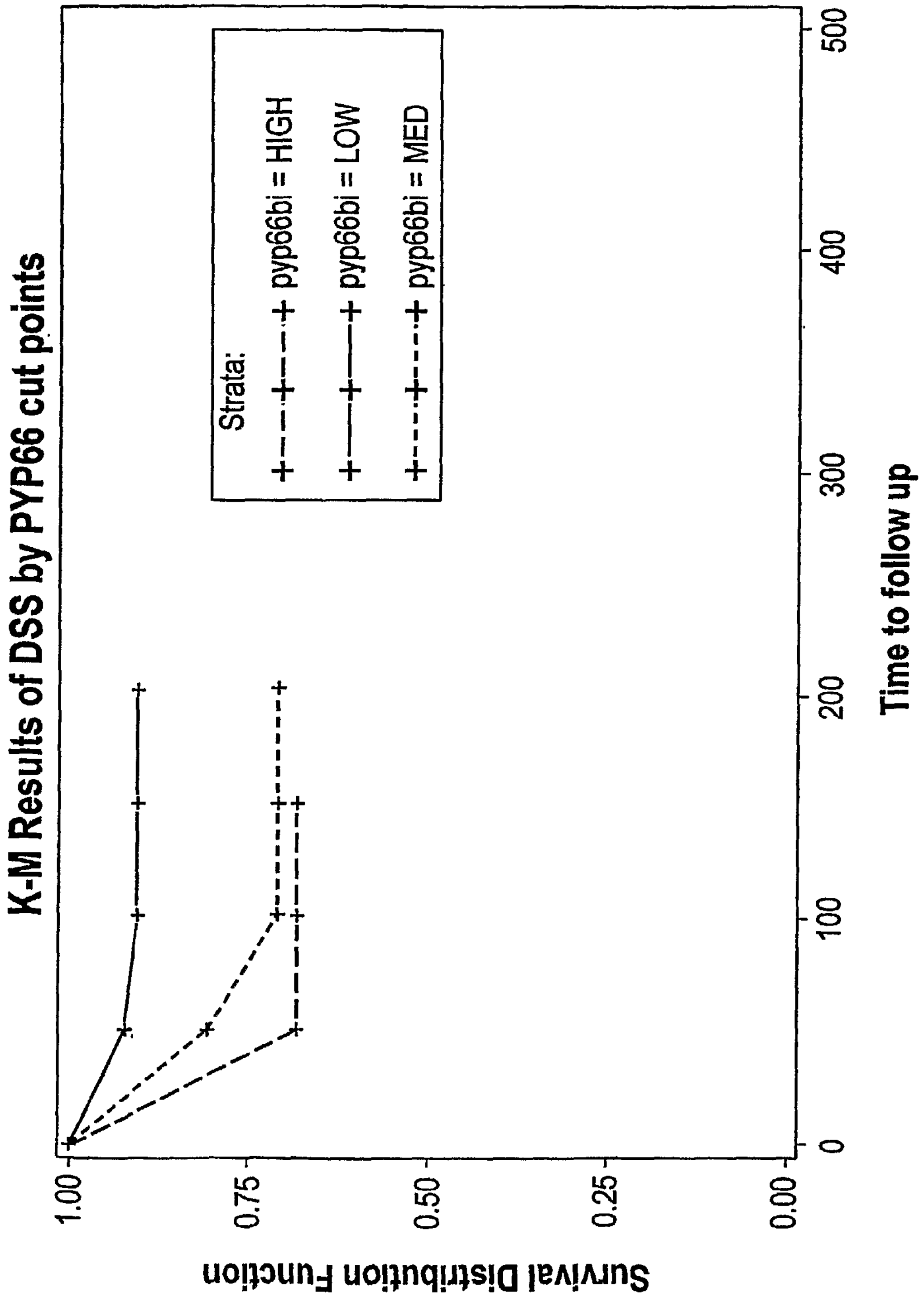
FIG. 12 depicts a Kaplan-Meier survival plot of time to disease-specific death as a function of the PYp66-Shcproduct scores for patients with Stage II and Stage III colon cancer.
Figure 13:
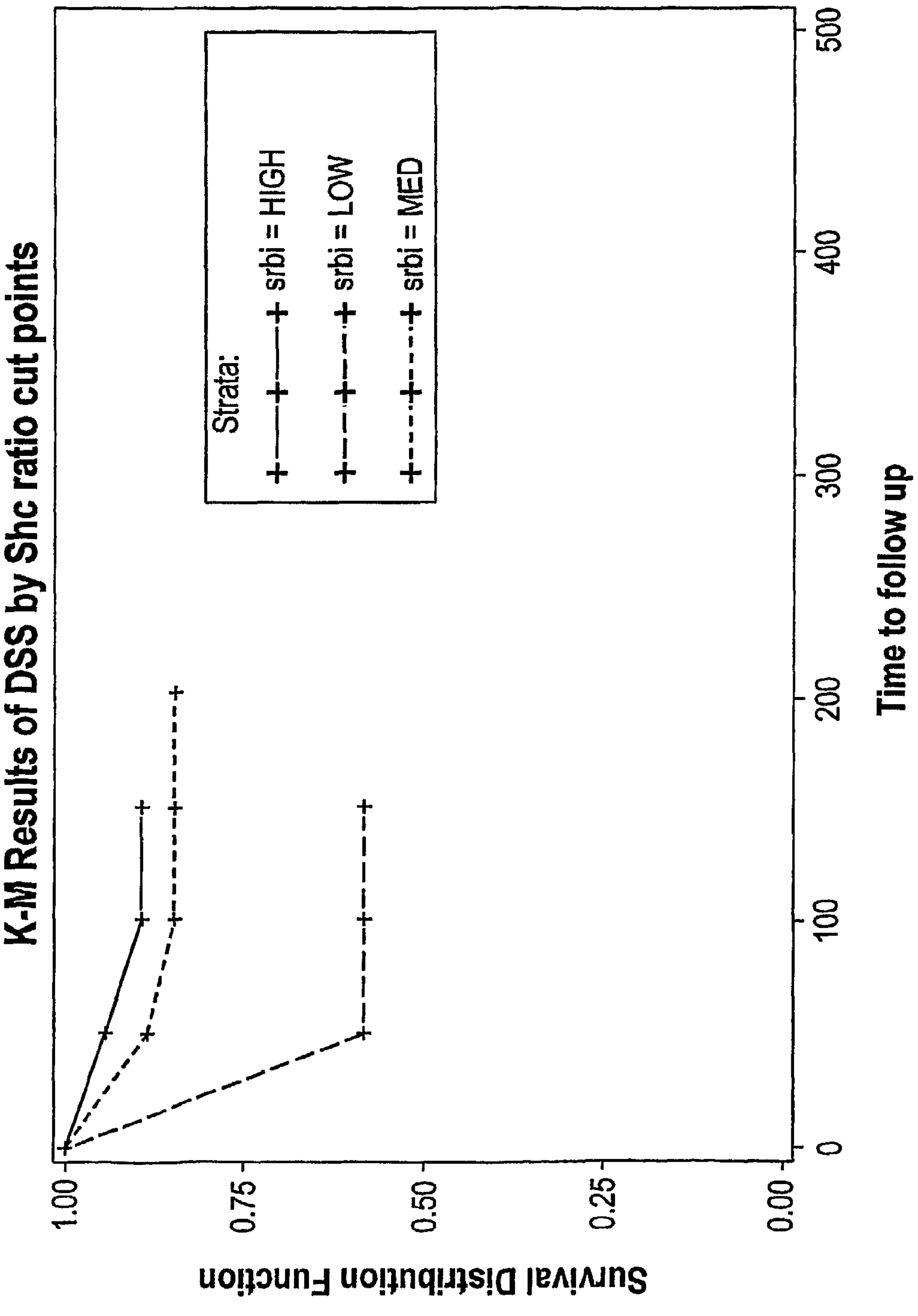
FIG. 13 depicts a Kaplan-Meier survival plot of time to disease-specific death as a function of the Shc ratio scores for patients with Stage II and Stage III colon cancer.
Figure 14:
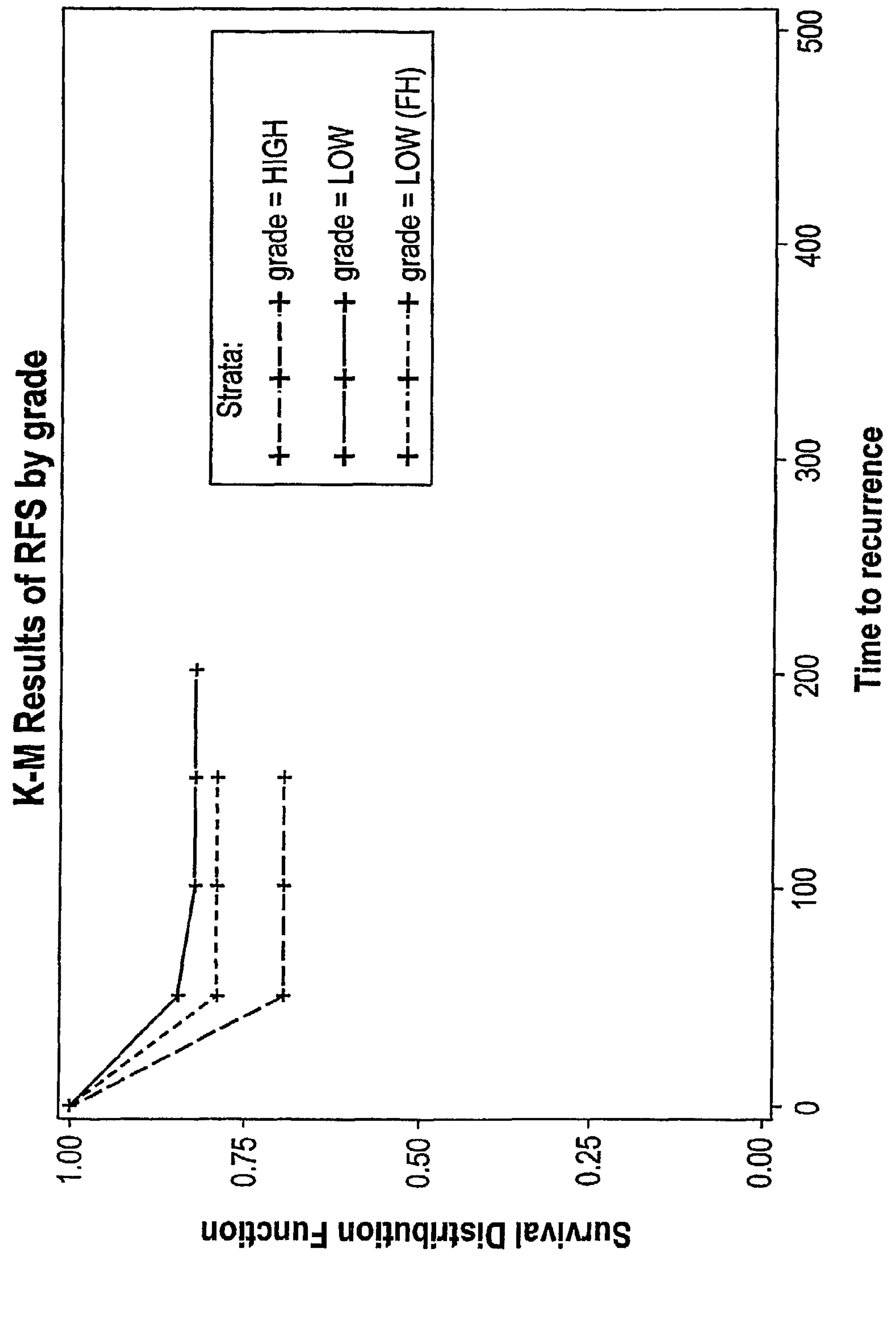
FIG. 14 depicts a Kaplan-Meier survival plot of time to recurrence-free survival as a function of tumor grade for patients with Stage II and Stage III colon cancer.
Figure 15:
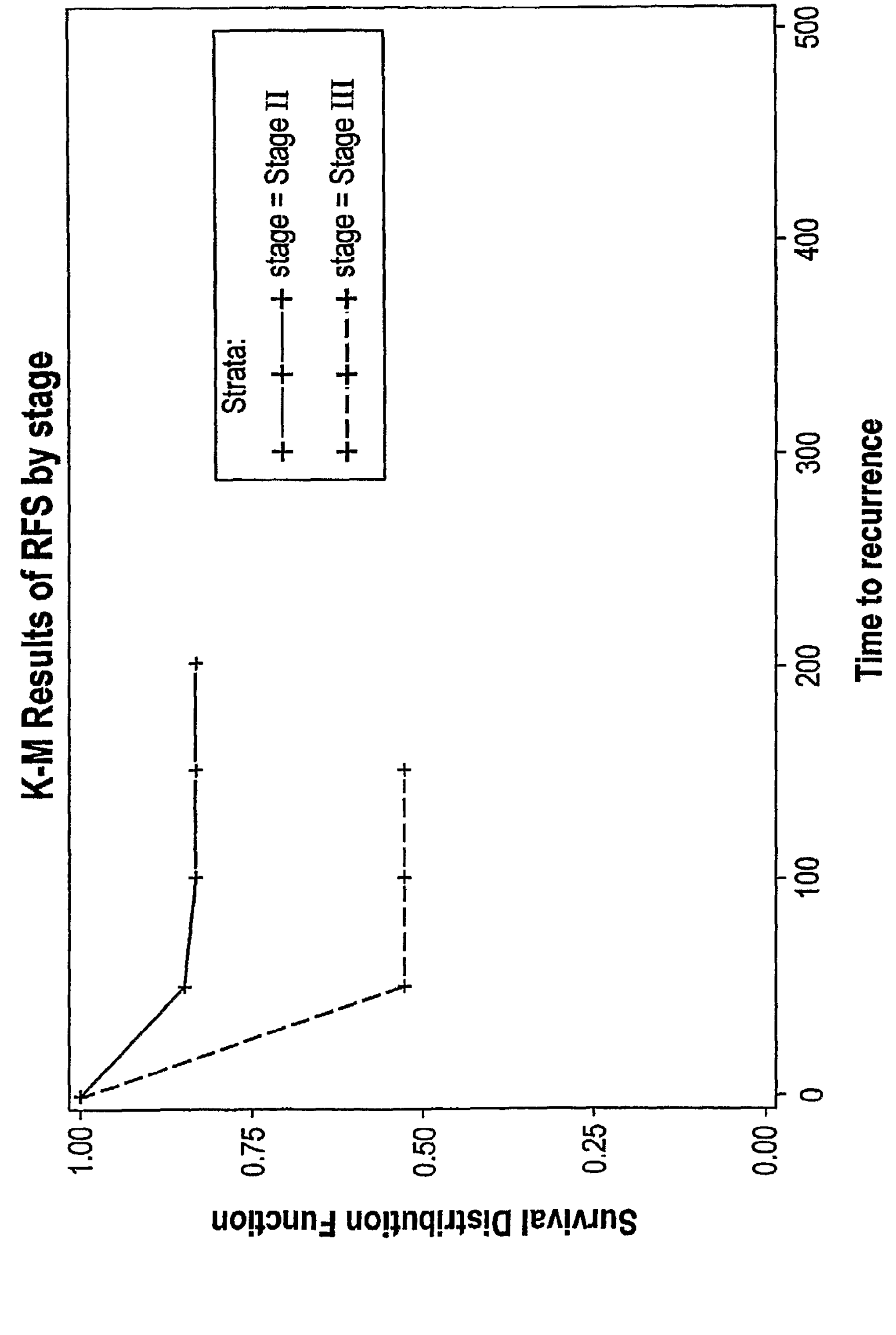
FIG. 15 depicts a Kaplan-Meier survival plot of time to recurrence-free survival as a function of tumor stage for patients with Stage II and Stage III colon cancer.
Figure 16:
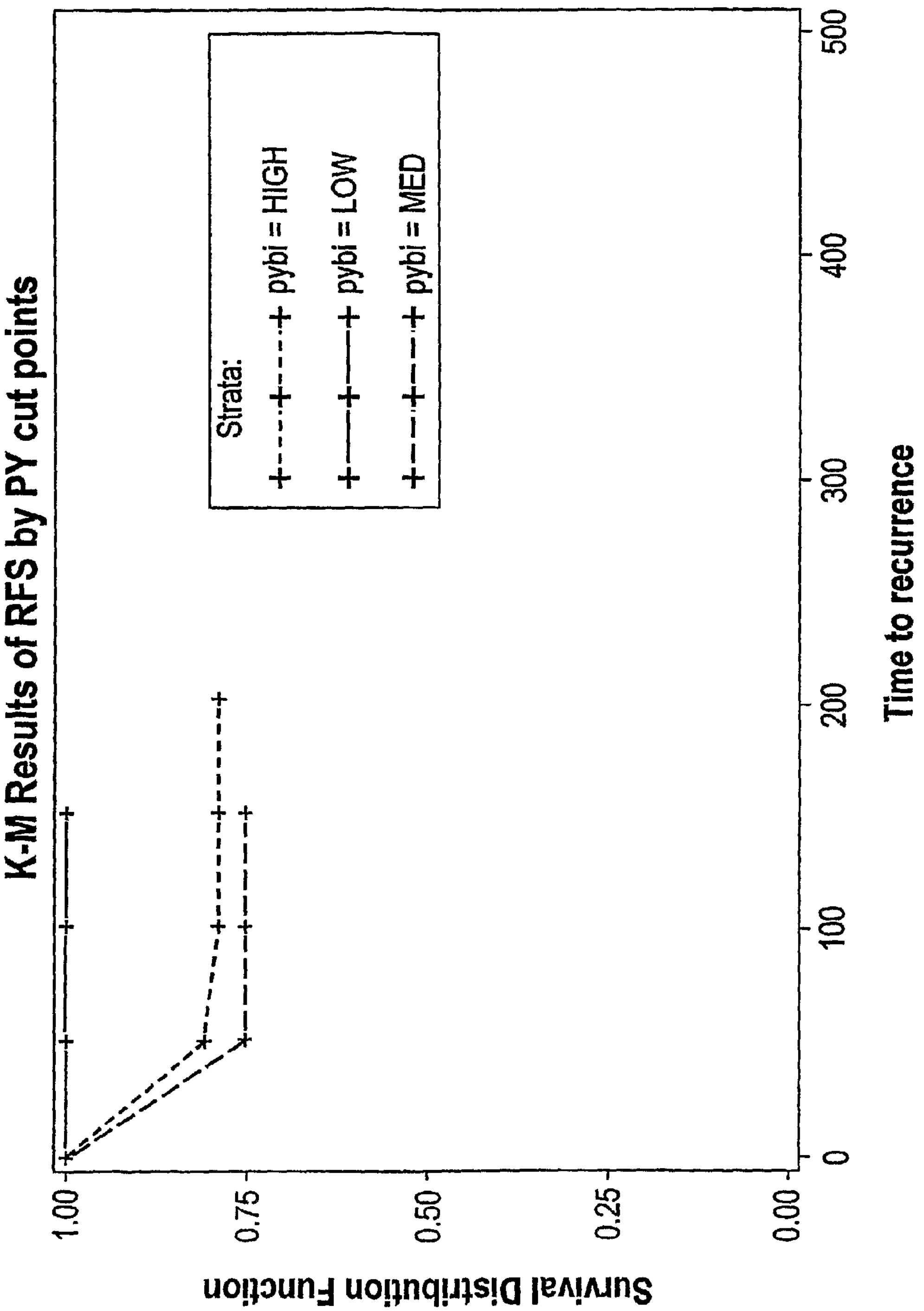
FIG. 16 depicts a Kaplan-Meier survival plot of time to recurrence-free survival as a function of PY-Shc scores for patients with Stage II and Stage III colon cancer.
Figure 17:
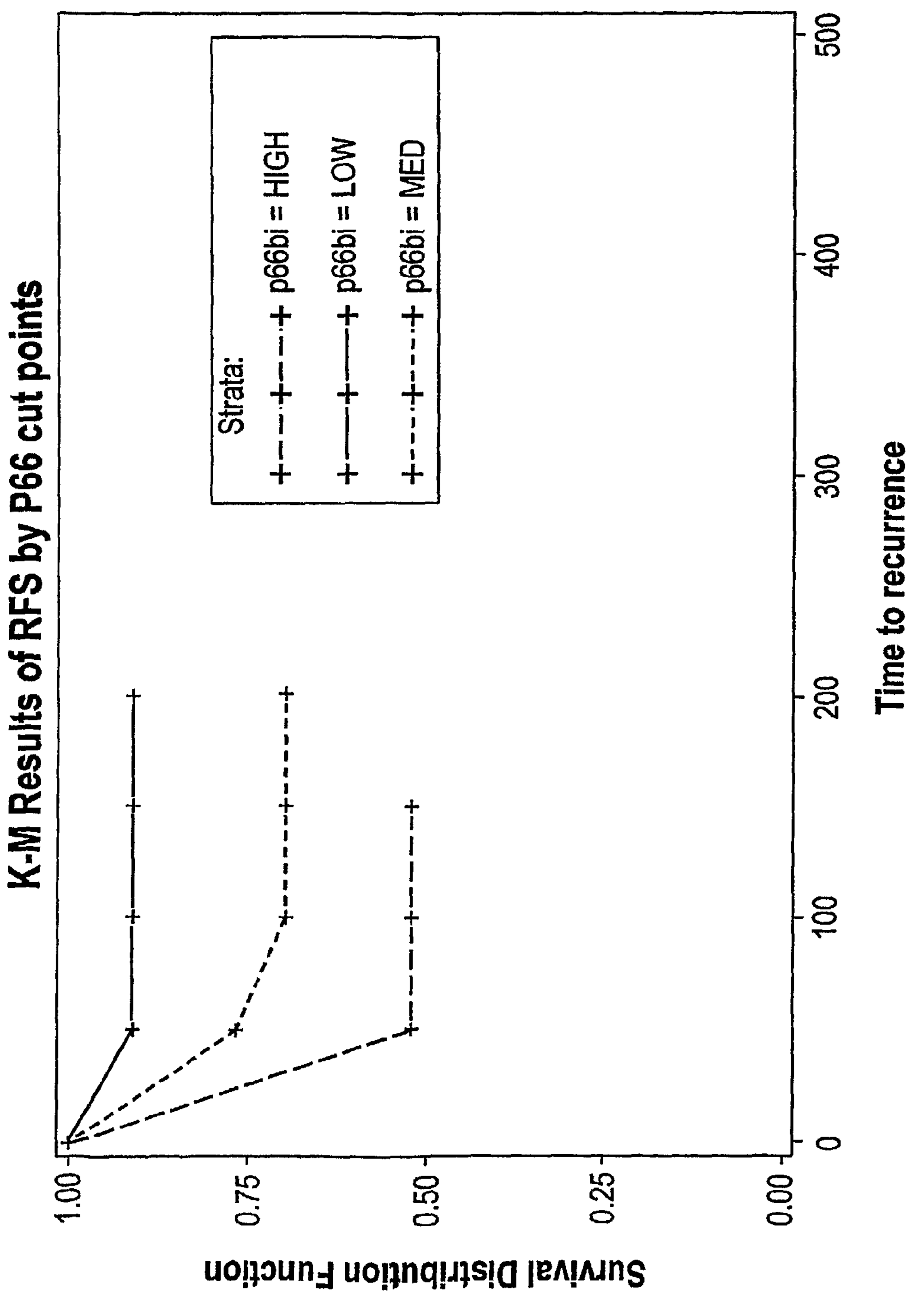
FIG. 17 depicts a Kaplan-Meier survival plot of time to recurrence-free survival as a function of p66-Shc scores for patients with Stage II and Stage III colon cancer.
Figure 18:
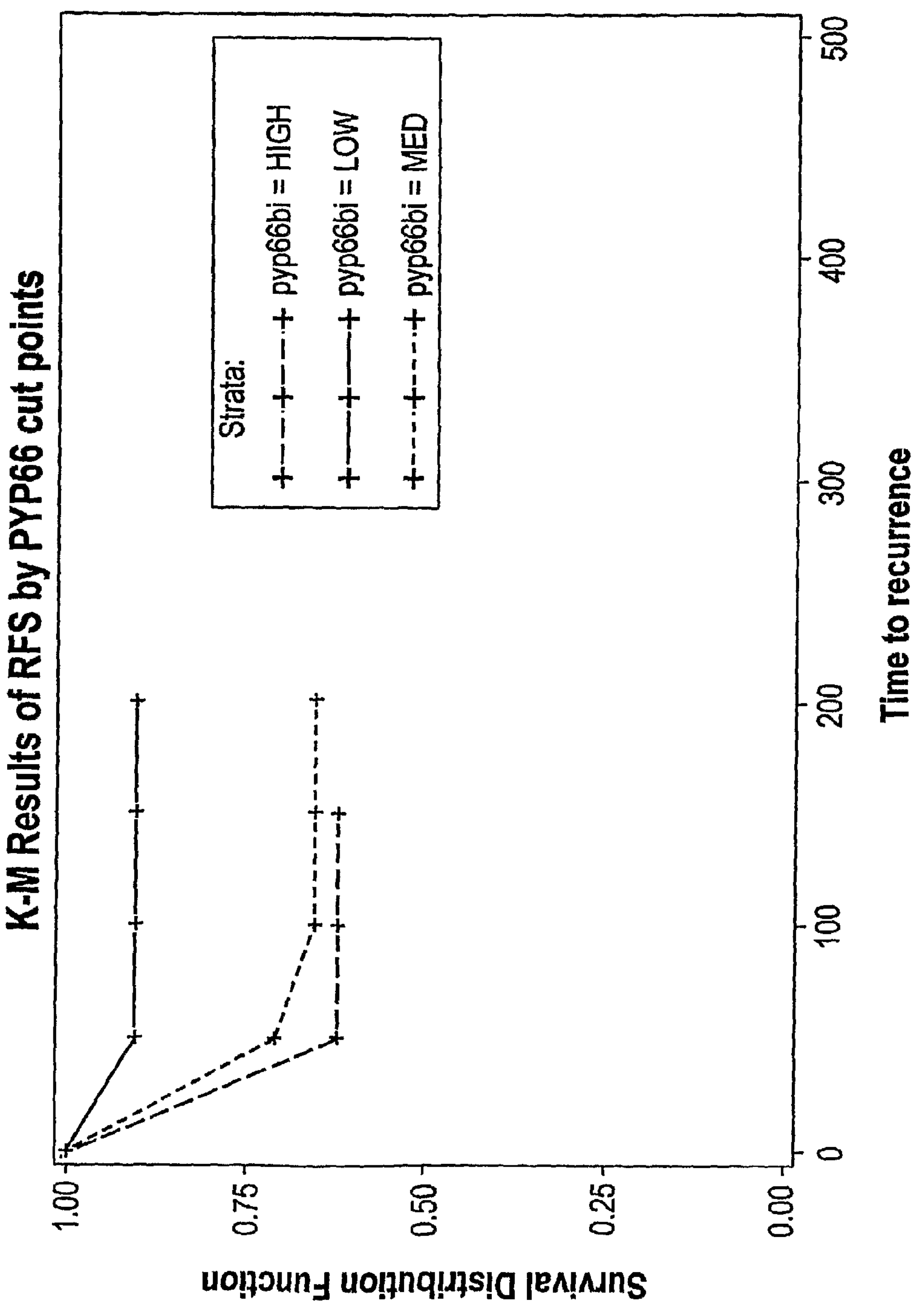
FIG. 18 depicts a Kaplan-Meier survival plot of time to recurrence-free survival as a function of the PYp66-Shc product scores for patients with Stage II and Stage III colon cancer.
Figure 19:
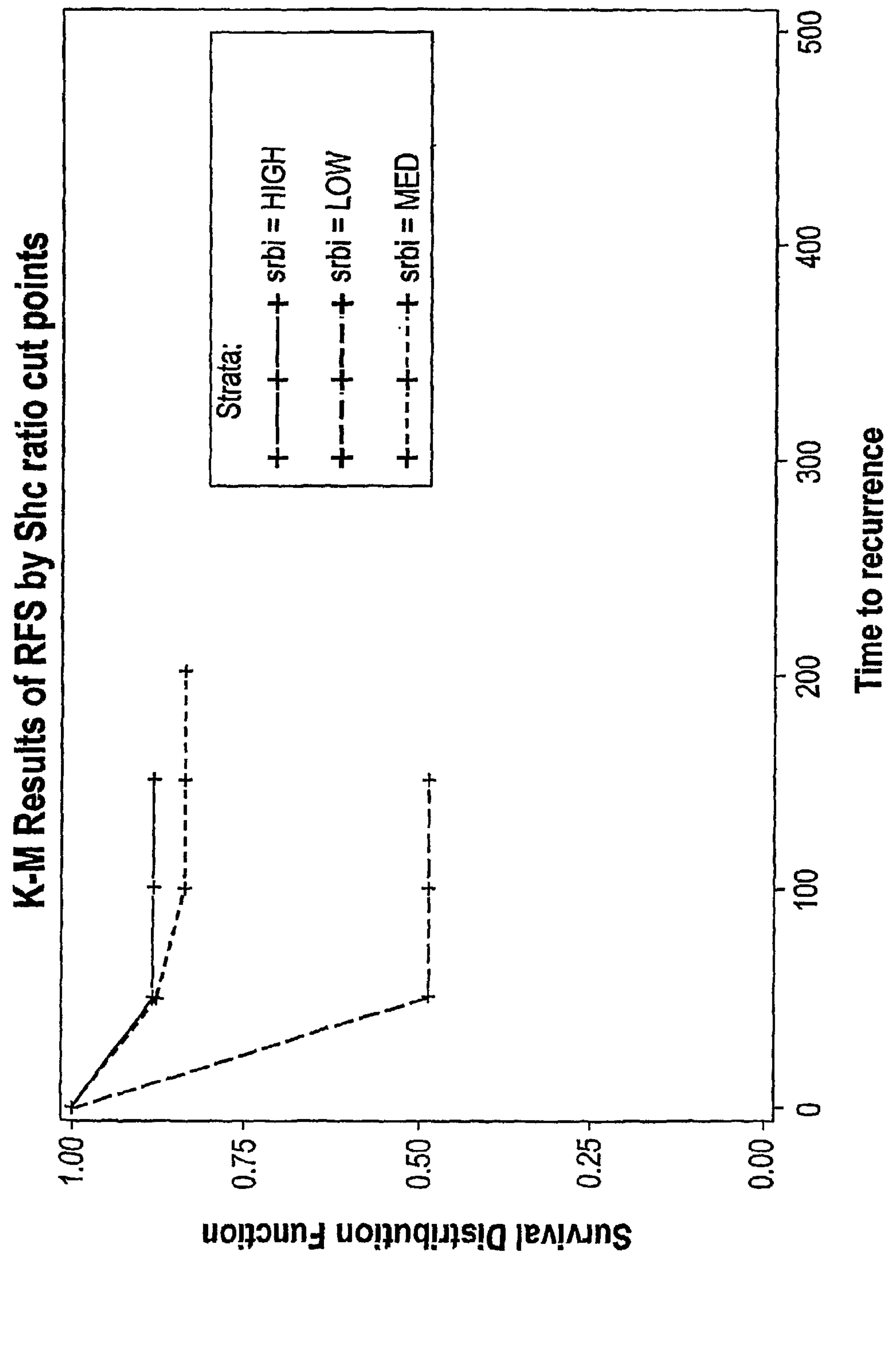
FIG. 19 depicts a Kaplan-Meier survival plot of time to recurrence-free survival as a function of the Shc ratio scores for patients with Stage II and Stage III colon cancer.

The difference between the survival of patients whose tumors have high versus low PY-Shc can be easily seen from a graph of their Kaplan-Meier survival functions (P=0.003 by univariate log rank analysis) (FIG. 6).

Details: univariate log rank analysis:

sts test pycp if stagen<4 & survdays!=. & dsdl=.

failure_d: dsd analysis time_t: survdays

Log-rank test for equality of survivor functions

| pycp | Events observed | Events expected |
|---|---|---|
| 0 | 18 | 11.36 |
| 1 | 3 | 9.64 |
| Total | 21 | 21.00 |

chi2(1) = 8.66
Pr > chi2 = 0.0032

By univariate Cox proportional hazards analysis, PY-Shc had a very strong protective effect: patients with high PY-Shc scores were 5-fold less likely to die than patients with high PY-Shc scores (P=0.0018).

Details of univariate analysis:

stcox pycp if stagen<4 & survdays!=. & dsd!=., nolog failure_d: dsd analysis time_t: survdays Cox regression—Breslow method for ties

| | | | | | |
|---|---|---|---|---|---|
| No. of subjects | = | 52 | Number of obs | = | 52 |
| No. of failures | = | 21 | | | |
| Times at risk | = | 56095 | | | |
| | | | LR chi2 (1) | = | 9.77 |
| Log likelihood | = | -69.375208 | Probl > chi2 | = | 0.0018 |

| _t | Haz. Ratio | Std. Err. | z | P > \|z\| | [95% Conf. Interval] | |
|---|---|---|---|---|---|---|
| pycp | .1903023 | .11946 | −2.64 | 0.008 | .0556048 | .6512919 |

In multivariate Cox analysis, only PY-Shc (HR=0.22, P=0.015) and the Intestinal tumor type (HR=0.38, P=0.046) remained significant in the model:

Finding the base model by including all potential covariates except PY-Shc, and then sequentially removing covariates with P-values >0.15, starting with the least significant:

stcox cther rther grade ttypens stagen if pyaverb!=. & stagen<4 & survdays!=. & dsd!=., nolog failure _d: dsd analysis time _t: survdays Cox regression—Breslow method for ties

| | | | |
|---|---|---|---|
| No. of subjects = | 48 | Number of obs = | 48 |
| No. of failures = | 20 | LR chi2(5) = | 13.27 |
| Time at risk = | 54991 | Prob > chi2 = | 0.0210 |
| Log likelihood = | −63.186434 | | |

| _t | Haz. Ratio | Std. Err. | z | P > \|z\| | [95% Conf. Interval] | |
|---|---|---|---|---|---|---|
| cther | .2986035 | .2579182 | −1.40 | 0.162 | .0549378 | 1.623 |
| rther | 1.249526 | .7784743 | 0.36 | 0.721 | .3684964 | 4.236988 |
| grade | .8619116 | .346704 | −0.37 | 0.712 | .3918022 | 1.896089 |
| ttypens | .5158454 | .1613537 | −2.12 | 0.034 | .2794269 | .9522935 |
| stagen | 2.424191 | 1.189454 | 1.80 | 0.071 | .9266511 | 6.341873 |

Dropping the least significant covariate: radiation therapy:

stcox cther grade ttypens stagen if pyaverb!=. & stagen<4 & survdays!=. & dsd!=., nolog failure _d: dad analysis time _t: survdays Cox regression—Breslow method for ties

| | |
|---|---|
| No. of subjects = 48 | Number of obs = 48 |
| No. of failures = 20 | LR chi2(4) = 13.14 |
| Time at risk = 54991 | Prob > chi2 = 0.0106 |
| Log likelihood = −63.248607 | |

| _t | Haz. Ratio | Std. Err. | z | P > \|z\| | [95% Conf. Interval] | |
|---|---|---|---|---|---|---|
| cther | .343056 | .2650404 | −1.38 | 0.166 | .0754638 | 1.559523 |
| grade | .8419936 | .3403554 | −0.43 | 0.670 | .3812689 | 1.859457 |
| ttypens | .5061001 | .1558698 | −2.21 | 0.027 | .2767461 | .9255315 |
| stagen | 2.503291 | 1.204378 | 1.91 | 0.056 | .9749512 | 6.427465 |

Dropping the next least significant covariate: grade stcox cther ttypens stagen if pyaverb!=. & stagen<4 & survdays!=. & dsd!=., nolog failure _d: dsd analysis time _t: survdays Cox regression—Breslow method for ties

| | | | |
|---|---|---|---|
| No. of subjects = | 49 | Number of obs = | 49 |
| No. of failures = | 21 | LR chi2(3) = | 13.11 |
| Time at risk = | 55193 | Prob > chi2 = | 0.0044 |
| Log likelihood = | −67.131968 | | |

| _t | Haz. Ratio | Std. Err. | z | P > \|z\| | [95% Conf. Interval] | |
|---|---|---|---|---|---|---|
| cther | .3136325 | .2404633 | −1.51 | 0.130 | .0697913 | 1.409421 |
| ttypens | .5733533 | .172348 | −1.85 | 0.064 | .3180929 | 1.033453 |
| stagen | 2.626822 | 1.164835 | 2.18 | 0.029 | 1.101476 | 6.2645 |

The above is the final base model: all covariates significant at P<0.15

Adding PY-Shc to this model:

stcox pycp cther ttypens stagen if pyaverb!=. & stagen<4 & survdays!=. & dsd!=., nolog failure _d: dsd analysis time _t: survdays Cox regression—Breslow method for ties

| | | | |
|---|---|---|---|
| No. of subjects = | 49 | Number of obs = | 49 |
| No. of failures = | 21 | LR chi2(4) = | 18.26 |
| Time at risk = | 55193 | Prob > chi2 = | 0.0011 |
| Log likelihood = | −64.56083 | | |

| _t | Haz. Ratio | Std. Err. | z | P > \|z\| | [95% Conf. Interval] | |
|---|---|---|---|---|---|---|
| pycp | .2596665 | .1704894 | −2.05 | 0.040 | .0717038 | .9403505 |
| cther | .4051888 | .3080017 | −1.19 | 0.235 | .0913318 | 1.797599 |
| ttypens | .6297452 | .2009396 | −1.45 | 0.147 | .336948 | 1.176974 |
| stagen | 1.964466 | .8232212 | 1.61 | 0.107 | .8640593 | 4.466277 |

Dropping the least significant covariate: chemotherapy stcox pycp ttypens stagen if pyaverb!=. & stagen<4 & survdays!=. & dsd!=., nolog failure _d: dsd analysis time _t: survdays Cox regression—Breslow method for ties

| | | | |
|---|---|---|---|
| No. of subjects = | 52 | Number of obs = | 52 |
| No. of failures = | 21 | LR chi2(3) = | 16.75 |
| Time at risk = | 56095 | Prob > chi2 = | 0.0008 |
| Log likelihood = | −65.88623 | | |

| _t | Haz. Ratio | Std. Err. | z | P > \|z\| | [95% Conf. Interval] | |
|---|---|---|---|---|---|---|
| pycp | .2301508 | .1475423 | −2.29 | 0.022 | .0655141 | .8085196 |
| ttypens | .5968785 | .1831276 | −1.68 | 0.093 | .3271371 | 1.089036 |
| stagen | 1.685061 | .6732254 | 1.31 | 0.192 | .7700849 | 3.687165 |

Dropping the next least significant covariate: tumor stage and separating tumor type into Diffuse(ttypens2), Intestinal (ttypens3) and all others, mostly unknown(ttypens1):

stcox pycp ttypens1 ttypens2 ttypens3 if pyaverb!=. & stagen<4 & survdays!=. & dsd!=., nolog failure _d: dsd analysis time _t: survdays note: ttypens1 dropped due to collinearity Cox regression—Breslow method for ties

| | | | |
|---|---|---|---|
| No. of subjects = | 52 | Number of obs = | 52 |
| No. of failures = | 21 | LR chi2(3) = | 14.99 |
| Time at risk = | 56095 | Prob > chi2 = | 0.0018 |
| Log likelihood = | −66.767037 | | |

| _t | Haz. Ratio | Std. Err. | z | P > \|z\| | [95% Conf. Interval] | |
|---|---|---|---|---|---|---|
| pycp | .2166127 | .1368359 | −2.42 | 0.015 | .062802 | .7471268 |
| ttypens2 | .6133317 | .3283534 | −0.91 | 0.361 | .2147811 | 1.751439 |
| ttypens3 | .2708438 | .160557 | −2.20 | 0.028 | .0847469 | .8655929 |

Dropping the least significant Diffuse(2) and co-linear All Others (1):

stcox pycp ttypens3 if pyaverb!=. & stagen<4 & survdays!=. & dsd!=., nolog failure _d: dsd analysis time _t: survdays Cox regression—Breslow method for ties

| | |
|---|---|
| No. of subjects = 52 | Number of obs = 52 |
| No. of failures = 21 | LR chi2(2) = 14.19 |
| Time at risk = 56095 | Prob > chi2 = 0.0008 |
| Log likelihood = −67.168688 | |

| _t | Haz. Ratio | Std. Err. | z | P > \|z\| | [95% Conf. Interval] | |
|---|---|---|---|---|---|---|
| pycp | .2166446 | .1364887 | −2.43 | 0.015 | .0630203 | .744758 |
| ttypens3 | .3753981 | .1845199 | −1.99 | 0.046 | .1432517 | .983749 |

An identical model is reached using a backward-stepping method.

Summary of Examples 1-6:

PY-Shc in primary tumors of patients with early stage gastric cancer appears to have significant protective effect on over-all survival. PY-Shc (but not p66 Shc) was significantly decreased in patients who died subsequent to presentation with early stage disease (Stages I & II).

As a continuous variable, PY-Shc had a strong protective ability (HR of 0.62 for 1 unit increase in PY-Shc score on 0-5 scale, or 0.092 full-scale: an 11-fold HR) that closely approached statistical significance (P=0.055).

From a dot plot of PY-Shc versus death, a cutpoint of about 1.5 clearly separated patients into those who had high PY-Shc with good prognosis (85%, 17/20 survived), and those patients who had low PY-Shc with poor prognosis (44%, 14/32 survived)(P=0.003). By univariate Cox proportional hazards analysis, high PY-Shc had a strong protective effect: patients with high PY-Shc scores were 5-fold less likely to die than patients with low PY-Shc scores (P=0.0018). In multivariate Cox analysis after adjusting for tumor grade, stage, chemotherapy and radiation therapy, only PY-Shc (HR=0.22, P=0.015) and the Intestinal tumor type (HR=0.38, P=0.046) remained as significant predictors of survival.

Example 7

Analysis of Disease Specific Survival and Recurrence Free Survival in Patients with Stage II and Stage III Colon Cancer Using a Colon Tumor Microarray The aim of this study was to evaluate the ability of the Shc proteins, along with patients' demographic and disease characteristics, to predict time to relapse and time to disease specific mortality due to colon cancer.

A blinded validation of the Shc Test was conducted on archival RIH Colon Array specimens from patients with stage II and III colon cancer. Data was collected on patient's gender, age, grade, lymphatic invasion status, and stage of disease. Since stage of disease and lymphatic invasion status were distributed identically in patients, lymphatic invasion was not included in any analysis. Data on cause of death, follow up time till death, survival status, recurrence status, and time to recurrence of disease was collected for all patients. Data was given as the average score of PY-Shc and p66-Shc staining in the range of 0-5 for each parameter. Additionally, the Shc ratio was calculated as a direct ratio of PY-Shc to p66-Shc if both test results were available. PYp66-Shc product (range of 0-5) was calculated as a direct product of PY-Shc and p66-Shc if both results are available.

Data on 130 patients was utilized from the RIH Colon Array dataset for all analyses. Out of 130 patients, 19 patients (14.6%) died of disease, 18 patients (13.9%) have had recurrence of disease. Except for 16 patients with high-grade disease, the remaining patients have had low-grade disease. Most patients (115/130; 88.5%) have had stage II disease. Following are some of the results from the analysis of DSS and RFS.

Relapse free survival (RFS) and disease specific survival (DSS) were the focus of the analyses. Relapse free survival was defined as time (months) from initial diagnosis of colon cancer to the first recurrence of disease. Disease specific survival was defined as time (months) of patient follow-up till disease specific mortality.

Summary statistics of each Shc parameter were calculated for RFS and DSS to assess if there was a significant difference in any of the Shc parameters among patient demographic and disease characteristics. Time to RFS and DSS analyses were performed using univariate K-M analyses stratified by all prognostic and Shc factors. Multivariate time to event analysis was carried out using Cox PH regression to explore predictive ability of baseline prognostic factors and Shc parameters.

Several univariate K-M and multivariate Cox PH regression models and plots were performed to derive cut off points for each of the Shc parameters for the analysis of time to disease specific death and time to relapse free survival. After several variations, the following cut points were selected based on their maximum likelihood values and log-rank p-values:

PY: LOW=<2.0; MEDIUM=2.0-3.2; HIGH=>3.2

P66: LOW=<2.1; MEDIUM=2.1-2.8; HIGH=>2.8

PYP66: LOW=<1.6; MEDIUM=1.4-2.4; HIGH=>2.4

Shc Ratio: LOW=<1.4; MEDIUM=1.4-2.2; HIGH=>2.2

The results of these analyses demonstrate the predictive ability of the Shc Test™ both in disease specific survival and relapse free survival. Higher hazard rates were associated with high p66-Shc and low Shc ratios in both disease specific survival and relapse free survival.

Disease-Specific Survival

With respect to disease-specific survival, the mean p66-Shc was significantly higher (p=0.03) in patients who died from the disease (2.37±1.02) than in patients who survived the disease (1.84±0.93). The mean Shc ratio was significantly lower (p=0.03) in patients who died from the disease (1.98±1.12) than in patients who survived the disease (2.88±3.13). The stage of the disease was found to be significant stratification prognostic factor in univariate K-M analysis with higher incidence of mortality associated with Stage III cancer. p66-Shc, the Shc ratio, as well as the PYp66-Shc product were all found to be significant stratification factors in univariate K-M analysis. Patients with high p66-Shc values were associated with a higher % of mortality. Similarly, patients with high PYp66-Shc product values were associated with a higher % of mortality. On the other hand, patients with low Shc ratio values were associated with a higher % of mortality.

Multivariate models were run including age, sex, grade, stage and Shc parameters. Since age was not a significant factor and the estimated hazard ratio (HR) was close to 1 in all of these models, this parameter was not considered in the final models. Although the grade of the disease was not significant in most of these models, the estimated HR was considerably different than 1 and, thus, was considered in the final models. The stage of disease and gender were significant in most of the models. The hazard ratio of the stage of disease was found to be between 4 to 7 indicating that a worsening of disease from Stage II to Stage III increased the risk by 4-7 times (see Table 5). p66-Shc was found to be significant in both univariate and multivariate models. Estimates of hazard ratio of 1.82 and 2.36 in univariate and multivariate models indicate a hazard increase of more than one unit in the p66-Shc results reported above. Inclusion of p66-Shc categories also provided higher hazard ratios (2.48 and 3.22 in univariate and multivariate models, respectively) consistent with continuous p66-Shc value based models. PYp66-Shc and the Shc ratio were also significant factors in both univariate and multivariate models. The direction of hazard ratios in PYp66-Shc (1.77 and 2.30 in univariate and multivariate models, respectively) was the same as that of p66-Shc, whereas the direction of hazard ratios in the Shc ratio (0.62 and 0.55 in univariate and multivariate models respectively) was the opposite, i.e., the hazard reduced with a unit increase in the Shc ratio. PY-Shc was not significant in either the continuous or categorical format. The stage of disease was a significant factor in many of the multivariate models. Sex was also significant in many of these models.

TABLE 5

Analysis of Disease Specific Survival - Cox PH Regression results

| | Continuous Variable | | | Categorical Variables | | |
|---|---|---|---|---|---|---|
| Model | HR | 95% CI | p-value | HR | 95% CI | p-value |
| PY | | | | | | |
| Univariate | 1.05 | 0.60, 1.86 | 0.85 | 1.06 | 0.47, 2.37 | 0.89 |
| Multivariate | | | | | | |
| PY | 1.14 | 0.62, 2.10 | 0.67 | 1.17 | 0.51, 2.69 | 0.70 |
| Grade | 1.43 | 0.79, 2.59 | 0.23 | 1.44 | 0.80, 2.61 | 0.22 |
| Stage | 4.05 | 1.37, 11.98 | 0.01 | 4.01 | 1.36, 11.78 | 0.01 |
| Sex | 0.37 | 0.13, 1.05 | 0.06 | 0.37 | 0.13, 1.04 | 0.06 |
| P66 | | | | | | |
| Univariate | 1.82 | 1.16, 2.85 | 0.008 | 2.48 | 1.46, 4.20 | 0.0007 |
| Multivariate | | | | | | |
| P66 | 2.36 | 1.40, 3.90 | 0.001 | 3.22 | 1.79, 5.81 | <0.0001 |
| Grade | 1.50 | 0.80, 2.80 | 0.19 | 1.62 | 0.85, 3.1 | 0.14 |
| Stage | 6.1 | 1.96, 19.20 | 0.002 | 6.97 | 2.18, 22.20 | 0.001 |
| Sex | 0.31 | 0.10, 0.90 | 0.03 | 0.38 | 0.14, 1.07 | 0.07 |
| PYP66 | | | | | | |
| Univariate | 1.77 | 1.05, 2.98 | 0.03 | 2.14 | 1.24, 3.72 | 0.007 |
| Multivariate | | | | | | |
| PYP66 | 2.30 | 1.28, 4.11 | 0.005 | 2.70 | 1.48, 4.92 | 0.001 |
| Grade | 1.48 | 0.80, 2.74 | 0.21 | 1.48 | 0.80, 2.75 | 0.21 |
| Stage | 5.67 | 1.80, 17.40 | 0.002 | 6.2 | 2.01, 19.12 | 0.002 |
| Sex | 0.34 | 0.12, 0.95 | 0.04 | 0.39 | 0.14, 1.07 | 0.07 |

TABLE 5-continued

Analysis of Disease Specific Survival - Cox PH Regression results

| | Continuous Variable | | | Categorical Variables | | |
|---|---|---|---|---|---|---|
| Model | HR | 95% CI | p-value | HR | 95% CI | p-value |
| Shc Ratio | | | | | | |
| Univariate | 0.62 | 0.34, 1.10 | 0.10 | 0.39 | 0.22, 0.72 | 0.003 |
| Multivariate | | | | | | |
| Shc | 0.55 | 0.30, 0.98 | 0.04 | 0.31 | 0.16, 0.61 | 0.0007 |
| Grade | 1.64 | 0.87, 3.10 | 0.12 | 1.66 | 0.87, 3.19 | 0.12 |
| Stage | 4.26 | 1.40, 13.01 | 0.01 | 5.27 | 1.67, 16.65 | 0.005 |
| Sex | 0.35 | 0.12, 1.01 | 0.052 | 0.34 | 0.12, 0.99 | 0.05 |

Relapse Free Survival

With respect to relapse free survival, the mean p66-Shc was significantly higher (p=0.02) in patients who died from the disease (2.41±1.04) than in patients who survived the disease (1.86±0.92). The mean Shc ratio was significantly lower (p=0.04) in patients who died from the disease (2.01±1.16) than in patients who survived the disease (2.87±3.13). The stage of disease was found to be a significant stratification prognostic factor in univariate K-M analysis with higher incidence of mortality associated with Stage III cancer. p66-Shc, the Shc ratio, as well as the PYp66-Shc product were all found to be significant stratification factors in univariate K-M analysis. Patients with high p66-Shc values (categorized as High) were associated with a higher % of mortality. Similarly, patients with high PYp66-Shc product values were associated with a higher % of mortality. On the other hand, patients with low Shc ratio values were associated with higher % of mortality.

Multivariate models were run including age, sex, grade, stage and Shc parameters. Age was not a significant factor (and HR was close to 1) in any of the models and was not considered in the final models. Although the grade of disease was not significant in most of these models, estimated HR was considerably different than 1 and, thus, was considered in the final models. The stage of disease and gender were significant in most of these models. The hazard ratio of the stage of the disease was found to be between 4 to 6.50 indicating that a worsening of disease from Stage II to Stage III increases the hazard by 4-6.50 times (see Table 6). p66-Shc was found to be significant in both univariate and multivariate models. Estimates of hazard rate of 1.82 and 2.36 in univariate and multivariate models indicate a hazard increase of more than one unit in the p66-Shc results reported above. Inclusion of p66-Shc categories also provided higher hazard rates (2.48 and 3.22 in univariate and multivariate models, respectively) consistent with continuous p66-Shc value based models. PYp66-Shc and the Shc ratio were also significant factors in both univariate and multivariate models. The direction of hazard ratios in PYp66-Shc (1.77 and 2.30 in univariate and multivariate models, respectively) was the same as that of p66-Shc whereas the direction of hazard ratios in the Shc ratio (0.62 and 0.55 in univariate and multivariate models respectively) was the opposite, i.e., hazard reduced with a unit increase in the Shc ratio. PY-Shc was not significant in either the continuous or categorical format in these models. The stage of disease was a significant factor in many of the multivariate models. Sex was also significant in many of these models.

TABLE 6

| Analysis of recurrence Free Survival - Cox PH Regression results (N = 97) | | | | | | |
|---|---|---|---|---|---|---|
| | Continuous Variable | | | Categorical Variables | | |
| Model | HR | 95% CI | p-value | HR | 95% CI | p-value |
| PY | | | | | | |
| Univariate | 1.16 | 0.66, 2.05 | 0.61 | 1.31 | 0.54, 3.19 | 0.54 |
| Multivariate | | | | | | |
| PY | 1.29 | 0.69, 2.43 | 0.42 | 1.52 | 0.59, 3.93 | 0.38 |
| Grade | 1.58 | 0.88, 2.87 | 0.30 | 1.61 | 0.89, 2.94 | 0.11 |
| Stage | 4.36 | 1.47, 12.90 | 0.008 | 4.28 | 1.46, 12.54 | 0.008 |
| Sex | 0.33 | 0.20, 1.00 | 0.051 | 0.33 | 0.11, 0.99 | 0.048 |
| P66 | | | | | | |
| Univariate | 1.78 | 1.14, 2.80 | 0.01 | 2.48 | 1.46, 4.20 | 0.007 |
| Multivariate | | | | | | |
| P66 | 2.28 | 1.3, 3.9 | 0.003 | 3.04 | 1.72, 5.37 | 0.001 |
| Grade | 1.73 | 0.91, 3.33 | 0.09 | 1.87 | 0.95, 3.69 | 0.07 |
| Stage | 5.80 | 1.80, 18.3 | 0.002 | 6.33 | 2.0, 20.02 | 0.002 |
| Sex | 0.24 | 0.07, 0.82 | 0.02 | 0.29 | 0.09, 0.94 | 0.04 |
| PYP66 | | | | | | |
| Univariate | 1.84 | 1.08, 3.13 | 0.02 | 2.19 | 1.25, 3.82 | 0.006 |
| Multivariate | | | | | | |
| PYP66 | 2.45 | 1.32, 4.54 | 0.004 | 2.85 | 1.54, 5.30 | 0.009 |
| Grade | 1.69 | 0.90, 3.20 | 0.11 | 1.72 | 0.92, 3.23 | 0.09 |
| Stage | 5.98 | 1.90, 18.59 | 0.002 | 6.58 | 2.11, 20.48 | 0.001 |
| Sex | 0.27 | 0.08, 0.84 | 0.02 | 0.31 | 0.10, 0.92 | 0.04 |
| Shc Ratio | | | | | | |
| Univariate | 0.67 | 0.39, 1.14 | 0.14 | 0.41 | 0.22, 0.77 | 0.005 |
| Multivariate | | | | | | |
| Shc | 0.62 | 0.35, 1.09 | 0.09 | 0.35 | 0.17, 0.69 | 0.003 |
| Grade | 1.75 | 0.93, 3.33 | 0.08 | 1.85 | 0.95, 3.60 | 0.07 |
| Stage | 4.03 | 1.31, 12.40 | 0.02 | 4.82 | 1.5, 15.44 | 0.008 |
| Sex | 0.31 | 0.09, 0.99 | 0.048 | 0.28 | 0.09, 0.95 | 0.04 |

Tables 7 and 8 summarize the distribution of patient characteristics by disease-specific survival and recurrence-free survival and the Shc parameters by disease-specific survival, respectively.

TABLE 7

Distribution of patient characteristics by DSS and RFS.

disease specific survival (0 = N, 1 = Y)

| dss | Frequency | Percent | Cumulative Frequency | Cumulative Percent |
|---|---|---|---|---|
| No | 19 | 15.70 | 19 | 15.70 |
| Yes | 102 | 84.30 | 121 | 100.00 |

Frequency Missing = 9

RF Survival (0 = N, 1 = Y)

| rfs | Frequency | Percent | Cumulative Frequency | Cumulative Percent |
|---|---|---|---|---|
| No | 18 | 15.00 | 18 | 15.00 |
| Yes | 102 | 85.00 | 120 | 100.00 |

Frequency Missing = 10

| dss | grade | Frequency | Percent | Cumulative Frequency | Cumulative Percent |
|---|---|---|---|---|---|
| No | LOW | 11 | 9.09 | 11 | 9.09 |
| No | LOW (FH) | 4 | 3.31 | 15 | 12.40 |
| No | HIGH | 4 | 3.31 | 19 | 15.70 |
| Yes | LOW | 73 | 60.33 | 92 | 76.03 |
| Yes | LOW (FH) | 16 | 13.22 | 108 | 89.26 |
| Yes | HIGH | 11 | 9.09 | 119 | 98.35 |
| Yes | UNKNOWN | 2 | 1.65 | 121 | 100.00 |

Frequency Missing = 9

| rfs | grade | Frequency | Percent | Cumulative Frequency | Cumulative Percent |
|---|---|---|---|---|---|
| No | LOW | 10 | 8.33 | 10 | 8.33 |
| No | LOW (FH) | 4 | 3.33 | 14 | 11.67 |
| No | HIGH | 4 | 3.33 | 18 | 15.00 |
| Yes | LOW | 74 | 61.67 | 92 | 76.67 |
| Yes | LOW (FH) | 15 | 12.50 | 107 | 89.17 |
| Yes | HIGH | 11 | 9.17 | 118 | 98.33 |
| Yes | UNKNOWN | 2 | 1.67 | 120 | 100.00 |

Frequency Missing = 10

| dss | stage | Frequency | Percent | Cumulative Frequency | Cumulative Percent |
|---|---|---|---|---|---|
| No | Stage II | 14 | 11.57 | 14 | 11.57 |
| No | Stage III | 5 | 4.13 | 19 | 15.70 |
| Yes | Stage II | 93 | 76.86 | 112 | 92.56 |
| Yes | Stage III | 7 | 5.79 | 119 | 98.35 |
| Yes | Unknown | 2 | 1.65 | 121 | 100.00 |

Frequency Missing = 9

| rfs | stage | Frequency | Percent | Cumulative Frequency | Cumulative Percent |
|---|---|---|---|---|---|
| No | Stage II | 13 | 10.83 | 13 | 10.83 |
| No | Stage III | 5 | 4.17 | 18 | 15.00 |
| Yes | Stage II | 93 | 77.50 | 111 | 92.50 |
| Yes | Stage III | 7 | 5.83 | 118 | 98.33 |
| Yes | Unknown | 2 | 1.67 | 120 | 100.00 |

Frequency Missing = 10

TABLE 8

Summary Statistics of Shc Parameters by DSD.

| Variable | Label | N | Mean | Median | Std Dev | Minimum | Maximum |
|---|---|---|---|---|---|---|---|
| Summary statistics of Shc parameters by DSS disease specific survival (0 = N, 1 = Y) = Unknown The MEANS Procedure | | | | | | | |
| PY | PY | 8 | 3.3518750 | 3.4000000 | 1.1000543 | 1.5000000 | 4.8000000 |
| P66 | P66 | 9 | 1.6553704 | 1.7333333 | 0.5835677 | 1.0400000 | 2.7000000 |
| pyp66 | pyp66 | 8 | 1.0499042 | 1.1248333 | 0.4827817 | 0.3150000 | 1.7522500 |
| shc | shc ratio | 8 | 2.3067450 | 2.0726744 | 0.9223935 | 1.4285714 | 4.0000000 |

TABLE 8-continued

Summary Statistics of Shc Parameters by DSD.

| Variable | Label | N | Mean | Median | Std Dev | Minimum | Maximum |
|---|---|---|---|---|---|---|---|
| disease specific survival (0 = N, 1 = Y) = No | | | | | | | |
| PY | PY | 19 | 3.7401417 | 3.9500000 | 0.7358285 | 2.2000000 | 4.8500000 |
| P66 | P66 | 19 | 2.3758704 | 2.6000000 | 1.0248724 | 0.5500000 | 4.1666667 |
| pyp66 | pyp66 | 19 | 1.8301914 | 1.9530000 | 0.8882739 | 0.2420000 | 3.3611111 |
| shc | shc ratio | 19 | 1.9898913 | 1.6534091 | −1.1153655 | 0.7378641 | 4.4705882 |
| disease specific survival (0 = N, 1 = Y) = Yes | | | | | | | |
| PY | PY | 102 | 3.6814161 | 3.7666667 | 0.8266572 | 1.2000000 | 4.9000000 |
| P66 | P66 | 102 | 1.8488017 | 1.7875000 | 0.9276498 | 0.1000000 | 4.7000000 |
| pyp66 | pyp66 | 102 | 1.4314517 | 1.3362500 | 0.8039269 | 0.0440000 | 3.6000000 |
| shc | shc ratio | 102 | 2.8838360 | 2.0818875 | 3.1269292 | 0.7659574 | 22.0000000 |
| Summary statistics of Shc parameters by RFS<br>RF Survival (0 = N, 1 = Y) = Unknown<br>The MEANS Procedure | | | | | | | |
| PY | PY | 9 | 3.3461111 | 3.3000000 | 1.0291518 | 1.5000000 | 4.8000000 |
| P66 | P66 | 10 | 1.6031667 | 1.4666667 | 0.5744253 | 1.0400000 | 2.7000000 |
| pyp66 | pyp66 | 9 | 1.0163593 | 1.0976667 | 0.4626778 | 0.3150000 | 1.7522500 |
| shc | shc ratio | 9 | 2.3739694 | 2.2500000 | 0.8860760 | 1.4285714 | 4.0000000 |
| RF Survival (0 = N, 1 = Y) = No | | | | | | | |
| PY | PY | 18 | 3.7826496 | 3.9916667 | 0.7327634 | 2.2000000 | 4.8500000 |
| P66 | P66 | 18 | 2.4092521 | 2.6333333 | 1.0439021 | 0.5500000 | 4.1666667 |
| pyp66 | pyp66 | 18 | 1.8731951 | 1.9587222 | 0.8934429 | 0.2420000 | 3.3611111 |
| shc | shc ratio | 18 | 2.0073265 | 1.5829545 | 1.1450342 | 0.7378641 | 4.4705882 |
| RF Survival (0 = N, 1 = Y) = Yes | | | | | | | |
| PY | PY | 102 | 3.6782298 | 3.7666667 | 0.8287655 | 1.2000000 | 4.9000000 |
| P66 | P66 | 102 | 1.8550926 | 1.7875000 | 0.9249216 | 0.1000000 | 4.7000000 |
| pyp66 | pyp66 | 102 | 1.4344726 | 1.3362500 | 0.8019097 | 0.0440000 | 3.6000000 |
| shc | shc ratio | 102 | 2.8717212 | 2.0719004 | 3.1292129 | 0.7659574 | 22.0000000 |

From the above summary statistics, p-values were calculated using t-test and Wilcoxon rank-sum test depending on if normality assumption is met or not. The p-values for the different tests are reported in Tables 9 and 10.

TABLE 9

Tests of significance of mean difference in Shc parameters DS Survival (Yes, No) and RF Survival (Yes, No)

| Parameters | DS Survival (Y, N) p-value | RF Survival (Y, N) p-value |
|---|---|---|
| PY | 0.75 | 0.59 |
| P66 | 0.03 | 0.02 |
| PYP66 | 0.08 | 0.06 |
| Shc Ratio | 0.03* | 0.04* |

*Indicates Wilcoxon rank-sum test since normality assumption is violated

TABLE 10

Univariate K-M Analysis Results for Disease Specific Survival and Recurrence Free Survival

| | DS Survival Log-rank p-value | RF Survival Log-rank p-value |
|---|---|---|
| Grade of Disease | 0.50 | 0.40 |
| Stage | 0.01 | 0.007 |
| PY (<2.0; 2.0-3.2; >3.2) | 0.23 | 0.37 |
| P66 (<2.1; 2.1-2.8; >2.8) | 0.002 | 0.001 |

TABLE 10-continued

Univariate K-M Analysis Results for Disease Specific Survival and Recurrence Free Survival

| | DS Survival Log-rank p-value | RF Survival Log-rank p-value |
|---|---|---|
| PYP66 (<1.6; 1.6-2.4; >2.4) | 0.02 | 0.01 |
| Shc Ratio (<1.4; 1.4-2.2; >2.2) | 0.002 | 0.002 |

Example 8

Shc Amounts in Various Tumor Types

The amounts of PY-Shc and p66-Shc in various tumor types were determined as described herein. The results are presented below in Table 11.

TABLE 11

Shc Amounts in Various Tumor Types.

| Tumor | PY | p66 |
|---|---|---|
| Adrenal Adenocarcinoma | 2.1 | 2.3 |
| Astrocytoma | 2.3 | 3.2 |
| Basal Cell Carinoma | 3.7 | 3.6 |
| Carcinoid Tumor in the Liver | 1.9 | 2.1 |
| Cholangiocarcinoma | 4.0 | 2.9 |
| Cholangiocarcinoma | 3.5 | 2.9 |
| Cholangiocarcinoma | 3.8 | 1.4 |
| Cholangiocarcinoma | 3.5 | 1.8 |

TABLE 11-continued

| Shc Amounts in Various Tumor Types. | | |
|---|---|---|
| Tumor | PY | p66 |
| Esophageal Adenocarcinoma | 3.6 | 3.4 |
| Esophageal Adenocarcinoma | 3.3 | 3.5 |
| Fibrosarcoma | 3.2 | 2.1 |
| Fibrosarcoma | 2.8 | 2.8 |
| GIST | 4.1 | 3.0 |
| GIST | 3.3 | 2.6 |
| Glioma | 3.3 | 3.7 |
| Hepatocellular Carcinoma | 2.0 | 3.9 |
| High Grade Sarcoma | 3.4 | 2.9 |
| Immature Teratoma | 3.3 | 2.5 |
| Keratoacanthoma | 4.4 | 4.4 |
| Leiomyosarcoma | 4.7 | 4.3 |
| Leiomyosarcoma | 4.7 | 4.5 |
| Lung Adenocarcinoma | 3.0 | 2.7 |
| Lung Adenocarcinoma | 4.4 | 3.2 |
| Lung Adenocarcinoma | 4.0 | 3.1 |
| Lung Adenocarcinoma | 4.3 | 1.7 |
| Lung Adenocarcinoma | 4.8 | 3.6 |
| Lung Adenocarcinoma | 3.9 | 2.3 |
| Lung Adenocarcinoma | 3.7 | 4.6 |
| Lung adenocarcinoma | 3.8 | 2.3 |
| Lung Squamous Cell Carcinoma | 3.6 | 2.1 |
| Lung Squamous Cell Carcinoma | 3.9 | 4.4 |
| Lung Squanous Cell Carcinoma | 3.2 | 2.2 |
| Metastatic Lung Adenocarcinoma | 4.5 | 2.7 |
| Metastatic Lung Adenocarcinoma | 4.2 | 1.8 |
| Pancreatic Adenocarcinoma | 2.7 | 2.4 |
| Pancreatic Endocrine Carcinoma | 3.3 | 1.9 |
| Pancreatic Enodcrine Carcinoma | 3.0 | 2.3 |
| Papillary Carcinoma of Thyroid | 3.9 | 4.5 |
| Papillary Renal Cell Carcinoma | 3.8 | 4.3 |
| Parotid Mixed Tumor (Carcinosarcoma) | 3.1 | 2.8 |
| Renal (Clear Cell) Carcinoma (high grade) | 1.4 | 4.0 |
| Renal (Clear Cell) Carcinoma (high grade) | 2.6 | 2.7 |
| Renal Cell Carcinoma | 2.8 | 2.9 |
| Salivary Adenocarcinoma | 4.6 | 4.2 |
| Salivary Adenocarcinoma | 4.6 | 3.8 |
| Salivary Pleomorphic Adenoma | 3.1 | 4.2 |
| Salivary Pleomorphic Adenoma | 3.3 | 2.7 |
| Sarcoidosis | 2.8 | 4.4 |
| Small Intestinal Carcinoid Tumor | 2.5 | 1.5 |
| Squamous Cell Carcinoma of Lung | 3.0 | 1.3 |
| T-cell Lymphoma | 3.0 | 4.1 |
| Transitional Cell Carcinoma of Bladder | 3.6 | 2.3 |
| Transitional Cell Carcinoma of Bladder | 3.0 | 1.4 |
| Transitional Cell Carcinoma of Bladder | 3.5 | 3.1 |
| Tubular Adenoma of Colon | 2.9 | 1.7 |
| Wilm's Tumor | 3.5 | 4.7 |
| Wilm's Tumor | 3.0 | 3.5 |
| Wilm's Tumor | 3.4 | 4.4 |
| Wilm's Tumor | 3.0 | 3.7 |

Example 9

Analyses of p66-Shc and TP53 in Aggressive Cancer Cells

While not wishing to be bound by theory, one proposed mechanistic model of tumor development that explains the abilities of high levels of PY-Shc and of low levels of p66-Shc to identify aggressive cancer cells, e.g., breast cancer cells, is that high oxidative stress in developing, aggressive tumor cells creates a strong selective pressure to avoid stress-induced apoptosis. Stress-induced apoptosis requires functioning p66-Shc, but is also dependent upon TP53 (Trinei et al, supra). Thus, the apoptotic pressure of oxidative stress selects for successful aggressive tumor cells that have either down-regulated p66-Shc and down-regulated TP53, by e.g., avoiding p66-Shc mediated feedback down-regulation of receptor tyrosine kinases (RTK) signaling to Erk and c-FOS, or those that have altered the expression of other factors effecting apoptosis, e.g., factors deriving from growth-factor signaling, mitochondrial activity, invasion by the host's inflammatory cells, and by vascular re-perfusion of hypoxic tissue in response to successful tumor angiogenesis.

For example, if mutated TP53 is estimated by IHC assay employing traditional low anti-TP53 concentrations to visualize accumulating TP53, (of which about 60% is actually normal TP53 (believed to be accumulating in a futile attempt at apoptosis (see, e.g., Askmalm, M. S., et al. (2004) *Acta Oncolog* 43:235), then most of the accumulated TP53 associated with low levels of p66 Shc should be normal TP53, and would not be a prognostic hazard. On the other hand, if high concentrations of anti-TP53 are used to estimate TP53 (McCabe et al. (2005) *J Natl Cancer Inst* 97:1808), cells containing normal to low levels of TP53 stain darkly. These same cells, however, do not stain at all with the traditional low anti-TP53 antibody concentration. Cells remaining unstained, then, express "zero" TP53, presumably due to mutations that prevent (antigenically recognizable) TP53 from being synthesized. As previously reported (McCabe et al. supra), 24% of primary breast cancers were identified in this manner as "mutant" TP53zero tumors (an additional 12% had accumulating TP53). Thus, most of these TP53zero tumors, as well as all of the prognostic ability of TP53zero, resides in tumors that express normal and/or high levels of p66-Shc.

Thus, for cancers, such as, for example, naïve breast cancers, i.e., breast cancers not exposed to systemic adjuvant therapies, the selective pressure to down-regulate p66-Shc is mitigated if the tumor cell finds an alternative mechanism(s) to bypass oxidative-stress-induced apoptosis. Such mechanisms include, for example, up-regulation of anti-apoptotic factors (such as Bcl-2 or Bcl-xL, and the like) or down-regulation of pro-apoptotic factors such as PI3'Kinase, PTEN or TP53, i.e., activating mutations in PI3'Kinase and inactivating mutations in PTEN each increase AKT activity which allows MDM2 to down-regulate TP53.

For example, PI3'Kinase drives AKT phosphorylation, and this is counterbalanced by PTEN protein which, when functioning normally, reduces AKT activation (phosphorylation) which in turn reduces MDM2 phosphorylation, thereby preventing MDM2 migration from the cytoplasm to the nucleus where MDM2 would normally target TP53 for proteolytic destruction. Thus, active PTEN helps to drive TP53 accumulation and thus apoptosis. Activating mutations of PI3'Kinase or inactivating mutations of PTEN, then, allow hyperactivation of AKT to P-AKT, resulting in TP53 levels near zero. (Activating mutations in PI3 kinase occur in about 30% of colon cancers (Samuels, et al. (2004) *Science* 304:554).) The PI3'kinase and PTEN mutants may appear as TP53zero tumors using the high anti-TP53 antibody concentration assay. While not TP53 mutations per se, functionally and prognostically, they would be indistinguishable. This distinction is important in identifying patients that re be candidates for molecular targeting of the PI3' kinase-AKT-MDM2 pathway.

TP53 has been reported to be mutated in 12-40% of breast cancers (Oliver, et al. (2006) *Clin Cancer Res* 12:1157-1167). Studies using gene sequence analysis report that the incidence of TP53 mutation ranges from 16% to 40%. Typical IHC analysis using the D07 monoclonal antibody does not find TP53zero mutants (i.e., no antigenically detectable TP53 protein produced). TP53zero mutants tend to be nonsense mutations, or mutations involving insertions/deletions, or splicing errors. In one study of 266 patients (Askmalm, M. S., et al. (2004) *Acta Oncolog* 43:235) in which both IHC positively and actual gene sequencing was performed, IHC detected 48% (22/44) of TP53 mutations. However, of 54 IHC positive, 61% (32/44) had non-mutated TP53. Mutations at some sites engender different degrees of prognostic hazard, and this, thus, reflects varying degrees of reduction in TP53 function. It has been shown that p66 Shc-mediated apoptosis in response to oxidative stress is strongly dependent upon active TP53 (Trinnei, et al *Oncogene,* 21(24): 3872-78, 2002). Thus, normal and/or high levels of p66 Shc in naive breast cancers that had reduced their expression of TP53 either by mutations that either blocked TP53 expression or produced functionally inactive TP53. Functionally inactive TP53 can be detected by its tendency to accumulate in the cell (over-expressed by traditional IHC or by its complete absence in cells stained using high concentrations of anti-TP53 antibody (McCabe, et al supra). TP53 that has been down-regulated by mutations in PI3'Kinase or PTEN, especially when coupled with active receptor-tyrosine kinases, appear as TP53 negative using the high anti-TP53 IHC technique.

Nevertheless, normal TP53 may accumulate in some tumor cells either in response to oxidative stress-induced DNA damage, or in response to oxidative stress itself (due to TP53 stabilization). This gives rise to some frequency of "false-positive" TP53 mutation by IHC analysis. Such "false-positive" TP53 is not a prognostic hazard, and is either independent of p66 Shc levels, or actually preferentially correlated with low levels of p66 Shc expression as the remaining normal cellular machinery tries futilely to achieve homeostatic death.

Based on the foregoing analysis, it is believed that nearly all of TP53 prognostic ability would be associated with normal to high levels of p66 Shc expression. To test this, TP53 levels (determined using amounts of anti-TP53 designed to detect high, accumulated levels of TP53) were analyzed with respect to p66-Shc and DSS (disease-specific survival) in the BCCA V6 breast cancer tumor microarray dataset (TMA) (Frackelton et al, *Proc Amer Assoc Cancer Res* 46:LB201).

p66-Shc scores from the BCCA 01-011 V6 breast TMA were transformed into fractional ranks. A variable was defined as p66bi, where p66bi=1 if p66 Shc fractional rank was less than 0.5; 2 if p66 Shc fractional rank was >0.5. TP53 staining was performed by traditional methods using the DO-7 antibody and scored at GPEC as having either negative, weak or strong staining; these were re-coded as 0 if negative, 1 otherwise. Of all stained tumors (307), 8% showed weak TP53 staining and 8% showed strong TP53 staining.

The ability of accumulating TP53 to predict disease-specific survival was assessed first by log-rank univariate analysis of TP53, as a function of p66-Shc levels, and then by univariate and multivariate Cox proportional hazards analyses using STATA 8 software.

Figure 20:
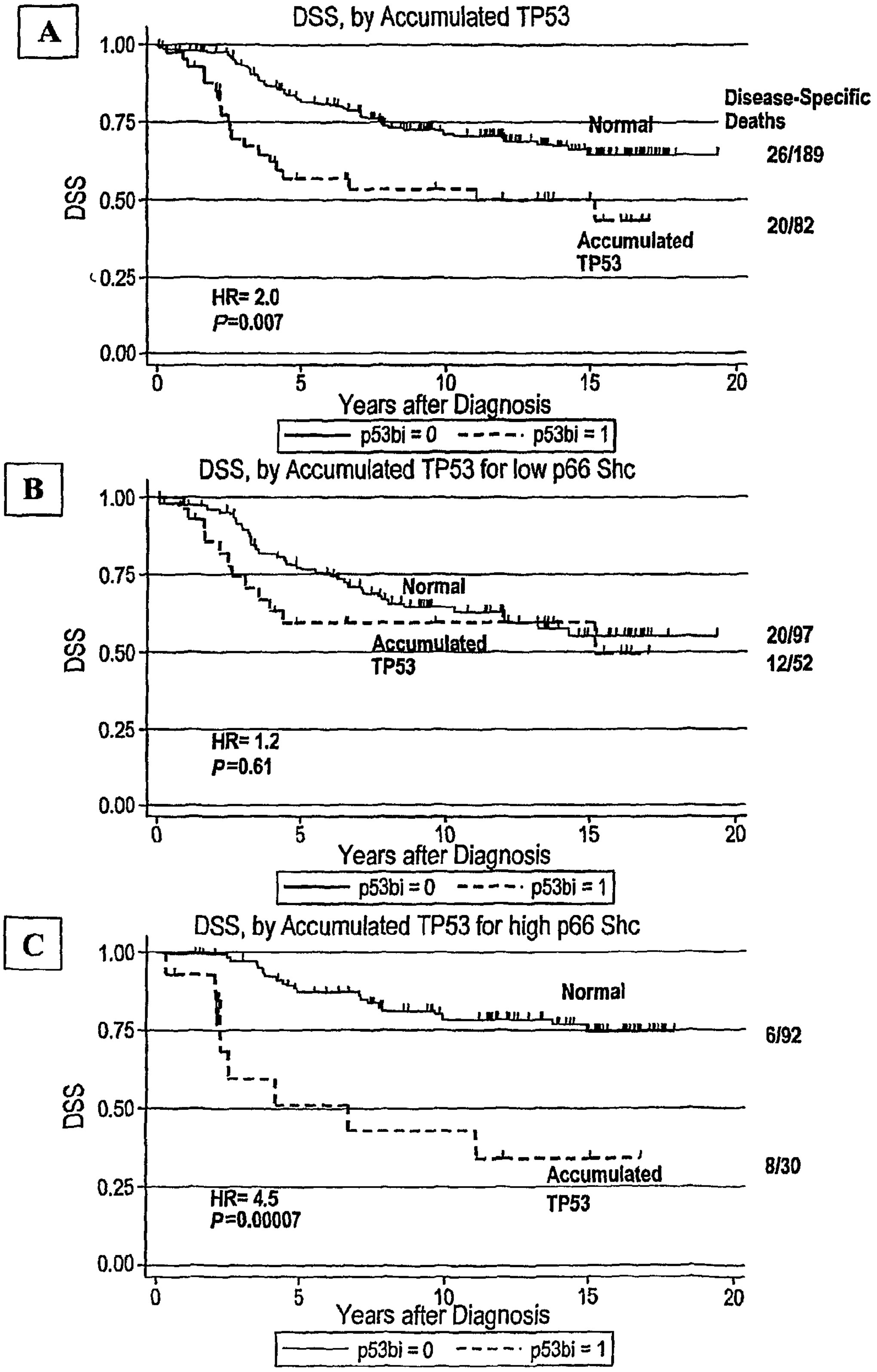
FIGS. 20A-20C depict Kaplan-Meier survival plots stratified by the presence or absence of accumulating TP53 for the total population for all tumors (20A), tumors with low p66 Shc (20B), and tumors with high p66 Shc (20 C).

Disease-specific survival curves stratified by the presence or absence of accumulating TP53 for the total population are shown in FIGS. 20A, 20B, and 20C for all tumors, tumors with low p66-Shc, and tumors with high p66-Shc, respectively. For patients having high levels of p66-Shc, those accumulating "mutated" TP53 had much poorer outcome than patients without accumulating TP53 (P=0.00003, see Table 12). In contrast, for patients having low levels of p66-Shc, patients with accumulating TP53 had only a slightly poorer outcome than patients without accumulating TP53, and this poorer outcome did not attain significance (P=0.6) (FIG. 20B). However, there was a trend towards significance (P=0.26) at early times after diagnosis (<6 yrs) in patients with low p66 Shc. Consistent with other studies on TP53, virtually all of the specific hazard of TP53 is observed before 9 years (FIGS. 20A and 20C).

By Cox proportional hazards univariate analysis, all the hazard associated with accumulating TP53 was found in patients whose tumors have high levels of p66-Shc, with these patients having a >2-fold higher risk of dying from their disease (with a 100-fold greater significance than that of the total population (Table 12). This difference in risk was maintained in multivariate Cox models (HR=9, P=0.001, for TP53 in patients with high p66-Shc, adjusting for PY-Shc, nodal status, Her-2, and Ki67 as covariates. Of 46 patients with accumulating TP53, 32 (70%) were associated with low p66-Shc. This is only slightly more that the 60% false-positive rate (non-mutated TP53) published for accumulating TP53 by IHC measurement.

TABLE 12

TP53 Prognostic Ability Partitions with High p66 Shc in Breast Cancers

| | TP53 | | | |
|---|---|---|---|---|
| | Log Rank | Cox univariate Model | | |
| p66 Shc (n) | XP-Value | HR | 95% CI | P-Value |
| All (82/271) | 0.006 | 2.0 | 1.2-3.3 | 0.007 |
| Low (52/149) | 0.606 | 1.2 | 0.6-2.3 | 0.606 |
| High (30/122) | 0.00003 | 4.8 | 2.1-11 | 0.00007 |

Consistent with the model explaining the ability of p66 Shc to identify aggressive tumors, nearly all the hazard associated with accumulating TP53 is found in patients whose tumors have high levels of p66 Shc. Further consistent both with the model predictions and published data on the rate of false-positively for estimation of mutated TP53 by IHC assay, a majority of accumulating TP53 had no prognostic value, and was associated with low levels of p66 Shc. Thus, the independent predictive values of p66 Shc and TP53 allow more accurate prediction of a patient's risk and thereby aid the clinician in making treatment decisions.

The details of the foregoing analyses are set forth below.

sts test p53bi failure _d: event analysis time _t: total_fo

Log-rank test for equality of survivor functions

| p53bi | Events observed | Events expected |
|---|---|---|
| 0 | 73 | 83.50 |
| 1 | 23 | 12.50 |
| Total | 96 | 96.00 |
| | chi2(1) = | 10.17 |
| | Pr > chi2 = | 0.0014 |

sts test p53bi if p66bi!=.

failure _d: event analysis time _t: total_fo

| Log-rank test for equality of survivor functions | | |
|---|---|---|
| p53bi | Events observed | Events expected |
| 0 | 62 | 70.64 |
| 1 | 20 | 11.36 |
| Total | 82 | 82.00 |
| | chi2(1) = | 7.65 |
| | Pr > chi2 = | 0.0057 |

sts test p53bi if p66bi==1 failure _d: event analysis time _t: total_fo

| Log-rank test for equality of survivor functions | | |
|---|---|---|
| p53bi | Events observed | Events expected |
| 0 | 40 | 41.49 |
| 1 | 12 | 10.51 |
| Total | 52 | 52.00 |
| | chi2(1) = | 0.27 |
| | Pr > chi2 = | 0.6059 |

sts test p53bi if p66bi==2 failure _d: event analysis time _t: total_fo

| Log-rank test for equality of survivor functions | | |
|---|---|---|
| p53bi | Events observed | Events expected |
| 0 | 22 | 27.88 |
| 1 | 8 | 2.12 |
| Total | 30 | 30.00 |
| | chi2(1) = | 17.64 |
| | Pr > chi2 = | 0.0000 |

*All of tp53 prognostic/predictive ability resides in tumors with high p66 Shc (top 50% p66 Shc scores)

display chi2tail(1,17.64)

00002669

*Cox analysis stcox p53bi if p66bi!=., nolog failure _d: event analysis time _t: total_fo Cox regression—Breslow method for ties

| | | | |
|---|---|---|---|
| No. of subjects = | 271 | Number of obs = | 271 |
| No. of failures = | 82 | LR chi2(1) = | 6.47 |
| Time at risk = | 2733.080003 | Prob > chi2 = | 0.0110 |
| Log likelihood = | −428.62988 | | |

| _t | Haz. Ratio | Std. Err. | z | P > \|z\| | [95% Conf. Interval] | |
|---|---|---|---|---|---|---|
| p53bi | 2.009326 | .517324 | 2.71 | 0.007 | 1.213106 | 3.328143 |

stcox p53bi if p66bi==1, nolog failure _d: event analysis time _t: total_fo

Cox regression—Breslow method for ties

| | | | |
|---|---|---|---|
| No. of subjects = | 149 | Number of obs = | 149 |
| No. of failures = | 52 | LR chi2(1) = | 0.26 |
| Time at risk = | 1436.580003 | Prob > chi2 = | 0.6119 |
| Log likelihood = | −241.1356 | | |

| _t | Haz. Ratio | Std. Err. | z | P > \|z\| | [95% Conf. Interval] | |
|---|---|---|---|---|---|---|
| p53bi | 1.185175 | .3907641 | 0.52 | 0.606 | .6210588 | 2.261685 |

stcox p53bi if p66bi==2, nolog failure _d: event analysis time _t: total_fo

Cox regression—Breslow method for ties

| | | | |
|---|---|---|---|
| No. of subjects = | 122 | Number of obs = | 122 |
| No. of failures = | 30 | LR chi2(1) = | 10.90 |
| Time at risk = | 1296.5 | Prob > chi2 = | 0.0010 |
| Log likelihood = | −129.77782 | | |

| _t | Haz. Ratio | Std. Err. | z | P > \|z\| | [95% Conf. Interval] | |
|---|---|---|---|---|---|---|
| p53bi | 4.837309 | 2.007533 | 3.80 | 0.000 | 2.1446 | 10.91092 |

display 1-norm(3.80)

00007235

Example 10

Both p66-Shc and TP53 are Strong and Independent Prognostic Markers for Disease Recurrence and Disease-Specific Survival in Early Stage Colon Cancer TP53 is mutated in 40-60% of early stage colon cancers (Iacopetta B *Hum Mutat* (2003) 21:271-276; Lane DP. (1992) *Nature* 358:15-16; Russo et al. (2005) *J Clin Oncol,* 23: 7518-7528). However, functionally, mutations in PI3Kinase (110 kD subunit) (30% of colorectal cancers: Samuels, et al. (2004) *Science*) or PTEN (18% of colorectal cancers: Nassif, et al. (2004) *Oncogene* 23(2):617-28) similarly lower TP53 expression and, thus, bring the frequency of dysregulated (non-functional) TP53 to about 80% or more. All of these and their prognostic hazard are found mostly in tumors with high p66-Shc. Indeed, analysis of accumulated TP53 expression and its association with high levels of p66-Shc in the RIH colon dataset described above in Example 7, is consistent with this.

As shown in Table 13, despite there being nearly twice as many p53 positive tumors amongst tumors also having the lowest 60% of p66 Shc scores, 10 of 14 associated with accumulated p53 were in the 40% of tumors that expressed the highest levels of p66 Shc.

Table 13. Most Disease Specific Deaths from Colon Cancer Occur in Patients with accumulating TP53 whose Tumors also Expressed High Levels of p66 Shc Definitions: p53, TP53 accumulated==1; not==0. p66quint, p66 Shc scores in quintiles (1 thru 5) by fractional rank. dsd, disease-specific death==1 if yes; 0 if no Stata calculations:

tab p53 p66quint

| Avg Score | p66quint | | | | | |
|---|---|---|---|---|---|---|
| p53 | 1 | 2 | 3 | 4 | 5 | Total |
| 0 | 12 | 7 | 8 | 9 | 7 | 43 |
| 1 | 10 | 12 | 15 | 6 | 14 | 57 |
| Total | 22 | 19 | 23 | 15 | 21 | 100 |

tab p53 p66quint if dsd==O

| Avg Score | p66quint | | | | | |
|---|---|---|---|---|---|---|
| p53 | 1 | 2 | 3 | 4 | 5 | Total |
| 0 | 11 | 6 | 8 | 8 | 6 | 39 |
| 1 | 6 | 10 | 12 | 3 | 5 | 36 |
| Total | 17 | 16 | 20 | 11 | 11 | 75 |

tab p53 p66quint if dsd==1

| Avg Score | p66quint | | | | |
|---|---|---|---|---|---|
| p53 | 1 | 2 | 4 | 5 | Total |
| 0 | 0 | 0 | 1 | 1 | 2 |
| 1 | 3 | 1 | 2 | 8 | 14 |
| Total | 3 | 1 | 3 | 9 | 16 |

Table 3. p66 Shc and TP53 are very strong and independent predictors of poor outcome in early stage colon cancer.

Definitions: p66s, p66 Shc scores converted to a continuous 0-1 scale. p53, TP53 scores as in Table 2. sexn, SEX==1 if female; 2 if male. stage, Stage=2 if stage 11 disease; 3 if stage III diseaes. recurrencestatus, 1 if disease recurred; 0 if not. recurrencetimemths, number of months until recurrence or until last contact.

stcox p66s p53 sexn stage if stage!=9, nolog failure _d: recurrencestatus analysis time _t: recurrencetimemths Cox regression—Breslow method for ties

| | | | |
|---|---|---|---|
| No. of subjects = | 87 | Number of obs = | 87 |
| No. of failures = | 16 | LR chi2(4) = | 24.12 |
| Time at risk = | 8482 | Prob > chi2 = | 0.0001 |
| Log likelihood = | −57.582036 | | |

| _t | Haz. Ratio | Std. Err. | z | P > \|z\| | [95% Conf. Interval] | |
|---|---|---|---|---|---|---|
| p66s | 50.99151 | 74.50429 | 2.69 | 0.007 | 2.909359 | 893.7137 |
| p53 | 6.59409 | 5.057439 | 2.46 | 0.014 | 1.466603 | 29.64811 |
| sexn | 4.898338 | 3.099392 | 2.51 | 0.012 | 1.417282 | 16.92938 |
| stage | 6.22182 | 4.087546 | 2.78 | 0.005 | 1.716737 | 22.54919 |

Based on these analyses, both p66-Shc and TP53 are very strong and independent prognostic markers for disease recurrence in early stage colon cancer. The same analyses also demonstrate that both p66-Shc and TP53 are very strong and independent prognostic markers for disease-specific death.

Therefore, (high) p66-Shc is a hazard in colon cancer because it is identifying tumors with dysregulated TP53. Accordingly, these patients would respond poorly to cytotoxic chemotherapy, but should respond well to taxol (TP53 is not involved in taxol-mediated cell death). Therefore, p66 Shc levels would be high in these 80% of patients. Thus, high p66 Shc would in large part equate with mutated (down-regulated) TP53, and thus high p66 Shc would appear as a prognostic hazard, a surrogate marker for the prevalent dysregulated TP53.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a human subject being prognosed for gastrointestinal cancer recurrence, the method comprising:

a) determining the amount of tyrosine phosphorylated Shc (PY-Shc) and/or p66-Shc present in a biological sample derived from said subject; and b) comparing said amount to a control amount of tyrosine phosphorylated Shc (PY-Shc) and/or p66-Shc present in a control sample, wherein said p66-Shc is Shc adaptor protein of SEQ ID NO:4, and PY-Shc is p66-Shc with a tyrosine residue phosphorylated at one of positions 349, 350 or 427 of SEQ ID NO:4, wherein a control amount of tyrosine phosphorylated Shc (PY-Shc) and/or p66-Shc in a cell or a sample is derived from a subject not afflicted with cancer, and wherein a decreased amount of tyrosine phosphorylated Shc (PY-Shc) or an increased amount of p66-Shc in said sample relative to the amount in the control sample indicates that the gastrointestinal cancer will recur in said subject, and an increased amount of tyrosine phosphorylated Shc (PY-Shc) or a decreased amount of p66-Shc in said sample relative to the amount in the control sample indicates that the gastrointestinal cancer will not recur in said subject, thereby the prognosed cancer recurrence in the subject will be treated.

2. The method according to claim 1, wherein the cancer is selected from the group consisting of gastric cancer and colon cancer.

3. The method according to claim 1, wherein said determining the amount of tyrosine phosphorylated Shc (PY-Shc) and/or p66-Shc in said sample is carried out by contacting said sample with an antibody that specifically binds to tyrosine phosphorylated Shc (PY-Shc) and/or p66-Shc in said sample and using said antibody in an immunohistochemical assay.

4. The method of claim 1, wherein the sample is a tumor tissue.

5. The method of claim 4, wherein said sample is a tumor tissue sample selected from the group consisting of gastric tissue, small intestine tissue, and large intestine tissue.

6. The method of claim 1, wherein only the amount of p66-Shc is determined.

7. The method of claim 1, wherein the amounts of both p66-Shc and tyrosine phosphorylated Shc (PY-Shc) are measured.

8. The method of claim 7, wherein a Shc mathematical relationship is determined.

9. The method of claim 8, wherein the Shc mathematical relationship that is determined is a Shc ratio of Shc and p66-Shc.

10. The method of claim 1, wherein determining the amount of tyrosine phosphorylated Shc (PY-Shc) and/or p66-Shc comprises the use of a detectable antibody that specifically binds to p66-Shc and/or tyrosine phosphorylated Shc (PY-Shc).

11. The method of claim 10, wherein the determination step comprises the use of a technique selected from the group consisting of immunohistochemistry, immunocytochemistry, flow cytometry, and ELISA.

* * * * *